US011136600B2

(12) United States Patent
Papapetridis et al.

(10) Patent No.: US 11,136,600 B2
(45) Date of Patent: Oct. 5, 2021

(54) EUKARYOTIC CELL WITH INCREASED PRODUCTION OF FERMENTATION PRODUCT

(71) Applicant: DSM IP Assets B.V., Heerlen (NL)

(72) Inventors: Ioannis Papapetridis, Delft (NL); Jacobus Thomas Pronk, Delft (NL); Antonius Jeroen Adriaan Van Maris, Stockholm (SE); Paul Klaassen, Echt (NL)

(73) Assignee: DSM IP Assets B.V., Heerlen (NL)

( * ) Notice: Subject to any disclaimer, the term of this patent is extended or adjusted under 35 U.S.C. 154(b) by 152 days.

(21) Appl. No.: 15/766,184

(22) PCT Filed: Oct. 3, 2016

(86) PCT No.: PCT/EP2016/073561
§ 371 (c)(1),
(2) Date: Apr. 5, 2018

(87) PCT Pub. No.: WO2017/060195
PCT Pub. Date: Apr. 13, 2017

(65) Prior Publication Data
US 2018/0291404 A1    Oct. 11, 2018

(30) Foreign Application Priority Data

Oct. 6, 2015 (EP) .................... 15188645

(51) Int. Cl.
*C12P 7/02* (2006.01)
*C12P 7/10* (2006.01)
*C12N 1/18* (2006.01)
*C12N 9/00* (2006.01)
*C12N 9/04* (2006.01)
*C12N 9/02* (2006.01)
*C12N 9/12* (2006.01)
*C12N 9/18* (2006.01)
*C12N 15/52* (2006.01)

(52) U.S. Cl.
CPC ............. *C12P 7/10* (2013.01); *C12N 9/0006* (2013.01); *C12N 9/0008* (2013.01); *C12N 9/1205* (2013.01); *C12N 9/18* (2013.01); *C12N 9/93* (2013.01); *C12N 15/52* (2013.01); *C12Y 101/01044* (2013.01); *C12P 2203/00* (2013.01); *C12Y 101/01008* (2013.01); *C12Y 101/01049* (2013.01); *C12Y 101/05003* (2013.01); *C12Y 101/99* (2013.01); *C12Y 102/0101* (2013.01); *C12Y 301/03021* (2013.01); *C12Y 503/01005* (2013.01); *C12Y 602/0101* (2013.01); *Y02E 50/10* (2013.01)

(58) Field of Classification Search
CPC .......... C12Y 101/99; C12Y 503/01005; C12Y 101/01008; C12P 2203/00; C12P 7/10; C12P 7/02; C12N 9/0008; C12N 9/18; C12N 9/93; C12N 9/0006
USPC ........................ 435/252.2, 161, 189, 252.1
See application file for complete search history.

(56) References Cited

U.S. PATENT DOCUMENTS

2005/0153411 A1   7/2005   Wahlbom et al.
2016/0208291 A1   7/2016   Klaassen et al.

FOREIGN PATENT DOCUMENTS

| EP | 2277989 A1 | 1/2011 |
| WO | 2015028582 A2 | 3/2015 |
| WO | 2015028583 A2 | 3/2015 |
| WO | 2015148272 A1 | 10/2015 |

OTHER PUBLICATIONS

Davos et al., (Proteins: Structure, Function and Genetics, 2000, vol. 41: 98-107.*
Kwiatkowski et al., (Biochemistry 38:11643-11650, 1999.*
Kisselev L., (Structure, 2002, vol. 10: 8-9.*
Wristlock et al., (Quarterly Reviews of Biophysics 2003, vol. 36 (3): 307-340.*
International Search Report issued in counterpart International Application No. PCT/EP2016/073561, dated Jan. 4, 2017.
Medina VG; Almering MJH; Van Maris AJA; Pronk JT: "Elimination of glycerol production in anaerobic culture of a *Saccharomyces cerevisiae* strain engineered to use acetic acid as an electron acceptor", Applied and Environmental Microbiology, vol. 76, 2010, pp. 190-195.
Pickl Andreas et al: "The oxidative pentose phosphate pathway in the haloarchaeon Haloferax volcanii involves a novel type of glucose-6-phosphate dehydrogenase—The archaeal Zwischenferment.", FEBS Letters Apr. 28, 2015, vol. 589, No. 10, Apr. 28, 2015 (Apr. 28, 2015), pp. 1105-1111.

* cited by examiner

*Primary Examiner* — Robert B Mondesi
*Assistant Examiner* — Mohammad Y Meah
(74) *Attorney, Agent, or Firm* — McBee Moore & Vanik IP, LLC

(57) ABSTRACT

The present invention relates to a eukaryotic cell that is genetically modified comprising one or more heterologous gene encoding:
a) D-glucose-6-phosphate dehydrogenase and/or
b) 6-phosphogluconate dehydrogenase; and/or
c) glucose dehydrogenase, gluconolactonase and gluconate kinase,
wherein a), b) and glucose dehydrogenase in c) are $NAD^+$ dependent.

24 Claims, 6 Drawing Sheets
Specification includes a Sequence Listing.

SEQUENCE LISTING

```
<160> NUMBER OF SEQ ID NOS: 53

<210> SEQ ID NO 1
<211> LENGTH: 1819
<212> TYPE: DNA
<213> ORGANISM: Artificial Sequence
<220> FEATURE:
<223> OTHER INFORMATION: gndA cassette

<400> SEQUENCE: 1 gcgatacect gcgatcttcg agacctaact acatagtgtt taaagattac ggatatttaa      60
cttacttaga ataatgccat tttttgagt tataataatc ctacgttagt gtgagcggga     120
tttaaactgt gaggacctta atacattcag acacttctgc ggtatcaccc tacttattcc     180
cttcgagatt atatctagga acccatcagg ttggtggaag attacccgtt ctaagacttt     240
tcagcttcct ctattgatgt tacacctgga caccccttt ctggcatcca gtttttaatc     300
ttcagtggca tgtgagattc tccgaaatta attaaagcaa tcacacaatt ctctcggata     360
ccacctcggt tgaaactgac aggtggtttg ttacgcatgc taatgcaaag gagcctatat     420 accttggct cggctgctgt aacagggaat ataaagggca gcataattta ggagtttagt     480
gaacttgcaa catttactat tttcccttct tacgtaaata ttttttctttt taattctaaa     540 tcaatctttt tcaattttt gtttgtattc ttttcttgct taaatctata actacaaaaa     600
```

```
acacatacat aaactaaaaa tgaagttggc tattattggt ttgggtaaga tgggtggtaa      660
catggctaga agattgttga agcacggtat tgaagttgtt ggtttcgact tcaaccaaga      720
cgctgttaac caaatttctt tgaccaacgg tatgattcca gcttcttctg ttgaagacgc      780
tgtttctaag ttgtctggtg aaccaagaaa gattgtttgg attatgttgc catctggtga      840
cattaccgaa aaccaaatta aggacttggt tccattgttg tctaagggtg acattattgt      900
tgacggtggt aactctaact acaagcactc tcaaagaaga ggtgcttggt tggctgaaca      960
cggtattgaa ttcattgact gtggtacctc tggtggtatt tggggtttgg acaacggtta     1020
ctgtttgatg tacggtggtt ctaaggacgt tgctgacgct gttgttccaa ttatgcaagc     1080
tttggctcac gctgacagag ttgggctca cgttggtcca gttggttctg gtcacttcac      1140
caagatgatt cacaacggta ttgaatacgg tatgatgcaa gctttcgctg aaggtttgga     1200
cttgttgaag ggtaaggaag aattcaactt ggacttggct caaattaccg aattgtggag     1260
acacggttct gttgttagat cttggttgtt ggacttgacc gctgaagctt tggctcacga     1320
ccaagaattg tctgctattg ctccatacgt tgctgactct ggtgaaggta gatggaccgt     1380
tgttgaagct gttgaccaag tgttgctgc tccagttttg accttggctt tgcaaatgag      1440
attcgcttct caagaagaca ccggttactc ttacaagttg ttgtctatga tgagaaacgc     1500
tttcggtggt cacgctgtta agaccaagta acaggcccct tttcctttgt cgatatcatg     1560
taattagtta tgtcacgctt acattcacgc cctcccccca catccgctct aaccgaaaag     1620
gaaggagtta gacaacctga agtctaggtc cctatttatt tttttatagt tatgttagta     1680
ttaagaacgt tatttatatt tcaaattttt cttttttttc tgtacaaacg cgtgtacgca     1740
tgtaacatta tactgaaaac cttgcttgag aaggttttgg gacgctcgaa ggctttaatt     1800
tgcttcgcta atctgcgcg                                                  1819
```

<210> SEQ ID NO 2
<211> LENGTH: 303
<212> TYPE: PRT
<213> ORGANISM: Artificial Sequence
<220> FEATURE:
<223> OTHER INFORMATION: GndA protein (Methylobacillus flagellates)

<400> SEQUENCE: 2

```
Met Lys Leu Ala Ile Ile Gly Leu Gly Lys Met Gly Gly Asn Met Ala
1               5                   10                  15

Arg Arg Leu Leu Lys His Gly Ile Glu Val Val Gly Phe Asp Phe Asn
            20                  25                  30

Gln Asp Ala Val Asn Gln Ile Ser Leu Thr Asn Gly Met Ile Pro Ala
        35                  40                  45

Ser Ser Val Glu Asp Ala Val Ser Lys Leu Ser Gly Glu Pro Arg Lys
    50                  55                  60

Ile Val Trp Ile Met Leu Pro Ser Gly Asp Ile Thr Glu Asn Gln Ile
65                  70                  75                  80

Lys Asp Leu Val Pro Leu Leu Ser Lys Gly Asp Ile Ile Val Asp Gly
                85                  90                  95

Gly Asn Ser Asn Tyr Lys His Ser Gln Arg Arg Gly Ala Trp Leu Ala
            100                 105                 110

Glu His Gly Ile Glu Phe Ile Asp Cys Gly Thr Ser Gly Gly Ile Trp
        115                 120                 125

Gly Leu Asp Asn Gly Tyr Cys Leu Met Tyr Gly Gly Ser Lys Asp Ala
    130                 135                 140
```

```
Ala Asp Ala Val Val Pro Ile Met Gln Ala Leu Ala His Ala Asp Arg
145                 150                 155                 160

Gly Trp Ala His Val Gly Pro Val Gly Ser Gly His Phe Thr Lys Met
            165                 170                 175

Ile His Asn Gly Ile Glu Tyr Gly Met Met Gln Ala Phe Ala Glu Gly
            180                 185                 190

Leu Asp Leu Leu Lys Gly Lys Glu Glu Phe Asn Leu Asp Leu Ala Gln
            195                 200                 205

Ile Thr Glu Leu Trp Arg His Gly Ser Val Val Arg Ser Trp Leu Leu
210                 215                 220

Asp Leu Thr Ala Glu Ala Leu Ala His Asp Gln Glu Leu Ser Ala Ile
225                 230                 235                 240

Ala Pro Tyr Val Ala Asp Ser Gly Glu Gly Arg Trp Thr Val Val Glu
            245                 250                 255

Ala Val Asp Gln Gly Val Ala Ala Pro Val Leu Thr Leu Ala Leu Gln
            260                 265                 270

Met Arg Phe Ala Ser Gln Glu Asp Thr Gly Tyr Ser Tyr Lys Leu Leu
            275                 280                 285

Ser Met Met Arg Asn Ala Phe Gly Gly His Ala Val Lys Thr Lys
            290                 295                 300
```

<210> SEQ ID NO 3
<211> LENGTH: 1906
<212> TYPE: DNA
<213> ORGANISM: Artificial Sequence
<220> FEATURE:
<223> OTHER INFORMATION: gox1705 cassette

<400> SEQUENCE: 3

```
gcgataccct gcgatcttcg agacctaact acatagtgtt taaagattac ggatatttaa      60
cttacttaga ataatgccat ttttttgagt tataataatc ctacgttagt gtgagcggga     120
tttaaactgt gaggacctta atacattcag acacttctgc ggtatcaccc tacttattcc     180
cttcgagatt atatctagga acccatcagg ttggtggaag attacccgtt ctaagacttt     240
tcagcttcct ctattgatgt tacacctgga cacccctttt ctggcatcca gtttttaatc     300
ttcagtggca tgtgagattc tccgaaatta attaaagcaa tcacacaatt ctctcggata     360
ccacctcggt tgaaactgac aggtggtttg ttacgcatgc taatgcaaag gagcctatat     420
acctttggct cggctgctgt aacagggaat ataagggca gcataattta ggagtttagt      480
gaacttgcaa cattt ас таt tttccctt ст tacgtaaata tttttc тттт таат т с таaa   540
tcaatctttt tcaattttt gtttgtattc tttt cttgct taaatctata actacaaaaa     600
acacatacat aaactaaaaa tgagaattgg tattattggt tgggtagaa tgggtggtaa      660
cattgctgtt agattgacca gacacggtca cgacgttgtt gttcacgaca gaacctctga    720
agttaccacc tctgttgttg gtagatgtga agctggtaga gctaccccag ctgacacctt   780
ggctgacatg gctaagttgt tggaaggtga cgaacacaga gttgtttggg ttatgttgcc    840
agctggtgct attaccgaag actgtgttca acaattgggt ggtttgttgg gtagaggtga    900
cattattatt gacggtggta acacctacta caaggacgac gttagaagat ctgctgaatt    960
ggctgaaaag ggtatttctt acgttgacgt tggtacctct ggtggtgttt ggggtttgga   1020
aagaggttac tgtatgatgt tcggtggtac caaggaaacc gctgaataca ttgacccaat  1080
tttgtctgct ttggctccag gtattggtga cgttccaaga accccaggta gagacgaagc  1140
```

-continued

```
tggtcacgac ccaagagctg aacaaggtta cttgcactgt ggtccagctg gttctggtca   1200
cttcgttaag atggttcaca acggtattga atacggtatg atgcaagctt tcgctgaagg   1260
tttcgacatt atgaagtcta agaactctcc aattttggct gaaaaggaca gattcgaatt   1320
gaacatgggt gacattgctg aagtttggag aagaggttct gttgtttctt cttggttgtt   1380
ggacttgacc gctgaagctt tgaccagatc tgaaaccttg aacgaattct ctggtgaagt   1440
tgctgactct ggtgaaggta gatggaccat tgaagctgct attgaagaag acgttccagc   1500
tccagttatg accgctgctt tgttcaccag attcagatct agatctggta caacttcgc    1560 tgaaaagatt ttgtctgctc aaagattcgg tttcggtggt cacgttgaaa gaagtaaca   1620 ggccccttt cctttgtcga tatcatgtaa ttagttatgt cacgcttaca ttcacgccct   1680
ccccccacat ccgctctaac cgaaaaggaa ggagttagac aacctgaagt ctaggtccct   1740
atttattttt ttatagttat gttagtatta agaacgttat ttatatttca aatttttctt   1800 tttttctgt acaaacgcgt gtacgcatgt aacattatac tgaaaacctt gcttgagaag   1860
gttttgggac gctcgaaggc tttaatttgc ttcgctaatc tgcgcg                   1906
```

<210> SEQ ID NO 4
<211> LENGTH: 332
<212> TYPE: PRT
<213> ORGANISM: Artificial Sequence
<220> FEATURE:
<223> OTHER INFORMATION: Gox1705 protein (Gluconobacter oxydans 621H)

<400> SEQUENCE: 4

```
Met Arg Ile Gly Ile Ile Gly Leu Gly Arg Met Gly Gly Asn Ile Ala
1               5                   10                  15

Val Arg Leu Thr Arg His Gly His Asp Val Val His Asp Arg Thr
            20                  25                  30

Ser Glu Val Thr Thr Ser Val Val Gly Arg Cys Glu Ala Gly Arg Ala
        35                  40                  45

Thr Pro Ala Asp Thr Leu Ala Asp Met Ala Lys Leu Leu Glu Gly Asp
    50                  55                  60

Glu His Arg Val Val Trp Val Met Leu Pro Ala Gly Ala Ile Thr Glu
65                  70                  75                  80

Asp Cys Val Gln Gln Leu Gly Gly Leu Leu Gly Arg Gly Asp Ile Ile
                85                  90                  95

Ile Asp Gly Gly Asn Thr Tyr Tyr Lys Asp Asp Val Arg Arg Ser Ala
            100                 105                 110

Glu Leu Ala Glu Lys Gly Ile Ser Tyr Val Asp Val Gly Thr Ser Gly
        115                 120                 125

Gly Val Trp Gly Leu Glu Arg Gly Tyr Cys Met Met Phe Gly Gly Thr
    130                 135                 140

Lys Glu Thr Ala Glu Tyr Ile Asp Pro Ile Leu Ser Ala Leu Ala Pro
145                 150                 155                 160

Gly Ile Gly Asp Val Pro Arg Thr Pro Gly Arg Asp Glu Ala Gly His
                165                 170                 175

Asp Pro Arg Ala Glu Gln Gly Tyr Leu His Cys Gly Pro Ala Gly Ser
            180                 185                 190

Gly His Phe Val Lys Met Val His Asn Gly Ile Glu Tyr Gly Met Met
        195                 200                 205

Gln Ala Phe Ala Glu Gly Phe Asp Ile Met Lys Ser Lys Asn Ser Pro
    210                 215                 220

Ile Leu Ala Glu Lys Asp Arg Phe Glu Leu Asn Met Gly Asp Ile Ala
```

```
            225                 230                 235                 240
Glu Val Trp Arg Arg Gly Ser Val Val Ser Ser Trp Leu Leu Asp Leu
                245                 250                 255

Thr Ala Glu Ala Leu Thr Arg Ser Glu Thr Leu Asn Glu Phe Ser Gly
            260                 265                 270

Glu Val Ala Asp Ser Gly Glu Gly Arg Trp Thr Ile Glu Ala Ala Ile
            275                 280                 285

Glu Glu Asp Val Pro Ala Pro Val Met Thr Ala Ala Leu Phe Thr Arg
        290                 295                 300

Phe Arg Ser Arg Ser Gly Asn Asn Phe Ala Glu Lys Ile Leu Ser Ala
305                 310                 315                 320

Gln Arg Phe Gly Phe Gly Gly His Val Glu Lys Lys
                325                 330

<210> SEQ ID NO 5
<211> LENGTH: 1906
<212> TYPE: DNA
<213> ORGANISM: Artificial Sequence
<220> FEATURE:
<223> OTHER INFORMATION: 6pgdh cassette

<400> SEQUENCE: 5
gcgatacccT gcgatcttcg agacctaact acatagtgtt taaagattac ggatatttaa      60
cttacttaga ataatgccat tttttTgagt tataataatc ctacgttagt gtgagcggga     120
tttaaactgt gaggacctta atacattcag acacttctgc ggtatcaccc tacttattcc     180
cttcgagatt atatctagga acccatcagg ttggtggaag attacccgtt ctaagacttt     240
tcagcttcct ctattgatgt tacacctgga cacccctttt ctggcatcca gtttttaatc     300
ttcagtggca tgtgagattc tccgaaatta ttaaagcaa tcacacaatt ctctcggata     360
ccacctcggt tgaaactgac aggtggtttg ttacgcatgc taatgcaaag gagcctatat     420
acctttggct cggctgctgt aacagggaat ataaagggca gcataattta ggagtttagt     480
gaacttgcaa catttactat tttcccttct tacgtaaata ttttTctttt taattctaaa     540
tcaatctttt tcaattttTt gtttgtattc ttttcttgct taaatctata actacaaaaa     600
acacatacat aaactaaaaa tgcaattggg tatgattggt ttgggtagaa tgggtggtaa     660
cattgttaga agattgatga gacacggtca ctctaccgtt gtttacgaca aggacgctaa     720
ggctgttgct ggtttggctg ctgacggtgc tgttggttct gctaccttgg aagaattcgt     780
tgctaagttg gaaagaccaa gaaccgcttg ggttatgttg ccagctggta gaattaccga     840 accaccatt gacaccattg ctggtgttat gcaagaaggt gacgttatta ttgacggtgg     900
taacaccttc tggcaagacg acgttagaag aggtaaggct ttgaaggcta gaggtattca     960
ctacgttgac gttggtacct ctggtggtgt ttggggtttg acagaggttt actgtatgat    1020
gattggtggt gaaaagcaag ttgttgacag attggaccca attttcgctg ctttggctcc    1080
aggtgctggt gacattccaa gaaccgaagg tagagaaggt agagacccaa gaattgaaca    1140
aggttacatt cacgctggtc cagttggtgc tggtcacttc gttaagatga ttcacaacgg    1200
tattgaatac ggtttgatgc aagcttacgc tgaaggtttc gacattttga agaacgctaa    1260
cattgacgct ttgccagctg accacagata cgacttcgac ttggctgaca ttgctgaagt    1320
ttggagaaga ggttctgtta ttccatcttg gttgttggac ttgacctcta ccgctttggc    1380
tgactctcca gctttggctg aatactctgg tttcgttgaa gactctggtg aaggtagatg    1440
gaccgttaac gctgctattg acgaagctgt tccagctgaa gttttgaccg ctgctttgta    1500
```

```
caccagattc agatctagaa aggaacacac cttcgctgaa aagattttgt ctgctatgag    1560
agctggtttc ggtggtcaca aggaaccaaa gcaaccaggt gcttctaagc caaagtaaca    1620 ggccccttt cctttgtcga tatcatgtaa ttagttatgt cacgcttaca ttcacgccct    1680
ccccccacat ccgctctaac cgaaaaggaa ggagttagaa aacctgaagt ctaggtccct    1740 attattttt ttatagttat gttagtatta agaacgttat ttatatttca aattttctt    1800 tttttctgt acaaacgcgt gtacgcatgt aacattatac tgaaaacctt gcttgagaag    1860
gttttgggac gctcgaaggc tttaatttgc ttcgctaatc tgcgcg                  1906
```

```
<210> SEQ ID NO 6
<211> LENGTH: 332
<212> TYPE: PRT
<213> ORGANISM: Artificial Sequence
<220> FEATURE:
<223> OTHER INFORMATION: 6pgdh protein WP_011089498.1 (Multispecies
      [Bradyrhizobium])

<400> SEQUENCE: 6
```

```
Met Gln Leu Gly Met Ile Gly Leu Gly Arg Met Gly Gly Asn Ile Val
1               5                   10                  15

Arg Arg Leu Met Arg His Gly His Ser Thr Val Val Tyr Asp Lys Asp
                20                  25                  30

Ala Lys Ala Val Ala Gly Leu Ala Ala Asp Gly Ala Val Gly Ser Ala
            35                  40                  45

Thr Leu Glu Glu Phe Val Ala Lys Leu Glu Arg Pro Arg Thr Ala Trp
        50                  55                  60

Val Met Leu Pro Ala Gly Arg Ile Thr Glu Thr Thr Ile Asp Thr Ile
65                  70                  75                  80

Ala Gly Val Met Gln Glu Gly Asp Val Ile Ile Asp Gly Gly Asn Thr
                85                  90                  95

Phe Trp Gln Asp Asp Val Arg Arg Gly Lys Ala Leu Lys Ala Arg Gly
            100                 105                 110

Ile His Tyr Val Asp Val Gly Thr Ser Gly Gly Val Trp Gly Leu Asp
        115                 120                 125

Arg Gly Tyr Cys Met Met Ile Gly Gly Glu Lys Gln Val Val Asp Arg
130                 135                 140

Leu Asp Pro Ile Phe Ala Ala Leu Ala Pro Gly Ala Gly Asp Ile Pro
145                 150                 155                 160

Arg Thr Glu Gly Arg Glu Gly Arg Asp Pro Arg Ile Glu Gln Gly Tyr
                165                 170                 175

Ile His Ala Gly Pro Val Gly Ala Gly His Phe Val Lys Met Ile His
            180                 185                 190

Asn Gly Ile Glu Tyr Gly Leu Met Gln Ala Tyr Ala Glu Gly Phe Asp
        195                 200                 205

Ile Leu Lys Asn Ala Asn Ile Asp Ala Leu Pro Ala Asp His Arg Tyr
    210                 215                 220

Asp Phe Asp Leu Ala Asp Ile Ala Glu Val Trp Arg Arg Gly Ser Val
225                 230                 235                 240

Ile Pro Ser Trp Leu Leu Asp Leu Thr Ser Thr Ala Leu Ala Asp Ser
                245                 250                 255

Pro Ala Leu Ala Glu Tyr Ser Gly Phe Val Glu Asp Ser Gly Glu Gly
            260                 265                 270

Arg Trp Thr Val Asn Ala Ala Ile Asp Glu Ala Val Pro Ala Glu Val
        275                 280                 285
```

Leu Thr Ala Ala Leu Tyr Thr Arg Phe Arg Ser Arg Lys Glu His Thr
    290                 295                 300

Phe Ala Glu Lys Ile Leu Ser Ala Met Arg Ala Gly Phe Gly Gly His
305                 310                 315                 320

Lys Glu Pro Lys Gln Pro Gly Ala Ser Lys Pro Lys
                325                 330

<210> SEQ ID NO 7
<211> LENGTH: 789
<212> TYPE: DNA
<213> ORGANISM: Artificial Sequence
<220> FEATURE:
<223> OTHER INFORMATION: azf gene codon optimized

<400> SEQUENCE: 7
atggaccaac cagttttgtt gaccggtgct ggtggtagag ttggtcaagc tattttgggt      60
cacattggtg acgcttacga ctggagattg ttggacagag aaccattgtc tgacgaaaag     120
attccagact ctgttgactc taccgaagtt tacgttgctg acgttaccga cgaaaccgct     180
gttagaaacg ctatggacgg tgttcacgct gttattcact ggctggtga cccaagacca      240 gaagctccat gggactctgt tttgagaaac aacattgacg gtacccaaca aatgttcgac     300
gctgctgttg acgttggtgt tgaaaagttc gctttcgctt cttctaacca cgctgttggt     360
gcttacgaaa ccaccgacag aaccccagac atgtacagac acaccacga attcagattg      420 gacggtaccg aattgccaag accatctaac ttgtacggtg tttctaaggc tgctggtgaa     480 acctgggta gatactacca cgaccaccac gacatttctg ttgttaacgt tagaattggt      540
aacttgaccc aacaccaccc accaaaggaa tacgaaagag gtcaagctat gttgtct       600 tacagagact gtggtcactt gttcgaatgt tgtattgaag ctgactacga ctacgaaatt     660
gtttacggta tttctgacaa cgacagaaag tactactcta ttgacagagc tagagctgtt     720
ttgggttacg acccacaaga caactctgct gaattcacct tcgaaggtga accattggac     780
gaagcttaa                                                              789

<210> SEQ ID NO 8
<211> LENGTH: 262
<212> TYPE: PRT
<213> ORGANISM: Artificial Sequence
<220> FEATURE:
<223> OTHER INFORMATION: azf protein (ADEE03728.1, Haloferax volcanii)

<400> SEQUENCE: 8

Met Asp Gln Pro Val Leu Leu Thr Gly Ala Gly Gly Arg Val Gly Gln
1               5                   10                  15

Ala Ile Leu Gly His Ile Gly Asp Ala Tyr Asp Trp Arg Leu Leu Asp
            20                  25                  30

Arg Glu Pro Leu Ser Asp Glu Lys Ile Pro Asp Ser Val Asp Ser Thr
        35                  40                  45

Glu Val Tyr Val Ala Asp Val Thr Asp Glu Thr Ala Val Arg Asn Ala
    50                  55                  60

Met Asp Gly Val His Ala Val Ile His Leu Ala Gly Asp Pro Arg Pro
65                  70                  75                  80

Glu Ala Pro Trp Asp Ser Val Leu Arg Asn Asn Ile Asp Gly Thr Gln
                85                  90                  95

Gln Met Phe Asp Ala Ala Val Asp Val Gly Val Glu Lys Phe Ala Phe
            100                 105                 110

```
Ala Ser Ser Asn His Ala Val Gly Ala Tyr Glu Thr Thr Asp Arg Thr
            115                 120                 125

Pro Asp Met Tyr Arg Pro His His Glu Phe Arg Leu Asp Gly Thr Glu
        130                 135                 140

Leu Pro Arg Pro Ser Asn Leu Tyr Gly Val Ser Lys Ala Ala Gly Glu
145                 150                 155                 160

Thr Leu Gly Arg Tyr Tyr His Asp His His Asp Ile Ser Val Val Asn
                165                 170                 175

Val Arg Ile Gly Asn Leu Thr Gln His His Pro Lys Glu Tyr Glu
            180                 185                 190

Arg Gly Gln Ala Met Trp Leu Ser Tyr Arg Asp Cys Gly His Leu Phe
        195                 200                 205

Glu Cys Cys Ile Glu Ala Asp Tyr Asp Tyr Glu Ile Val Tyr Gly Ile
    210                 215                 220

Ser Asp Asn Asp Arg Lys Tyr Tyr Ser Ile Asp Arg Ala Arg Ala Val
225                 230                 235                 240

Leu Gly Tyr Asp Pro Gln Asp Asn Ser Ala Glu Phe Thr Phe Glu Gly
                245                 250                 255

Glu Pro Leu Asp Glu Ala
            260

<210> SEQ ID NO 9
<211> LENGTH: 2466
<212> TYPE: DNA
<213> ORGANISM: Artificial Sequence
<220> FEATURE:
<223> OTHER INFORMATION: eutE casette

<400> SEQUENCE: 9
gaattgtgag cggataacaa tttcacacag gaaacagcta tgaccatgat tacgccaagc      60
gcgcaattaa ccctcactaa agggaacaaa agctggagct cagtttatca ttatcaatac     120
tcgccatttc aaagaatacg taaataatta atagtagtga ttttcctaac tttatttagt     180
caaaaaatta gccttttaat tctgctgtaa cccgtacatg cccaaaatag ggggcgggtt     240
acacagaata tataacatcg taggtgtctg ggtgaacagt ttattcctgg catccactaa     300
atataatgga gcccgctttt aagctggca tccagaaaaa aaagaatcc cagcaccaaa      360 atattgtttt cttcaccaac catcagttca taggtccatt ctcttagcgc aactacagag     420
aacaggggca caaacaggca aaaacgggc acaacctcaa tggagtgatg caacctgcct     480
ggagtaaatg atgacacaag gcaattgacc cacgcatgta tctatctcat tttcttacac     540
cttctattac cttctgctct ctctgatttg gaaaaagctg aaaaaaaagg ttgaaaccag     600
ttccctgaaa ttattcccct acttgactaa taagtatata aagacggtag gtattgattg     660
taattctgta aatctatttc ttaaacttct taaattctac ttttatagtt agtctttttt     720
ttagttttaa acaccagaa cttagtttcg acggattcta gaactagtaa aaaatgaacc     780
aacaagatat cgaacaagtt gtcaaggctg tcttgttgaa aatgcaatct tctgacactc     840
catctgctgc tgtccacgaa atgggtgttt tcgcttcttt ggacgacgct gttgctgctg     900
ccaaggttgc tcaacaaggt ttgaaatctg ttgccatgag acaattggcc attgctgcca     960
tcagagaagc tggtgaaaag catgccagag acttggctga attggctgtc tccgaaaccg    1020
gtatgggtag agttgaagac aaattcgcta gaacgttgc tcaagctaga ggtactccag    1080
gtgtcgaatt tttgtctcca caagtcttga ccggtgataa tggttgact ttgattgaaa     1140 atgctccatg gggtgttgtt gcttccgtca ccccatctac caacccagct gctactgtca    1200
```

```
tcaacaacgc catctctttg attgctgctg gtaactccgt tatcttcgct ccacacccag    1260
ctgccaagaa ggtttctcaa agagccatca ctctattgaa ccaagccatt gttgctgctg    1320
gtggtccaga aaacttgttg gtcactgttg ccaacccaga tatcgaaact gctcaaagat    1380
tattcaagtt cccaggtatc ggtctattag tcgtcactgg tggtgaagct gttgttgaag    1440
ctgccagaaa gcacaccaac aagagattga ttgctgctgg tgctggtaac cctcctgttg    1500
ttgtcgatga aaccgctgat ttggccagag ctgctcaatc cattgtcaag ggtgcttctt    1560
tcgacaacaa catcatctgt gctgacgaaa aggttttgat tgttgttgac tccgttgctg    1620
acgaattgat gagattgatg gaaggtcaac atgccgtcaa gttgactgct gaacaagctc    1680
aacaattgca accagttttg ttgaagaaca tcgatgaaag aggtaagggt accgtctcca    1740
gagactgggt tggtagagat gctggtaaga ttgctgctgc catcggtttg aaggttccac    1800
aagaaaccag attattattc gtcgaaacca ccgctgaaca cccatttgct gtcactgaat    1860
tgatgatgcc agtcttacca gttgtccgtg ttgctaacgt tgctgacgct attgctttgg    1920
ctgtcaaatt ggaaggtggt tgtcaccaca ctgctgccat gcactccaga aacatcgaaa    1980
acatgaacca aatggctaac gccattgaca cttccatctt tgtcaagaac ggtccatgta    2040
tcgctggttt gggtttgggt ggtgaaggtt ggaccaccat gaccatcacc accccaactg    2100
gtgaaggtgt cacttctgcc agaactttcg tcagattacg tcgttgtgtt ttggtcgatg    2160 cttttcagaat tgtttaaact gcagtcgact cgagtcatgt aattagttat gtcacgctta    2220
cattcacgcc ctcccccccac atccgctcta accgaaaagg aaggagttag acaacctgaa    2280
gtctaggtcc ctatttattt ttttatagtt atgttagtat taagaacgtt atttatattt    2340 caaattttc ttttttttct gtacagacgc gtgtacgcat gtaacattat actgaaaacc    2400
ttgcttgaga aggttttggg acgctcgaag gctttaattt gcggccgctc tagaactagt    2460
ggatcc                                                              2466
```

<210> SEQ ID NO 10
<211> LENGTH: 20
<212> TYPE: DNA
<213> ORGANISM: Artificial Sequence
<220> FEATURE:
<223> OTHER INFORMATION: primer confirmation of GPD2 deletion

<400> SEQUENCE: 10
ccaaatgcga catgagtcac                                                  20

<210> SEQ ID NO 11
<211> LENGTH: 18
<212> TYPE: DNA
<213> ORGANISM: Artificial Sequence
<220> FEATURE:
<223> OTHER INFORMATION: primer confirmation of GPD2 deletion

<400> SEQUENCE: 11
acggacctat tgccattg                                                    18

<210> SEQ ID NO 12
<211> LENGTH: 20
<212> TYPE: DNA
<213> ORGANISM: Artificial Sequence
<220> FEATURE:
<223> OTHER INFORMATION: primer confirmation of GND1 deletion

<400> SEQUENCE: 12
cctgtttgcc tttccttacg                                          20

<210> SEQ ID NO 13
<211> LENGTH: 18
<212> TYPE: DNA
<213> ORGANISM: Artificial Sequence
<220> FEATURE:
<223> OTHER INFORMATION: primer confirmation of GND1 deletion

<400> SEQUENCE: 13
aaatgggcct gatgttcg                                            18

<210> SEQ ID NO 14
<211> LENGTH: 20
<212> TYPE: DNA
<213> ORGANISM: Artificial Sequence
<220> FEATURE:
<223> OTHER INFORMATION: primer confirmation of ALD6 deletion

<400> SEQUENCE: 14
atcccgggtg gaaactaaac                                          20

<210> SEQ ID NO 15
<211> LENGTH: 18
<212> TYPE: DNA
<213> ORGANISM: Artificial Sequence
<220> FEATURE:
<223> OTHER INFORMATION: primer confirmation of ALD6 deletion

<400> SEQUENCE: 15
aggcacaagc ctgttctc                                            18

<210> SEQ ID NO 16
<211> LENGTH: 20
<212> TYPE: DNA
<213> ORGANISM: Artificial Sequence
<220> FEATURE:
<223> OTHER INFORMATION: primer confirmation of GPD1 deletion

<400> SEQUENCE: 16
tcctcggtag atcaggtcag                                          20

<210> SEQ ID NO 17
<211> LENGTH: 20
<212> TYPE: DNA
<213> ORGANISM: Artificial Sequence
<220> FEATURE:
<223> OTHER INFORMATION: primer confirmation of GPD1 deletion

<400> SEQUENCE: 17
acggtgagct ccgtattatc                                          20

<210> SEQ ID NO 18
<211> LENGTH: 33
<212> TYPE: DNA
<213> ORGANISM: Artificial Sequence
<220> FEATURE:
<223> OTHER INFORMATION: Primer for Amplication of pMEL11 backbone

<400> SEQUENCE: 18
gttttagagc tagaaatagc aagttaaaat aag                           33

<210> SEQ ID NO 19
<211> LENGTH: 24
<212> TYPE: DNA
<213> ORGANISM: Artificial Sequence

```
<220> FEATURE:
<223> OTHER INFORMATION: Primer for Amplication of pROS11 backbone

<400> SEQUENCE: 19
gatcatttat ctttcactgc ggag                                          24

<210> SEQ ID NO 20
<211> LENGTH: 20
<212> TYPE: DNA
<213> ORGANISM: Artificial Sequence
<220> FEATURE:
<223> OTHER INFORMATION: Primer for Amplication of pMEL11 insert
      sequence

<400> SEQUENCE: 20
tattgacgcc gggcaagagc                                               20

<210> SEQ ID NO 21
<211> LENGTH: 17
<212> TYPE: DNA
<213> ORGANISM: Artificial Sequence
<220> FEATURE:
<223> OTHER INFORMATION: Primer for Amplication of pMEL11 backbone

<400> SEQUENCE: 21
cgaccgagtt gctcttg                                                  17

<210> SEQ ID NO 22
<211> LENGTH: 104
<212> TYPE: DNA
<213> ORGANISM: Artificial Sequence
<220> FEATURE:
<223> OTHER INFORMATION: Primer for Amplication of pROS11 insert
      sequence (GPD1 targeting)

<400> SEQUENCE: 22
gtgcgcatgt ttcggcgttc gaaacttctc cgcagtgaaa gataaatgat cgggcaagga   60
cgtcgaccat agttttagag ctagaaatag caagttaaaa taag                   104

<210> SEQ ID NO 23
<211> LENGTH: 104
<212> TYPE: DNA
<213> ORGANISM: Artificial Sequence
<220> FEATURE:
<223> OTHER INFORMATION: Primer for Amplication of pROS11 insert
      sequence (GPD2 targeting)

<400> SEQUENCE: 23
gtgcgcatgt ttcggcgttc gaaacttctc cgcagtgaaa gataaatgat cccaagaatt   60
cccattattc ggttttagag ctagaaatag caagttaaaa taag                   104

<210> SEQ ID NO 24
<211> LENGTH: 120
<212> TYPE: DNA
<213> ORGANISM: Artificial Sequence
<220> FEATURE:
<223> OTHER INFORMATION: Primer for Repair oligonucleotide (GPD1
      knockout)

<400> SEQUENCE: 24
tggtattggc agtttcgtag ttatatatat actaccatga gtgaaactgt tacgttacct   60
gcattatgtc atttctcata actactttat cacgttagaa attacttatt attattaaat  120

<210> SEQ ID NO 25
```

```
<211> LENGTH: 120
<212> TYPE: DNA
<213> ORGANISM: Artificial Sequence
<220> FEATURE:
<223> OTHER INFORMATION: Primer for Repair oligonucleotide (GPD1
      knockout)

<400> SEQUENCE: 25
atttaataat aataagtaat ttctaacgtg ataaagtagt tatgagaaat gacataatgc    60
aggtaacgta acagtttcac tcatggtagt atatatataa ctacgaaact gccaatacca   120

<210> SEQ ID NO 26
<211> LENGTH: 120
<212> TYPE: DNA
<213> ORGANISM: Artificial Sequence
<220> FEATURE:
<223> OTHER INFORMATION: Primer for Amplification of pMEL11 insert (GND2
      targeting)

<400> SEQUENCE: 26
gttgataacg gactagcctt attttaactt gctatttcta gctctaaaac tatgatctgg    60
cagcttcgcg gatcatttat ctttcactgc ggagaagttt cgaacgccga aacatgcgca   120

<210> SEQ ID NO 27
<211> LENGTH: 20
<212> TYPE: DNA
<213> ORGANISM: Artificial Sequence
<220> FEATURE:
<223> OTHER INFORMATION: Primer for Confirmation of GND2 deletion

<400> SEQUENCE: 27
tctgacaggt ggcagtttcc                                                20

<210> SEQ ID NO 28
<211> LENGTH: 20
<212> TYPE: DNA
<213> ORGANISM: Artificial Sequence
<220> FEATURE:
<223> OTHER INFORMATION: Primer for Confirmation of GND2 deletion

<400> SEQUENCE: 28
atccgaaagg cggcaatagg                                                20

<210> SEQ ID NO 29
<211> LENGTH: 120
<212> TYPE: DNA
<213> ORGANISM: Artificial Sequence
<220> FEATURE:
<223> OTHER INFORMATION: Primer for Repair oligonucleotide (GND2
      knockout)

<400> SEQUENCE: 29
aagaattcgt aggtgcaggt gagcatattg ccggataagt gtagttacgc aactacaatt    60
gttactaagg cccaatccgg ttggagaaga actattgccc ttgctgctac ttacggtatt   120

<210> SEQ ID NO 30
<211> LENGTH: 120
<212> TYPE: DNA
<213> ORGANISM: Artificial Sequence
<220> FEATURE:
<223> OTHER INFORMATION: Primer for Repair oligonucleotide (GND2
      knockout)

<400> SEQUENCE: 30
aataccgtaa gtagcagcaa gggcaatagt tcttctccaa ccggattggg ccttagtaac    60
```

```
aattgtagtt gcgtaactac acttatccgg caatatgctc acctgcacct acgaattctt    120

<210> SEQ ID NO 31
<211> LENGTH: 120
<212> TYPE: DNA
<213> ORGANISM: Artificial Sequence
<220> FEATURE:
<223> OTHER INFORMATION: Primer for Amplification of pMEL11 insert (GND1
      targeting)

<400> SEQUENCE: 31
gttgataacg gactagcctt attttaactt gctatttcta gctctaaaac tcggatttag    60
cagagatgga gatcatttat ctttcactgc ggagaagttt cgaacgccga acatgcgca    120

<210> SEQ ID NO 32
<211> LENGTH: 79
<212> TYPE: DNA
<213> ORGANISM: Artificial Sequence
<220> FEATURE:
<223> OTHER INFORMATION: Primer for Amplification of integration
      cassette (gndA, 6pgdh, gox1705)

<400> SEQUENCE: 32
taaacctgta ttgttgccat tacagaaaaa agccactttc tatacaaaaa ctacaataaa    60
gcgataccct gcgatcttc                                                 79

<210> SEQ ID NO 33
<211> LENGTH: 78
<212> TYPE: DNA
<213> ORGANISM: Artificial Sequence
<220> FEATURE:
<223> OTHER INFORMATION: Primer for Amplification of integration
      cassette (gndA, 6pgdh, gox1705)

<400> SEQUENCE: 33
gatatggata tccttgtcta ctggcaagtt gtcagaagca cattctggca acactctgaa    60
cgcgcagatt agcgaagc                                                  78

<210> SEQ ID NO 34
<211> LENGTH: 20
<212> TYPE: DNA
<213> ORGANISM: Artificial Sequence
<220> FEATURE:
<223> OTHER INFORMATION: Primer for Confirmation of gndA integration

<400> SEQUENCE: 34
aagaagaggt gcttggttgg                                                20

<210> SEQ ID NO 35
<211> LENGTH: 20
<212> TYPE: DNA
<213> ORGANISM: Artificial Sequence
<220> FEATURE:
<223> OTHER INFORMATION: Primer for Confirmation of gndA integration

<400> SEQUENCE: 35
tccaaacctt cagcgaaagc                                                20

<210> SEQ ID NO 36
<211> LENGTH: 20
<212> TYPE: DNA
<213> ORGANISM: Artificial Sequence
<220> FEATURE:
<223> OTHER INFORMATION: Primer for Confirmation of 6pgdh integration
```

<400> SEQUENCE: 36
cgacgttaga agaggtaagg                                               20

<210> SEQ ID NO 37
<211> LENGTH: 20
<212> TYPE: DNA
<213> ORGANISM: Artificial Sequence
<220> FEATURE:
<223> OTHER INFORMATION: Primer for Confirmation of 6pgdh integration

<400> SEQUENCE: 37
ccttcggttc ttggaatgtc                                               20

<210> SEQ ID NO 38
<211> LENGTH: 20
<212> TYPE: DNA
<213> ORGANISM: Artificial Sequence
<220> FEATURE:
<223> OTHER INFORMATION: Primer for Confirmation of gox1705 integration

<400> SEQUENCE: 38
ggacgacgtt agaagatctg                                               20

<210> SEQ ID NO 39
<211> LENGTH: 20
<212> TYPE: DNA
<213> ORGANISM: Artificial Sequence
<220> FEATURE:
<223> OTHER INFORMATION: Primer for Confirmation of gox1705 integration

<400> SEQUENCE: 39
gtattcagcg gtttccttgg                                               20

<210> SEQ ID NO 40
<211> LENGTH: 120
<212> TYPE: DNA
<213> ORGANISM: Artificial Sequence
<220> FEATURE:
<223> OTHER INFORMATION: Primer for Repair oligonucleotide (ALD6
      knockout)

<400> SEQUENCE: 40
tagaagaaaa aacatcaaga aacatcttta acatacacaa acacatacta tcagaataca    60
tgtaccaacc tgcatttctt tccgtcatat acacaaaata ctttcatata aacttacttg   120

<210> SEQ ID NO 41
<211> LENGTH: 120
<212> TYPE: DNA
<213> ORGANISM: Artificial Sequence
<220> FEATURE:
<223> OTHER INFORMATION: Repair oligonucleotide (ALD6 knockout)

<400> SEQUENCE: 41
caagtaagtt tatatgaaag tattttgtgt atatgacgga agaaatgca ggttggtaca     60 tgtattctga tagtatgtgt ttgtgtatgt taaagatgtt tcttgatgtt ttttcttcta   120

<210> SEQ ID NO 42
<211> LENGTH: 120
<212> TYPE: DNA
<213> ORGANISM: Artificial Sequence
<220> FEATURE:
<223> OTHER INFORMATION: Primer for Amplification of pMEL11 insert (ALD6
      targeting)

```
<400> SEQUENCE: 42
gttgataacg gactagcctt attttaactt gctatttcta gctctaaaac aattcagagc        60
tgttagccat gatcatttat ctttcactgc ggagaagttt cgaacgccga acatgcgca       120

<210> SEQ ID NO 43
<211> LENGTH: 80
<212> TYPE: DNA
<213> ORGANISM: Artificial Sequence
<220> FEATURE:
<223> OTHER INFORMATION: Primer for Amplification of integration
      cassette (eutE)

<400> SEQUENCE: 43
gtattttggt agattcaatt ctctttccct ttccttttcc ttcgctcccc ttccttatca        60
cacaggaaac agctatgacc                                                  80

<210> SEQ ID NO 44
<211> LENGTH: 80
<212> TYPE: DNA
<213> ORGANISM: Artificial Sequence
<220> FEATURE:
<223> OTHER INFORMATION: Primer for Amplification of integration
      cassette (eutE)

<400> SEQUENCE: 44
ataactgtag taatgttact agtagtagtt gtagaacttg tgtataatga taaattggtt       60
gccgcaaatt aaagccttcg                                                  80

<210> SEQ ID NO 45
<211> LENGTH: 20
<212> TYPE: DNA
<213> ORGANISM: Artificial Sequence
<220> FEATURE:
<223> OTHER INFORMATION: Primer for Confirmation of eutE integration

<400> SEQUENCE: 45
cgaacaagtt gtcaaggctg                                                  20

<210> SEQ ID NO 46
<211> LENGTH: 20
<212> TYPE: DNA
<213> ORGANISM: Artificial Sequence
<220> FEATURE:
<223> OTHER INFORMATION: Primer for Confirmation of eutE integration

<400> SEQUENCE: 46
gcatcgacca aaacacaacg                                                  20

<210> SEQ ID NO 47
<211> LENGTH: 464
<212> TYPE: PRT
<213> ORGANISM: Escherichia coli
<220> FEATURE:
<221> NAME/KEY: MISC_FEATURE
<222> LOCATION: (1)..(464)
<223> OTHER INFORMATION: Amino acid sequence of E.coli oxidoreductase of
      (Escherichia coli eutE)

<400> SEQUENCE: 47

Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
            20                  25                  30
```

```
Phe Ala Ser Leu Asp Asp Ala Val Ala Ala Lys Val Ala Gln Gln
            35                  40                  45

Gly Leu Lys Ser Val Ala Met Arg Gln Leu Ala Ile Ala Ala Ile Arg
 50                  55                  60

Glu Ala Gly Glu Lys His Ala Arg Asp Leu Ala Glu Leu Ala Val Ser
 65                  70                  75                  80

Glu Thr Gly Met Gly Arg Val Glu Asp Lys Phe Ala Lys Asn Val Ala
                 85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Gly Gln His Ala Val Lys Leu Thr Ala Glu Gln Ala Gln Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
    370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
```

<210> SEQ ID NO 48
<211> LENGTH: 366
<212> TYPE: PRT
<213> ORGANISM: Escherichia coli
<220> FEATURE:
<221> NAME/KEY: MISC_FEATURE
<222> LOCATION: (1)..(366)
<223> OTHER INFORMATION: Amino acid sequence of E.coli glycerol
      dehydrogenase ((Escherichia coli gldA)

<400> SEQUENCE: 48

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Thr Gln Ala Ala Leu Ala Leu Ala Glu Leu Cys Tyr Asn Thr
        195                 200                 205

Leu Leu Glu Glu Gly Glu Lys Ala Met Leu Ala Ala Glu Gln His Val
    210                 215                 220

Val Thr Pro Ala Leu Glu Arg Val Ile Glu Ala Asn Thr Tyr Leu Ser
225                 230                 235                 240

Gly Val Gly Phe Glu Ser Gly Gly Leu Ala Ala Ala His Ala Val His
                245                 250                 255

Asn Gly Leu Thr Ala Ile Pro Asp Ala His His Tyr Tyr His Gly Glu
            260                 265                 270

Lys Val Ala Phe Gly Thr Leu Thr Gln Leu Val Leu Glu Asn Ala Pro
        275                 280                 285

Val Glu Glu Ile Glu Thr Val Ala Ala Leu Ser His Ala Val Gly Leu
    290                 295                 300

Pro Ile Thr Leu Ala Gln Leu Asp Ile Lys Glu Asp Val Pro Ala Lys
305                 310                 315                 320

Met Arg Ile Val Ala Glu Ala Ala Cys Ala Glu Gly Glu Thr Ile His
                325                 330                 335

Asn Met Pro Gly Gly Ala Thr Pro Asp Gln Val Tyr Ala Ala Leu Leu

```
              340                 345                 350
Val Ala Asp Gln Tyr Gly Gln Arg Phe Leu Gln Glu Trp Glu
      355                 360                 365
```

<210> SEQ ID NO 49
<211> LENGTH: 912
<212> TYPE: DNA
<213> ORGANISM: Methylobacillus flagellatus
<220> FEATURE:
<221> NAME/KEY: misc_feature
<222> LOCATION: (1)..(912)
<223> OTHER INFORMATION: Nucleotide sequence of gndA (6-phosphoglucanate dehydrogenase

<400> SEQUENCE: 49

```
atgaagttgg ctattattgg tttgggtaag atgggtggta acatggctag aagattgttg      60
aagcacggta ttgaagttgt tggtttcgac ttcaaccaag acgctgttaa ccaaatttct     120
ttgaccaacg gtatgattcc agcttcttct gttgaagacg ctgtttctaa gttgtctggt     180
gaaccaagaa agattgtttg gattatgttg ccatctggtg acattaccga aaaccaaatt     240
aaggacttgg ttccattgtt gtctaagggt gacattattg ttgacggtgg taactctaac     300
tacaagcact ctcaaagaag aggtgcttgg ttggctgaac acggtattga attcattgac     360
tgtggtacct ctggtggtat ttggggtttg acaacggtt actgtttgat gtacggtggt     420
tctaaggacg ctgctgacgc tgttgttcca attatgcaag ctttggctca cgctgacaga     480
ggttgggctc acgttggtcc agttggttct ggtcacttca ccaagatgat tcacaacggt     540
attgaatacg gtatgatgca gctttcgct gaaggtttgg acttgttgaa gggtaaggaa     600
gaattcaact ggacttggc tcaaattacc gaattgtgga cacggttc tgttgttaga     660 tcttggttgt tggacttgac cgctgaagct ttggctcacg accaagaatt gtctgctatt     720
gctccatacg ttgctgactc tggtgaaggt agatggaccg ttgttgaagc tgttgaccaa     780
ggtgttgctg ctccagtttt gaccttggct ttgcaaatga attcgcttc tcaagaagac     840 accggttact cttacaagtt gttgtctatg atgagaaacg ctttcggtgg tcacgctgtt     900
aagaccaagt aa                                                        912
```

<210> SEQ ID NO 50
<211> LENGTH: 999
<212> TYPE: DNA
<213> ORGANISM: Gluconobacter oxydans
<220> FEATURE:
<221> NAME/KEY: misc_feature
<222> LOCATION: (1)..(999)
<223> OTHER INFORMATION: Nucleotide sequence of gox1705 (6-phosphoglucanate dehydrogenase

<400> SEQUENCE: 50

```
atgagaattg gtattattgg tttgggtaga atgggtggta acattgctgt tagattgacc      60
agacacggtc acgacgttgt tgttcacgac agaacctctg aagttaccac ctctgttgtt     120
ggtagatgtg aagctggtag agctacccca gctgacacct ggctgacat ggctaagttg     180 ttggaaggtg acgaacacag agttgtttgg gttatgttgc cagctggtgc tattaccgaa     240
gactgtgttc aacaattggg tggtttgttg gtagaggtg acattattat tgacggtggt     300
aacacctact acaaggacga cgttagaaga tctgctgaat ggctgaaaaa gggtatttct     360
tacgttgacg ttggtacctc tggtggtgtt tggggtttgg aaagaggtta ctgtatgatg     420
ttcggtggta ccaaggaaac cgctgaatac attgacccaa tttgtctgc tttggctcca     480
```

| ggtattggtg acgttccaag aacccagggt agagacgaag ctggtcacga cccaagagct | 540 |
| gaacaaggtt acttgcactg tggtccagct ggttctggtc acttcgttaa gatggttcac | 600 |
| aacggtattg aatacggtat gatgcaagct ttcgctgaag gtttcgacat tatgaagtct | 660 |
| aagaactctc caattttggc tgaaaaggac agattcgaat tgaacatggg tgacattgct | 720 |
| gaagtttgga gaagaggttc tgttgtttct tcttggttgt tggacttgac cgctgaagct | 780 |
| ttgaccagat ctgaaacctt gaacgaattc tctggtgaag ttgctgactc tggtgaaggt | 840 |
| agatggacca ttgaagctgc tattgaagaa gacgttccag ctccagttat gaccgctgct | 900 |
| ttgttcacca gattcagatc tagatctggt aacaacttcg ctgaaaagat tttgtctgct | 960 |
| caaagattcg gtttcggtgg tcacgttgaa aagaagtaa | 999 |

```
<210> SEQ ID NO 51
<211> LENGTH: 999
<212> TYPE: DNA
<213> ORGANISM: Bradyrhizobium sp.
<220> FEATURE:
<221> NAME/KEY: misc_feature
<222> LOCATION: (1)..(999)
<223> OTHER INFORMATION: Nucleotide sequence of 6pgdh
      (6-phosphoglucanate dehydrogenase

<400> SEQUENCE: 51
```

| atgcaattgg gtatgattgg tttgggtaga atgggtggta acattgttag aagattgatg | 60 |
| agacacggtc actctaccgt tgtttacgac aaggacgcta aggctgttgc tggtttggct | 120 |
| gctgacggtg ctgttggttc tgctaccttg gaagaattcg ttgctaagtt ggaaagacca | 180 |
| agaaccgctt gggttatgtt gccagctggt agaattaccg aaaccaccat tgacaccatt | 240 |
| gctggtgtta tgcaagaagg tgacgttatt attgacggtg gtaacacctt ctggcaagac | 300 |
| gacgttagaa gaggtaaggc tttgaaggct agaggtattc actacgttga cgttggtacc | 360 |
| tctggtggtg tttgggggttt ggacagaggt tactgtatga tgattggtgg tgaaaagcaa | 420 |
| gttgttgaca gattggaccc aattttcgct gctttggctc aggtgctggt gacattcca | 480 |
| agaaccgaag gtagagaagg tagagaccca agaattgaac aaggttacat tcacgctggt | 540 |
| ccagttggtg ctggtcactt cgttaagatg attcacaacg gtattgaata cggtttgatg | 600 |
| caagcttacg ctgaaggttt cgacattttg aagaacgcta acattgacgc tttgccagct | 660 |
| gaccacagat acgacttcga cttggctgac attgctgaag tttggagaag aggttctgtt | 720 |
| attccatctt ggttgttgga cttgacctct accgctttgg ctgactctcc agctttggct | 780 |
| gaatactctg tttcgttga agactctggt gaaggtagat ggaccgttaa cgctgctatt | 840 |
| gacgaagctg ttccagctga gttttgacc gctgctttgt acaccagatt cagatctaga | 900 |
| aaggaacaca ccttcgctga aaagattttg tctgctatga gagctggttt cggtggtcac | 960 |
| aaggaaccaa agcaaccagg tgcttctaag ccaaagtaa | 999 |

```
<210> SEQ ID NO 52
<211> LENGTH: 789
<212> TYPE: DNA
<213> ORGANISM: Haloferax volcanii
<220> FEATURE:
<221> NAME/KEY: misc_feature
<222> LOCATION: (1)..(789)
<223> OTHER INFORMATION: Nucleotide sequence of azf (glucose-
      6-phosphate dehydrogenase

<400> SEQUENCE: 52
```

| atggaccaac cagttttgtt gaccggtgct ggtggtagag ttggtcaagc tatttttgggt | 60 |

| | |
|---|---|
| cacattggtg acgcttacga ctggagattg ttggacagag aaccattgtc tgacgaaaag | 120 |
| attccagact ctgttgactc taccgaagtt tacgttgctg acgttaccga cgaaaccgct | 180 |
| gttagaaacg ctatggacgg tgttcacgct gttattcact ggctggtga cccaagacca | 240 |
| gaagctccat gggactctgt tttgagaaac aacattgacg tacccaaca aatgttcgac | 300 |
| gctgctgttg acgttggtgt tgaaaagttc gctttcgctt cttctaacca cgctgttggt | 360 |
| gcttacgaaa ccaccgacag aaccccagac atgtacagac acaccacga attcagattg | 420 |
| gacggtaccg aattgccaag accatctaac ttgtacggtg tttctaaggc tgctggtgaa | 480 |
| accttgggta gatactacca cgaccaccac gacatttctg ttgttaacgt tagaattggt | 540 |
| aacttgaccc aacaccaccc accaaaggaa tacgaaagag gtcaagctat gtggttgtct | 600 |
| tacagagact gtggtcactt gttcgaatgt tgtattgaag ctgactacga ctacgaaatt | 660 |
| gtttacggta tttctgacaa cgacagaaag tactactcta ttgacagagc tagagctgtt | 720 |
| ttgggttacg acccacaaga caactctgct gaattcacct tcgaaggtga accattggac | 780 |
| gaagcttaa | 789 |

<210> SEQ ID NO 53
<211> LENGTH: 1404
<212> TYPE: DNA
<213> ORGANISM: Escherichia coli
<220> FEATURE:
<221> NAME/KEY: misc_feature
<222> LOCATION: (1)..(1404)
<223> OTHER INFORMATION: Nucleotide sequence eutE (Acetylating
      acetaldehyde dehydrogenase

<400> SEQUENCE: 53

| | |
|---|---|
| atgaaccaac aagatatcga acaagttgtc aaggctgtct tgttgaaaat gcaatcttct | 60 |
| gacactccat ctgctgctgt ccacgaaatg ggtgttttcg cttctttgga cgacgctgtt | 120 |
| gctgctgcca aggttgctca acaaggtttg aaatctgttg ccatgagaca attggccatt | 180 |
| gctgccatca gagaagctgg tgaaaagcat gccagagact ggctgaatt ggctgtctcc | 240 |
| gaaaccggta tgggtagagt tgaagacaaa ttcgctaaga acgttgctca agctagaggt | 300 |
| actccaggtg tcgaatgttt gtctccacaa gtcttgaccg tgataatgg tttgactttg | 360 |
| attgaaaatg ctccatgggg tgttgttgct tccgtcaccc catctaccaa cccagctgct | 420 |
| actgtcatca caacgccat ctctttgatt gctgctggta actccgttat cttcgctcca | 480 |
| cacccagctc caagaaggt ttctcaaaga gccatcactc tattgaacca agccattgtt | 540 |
| gctgctggtg gtccagaaaa cttgttggtc actgttgcca acccagatat cgaaactgct | 600 |
| caaagattat tcaagttccc aggtatcggt ctattagtcg tcactggtgg tgaagctgtt | 660 |
| gttgaagctg ccagaaagca caccaacaag agattgattg ctgctggtgc tggtaaccct | 720 |
| cctgttgttg tcgatgaaac cgctgatttg gccagagctg ctcaatccat tgtcaagggt | 780 |
| gcttctttcg acaacaacat catctgtgct gacgaaaagg ttttgattgt tgttgactcc | 840 |
| gttgctgacg aattgatgag attgatggaa ggtcaacatg ccgtcaagtt gactgctgaa | 900 |
| caagctcaac aattgcaacc agttttgttg aagaacatcg atgaaagagg taagggtacc | 960 |
| gtctccagag actgggttgg tagagatgct ggtaagattg ctgctgccat cggtttgaag | 1020 |
| gttccacaag aaaccagatt attattcgtc gaaaccaccg ctgaacaccc atttgctgtc | 1080 |
| actgaattga tgatgccagt cttaccagtt gtccgtgttg ctaacgttgc tgacgctatt | 1140 |
| gctttggctg tcaaattgga aggtggttgt caccacactg ctgccatgca ctccagaaac | 1200 |

```
atcgaaaaca tgaaccaaat ggctaacgcc attgacactt ccatctttgt caagaacggt    1260
ccatgtatcg ctggtttggg tttgggtggt gaaggttgga ccaccatgac catcaccacc    1320
ccaactggtg aaggtgtcac ttctgccaga actttcgtca gattacgtcg ttgtgttttg    1380
gtcgatgctt tcagaattgt ttaa                                           1404
```

EUKARYOTIC CELL WITH INCREASED PRODUCTION OF FERMENTATION PRODUCT

CROSS-REFERENCE TO RELATED APPLICATIONS

This application is a National Stage entry of International Application No. PCT/EP2016/073561, filed 3 Oct. 2016, which claims priority to European Patent Application No. 15188645.4, filed 6 Oct. 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2919208-471000 Sequence Listing ST25.txt" created on 3 Oct. 2016, and 46,943 bytes in size) is submitted concurrently with the instant application, and the entire contents of the Sequence Listing are incorporated herein by reference.

FIELD

The present invention relates to a eukaryotic cell with increased production of fermentation product. In particular the invention relates to acetic acid, pentose and glucose converting eukaryotic cells with improved acetate conversion. The invention further relates to the processes wherein the cells produce fermentation products such as ethanol.

BACKGROUND

Second generation bioethanol is produced from e.g. lignocellulosic fractions of plant biomass that is hydrolyzed into free monomeric sugars, such as hexoses and pentoses, for fermentation into ethanol. Apart from the sugar release during pretreatment and hydrolysis of the biomass, some toxic by-products are formed. For instance, furfural and HMF are two of these products. The quantities in which they are formed depend on several pretreatment parameters, such as temperature, pressure and pretreatment time. Lignocellulosic hydrolysates also contain high amounts of acetic acid, which is a potent inhibitor of the fermentative capacity of microorganisms, such as eukaryotic cells.

Several different approaches have been reported that could help to reduce the inhibitory effect of acetic acid on the fermentation of the sugars in hydrolysates as well as (partly) solving redox balance issues upon deletion of the genes involved in glycerol production, e.g. by genetic engineering of eukaryotic cells. Acetic acid, along with other inhibitors, can be removed from hydrolysates through chemical or biological detoxification procedures. Additional detoxification steps after pre-treatment though are costly and/or cause a loss of fermentable substrate.

Under anaerobic conditions, *Saccharomyces cerevisiae* cannot naturally consume acetic acid. Furthermore, acetic acid tolerance seems to vary considerably between different strains. Past research has mainly been focused on the identification of potential gene candidates associated with increased tolerance and on the generation of strains with increased robustness through the use metabolic/evolutionary engineering approaches. However, the concept of generating detoxifying strains through the expression of heterologous enzymes has not been sufficiently explored.

Medina et al. 2010 describes expression of mhpF from *E. coli*, encoding for a $NAD^+$-dependent acetylating acetaldehyde dehydrogenase, enabled anaerobic growth of a gpd1Δ gpd2Δ strain by coupling the reduction of acetate to acetaldehyde with $NAD^+$ regeneration This approach completely abolished the formation of glycerol and resulted in an increase of 13% of the ethanol yield on sugar, caused mainly by the minimization of carbon losses for production of glycerol and the reduction of acetic acid to ethanol. An important additional benefit of this strategy is that it enables the in situ detoxification of acetic acid by the yeast. However, the amount of acetic acid that can be reduced in this way is limited by the amount of NADH that is generated during anabolism, which is coupled to biomass formation. Therefore there is still a need to improve the conversion of acetate, pentose and/or hexose to fermentation product.

DESCRIPTION OF RELATED ART

It is therefore an object of the present invention to provide for eukaryotic cells that are capable of producing ethanol from acetic acid or acetate while retaining their abilities of fermenting hexoses (glucose, fructose, galactose, etc.) as well as pentoses like xylose, as well as processes wherein these strains are used for the production of ethanol and/or other fermentation products.

Another object is to provide for cells, e.g. eukaryotic cells that are capable of producing ethanol from glycerol and/or glycerol and acetic acid while retaining their abilities of fermenting hexoses (glucose, fructose, galactose, etc.) as well as pentoses like xylose. Another object is to increase the production of fermentation product (yield, production rate or both). In an embodiment thereof the eukaryotic cell produces less glycerol.

Further, it is an object of the invention to provide a eukaryotic cell strain that can an-aerobically co-ferment acetate, pentose and glucose.

It is an object of the present invention to provide a cost-effective method of producing ethanol by fermentation of pentose and/or acetate.

It is another object of the present invention to provide a eukaryotic cell that is capable of fermenting pentose at a higher rate than can be achieved using strains currently known to the art.

It is another object to reduce the fermentation time.

It is another object to increase the yield of the fermentation.

Other objects, features, and advantages of the invention will be apparent from review of the specification and claims.

One or more of these objects are attained according to the invention that provides a eukaryotic cell that is genetically modified comprising one or more heterologous gene encoding:
a) D-glucose-6-phosphate dehydrogenase;
b) 6-phosphogluconate dehydrogenase and/or
c) glucose dehydrogenase, gluconolactonase and gluconate kinase,
wherein a), b) and the glucose dehydrogenase in c) are $NAD^+$ dependent.

According to the invention the cytosolic NADH level in the eukaryotic cell may be increased. This can lead in one embodiment to an improved yield of glycerol, which is advantageous in the wine industry. It o may, in a second embodiment, result in increased reduction of acetate level and/or increased yield of fermentation product, e.g. ethanol, that is advantageous in the biofuel industry. In an third embodiment, in particular when both a) and b) are $NAD^+$ dependent, the NADH generated may be used in the production of any fermentation product in the eukaryotic cell, wherein NADH in the cytosol acts as reducing co-factor. In a third embodiment, the NADH generated may be used in the production of any fermentation product in the eukaryotic cell, wherein NADH in the cytosol acts as reducing co-factor. These advantages are detailed herein below.

In one embodiment of the invention, the eukaryotic cell comprises a gene encoding $NAD^+$ dependent D-glucose-6-phosphate dehydrogenase a) (in that embodiment the 6-phosphogluconate dehydrogenase may still be NADP+ dependent). In another embodiment of the invention, the eukaryotic cell comprises a gene encoding $NAD^+$ dependent 6-phosphogluconate dehydrogenase (b) (in that embodiment the D-glucose-6-phosphate dehydrogenase may still be $NADP^+$ dependent). In one embodiment, the eukaryotic cell comprises a genes encoding for both (a) and (b), i.e. both $NAD^+$ dependent D-glucose-6-phosphate dehydrogenase (a) and $NAD^+$ dependent 6-phosphogluconate dehydrogenase (b). The embodiments a) and b) generate cytosolic NADH. In an embodiment the cell comprises c) glucose dehydrogenase, gluconolactonase and gluconate kinase. These three enzymes form another pathway from glucose to 6-phosphate-gluconate than that in which (a) or (b) is involved, but which also generates NADH, since glucose dehydrogenase in (c) is $NAD^+$ dependent. Embodiment (c) may be combined with embodiments (a) and/or (b).

Thus, in an embodiment the eukaryotic cell has a disruption of one or more native gene encoding D-glucose-6-phosphate dehydrogenase and/or native gene encoding 6-phosphogluconate dehydrogenase, wherein native is native in the eukaryotic cell.

In an embodiment D-glucose-6-phosphate dehydrogenase native in the eukaryotic cell is replaced by the $NAD^+$ dependent D-glucose-6-phosphate dehydrogenase and/or the 6-phosphogluconate dehydrogenase native in the eukaryotic cell is replaced by the $NAD^+$ dependent 6-phosphogluconate dehydrogenase. In that way the co-factor of these enzymes is advantageously modified. A change of co-factor dependency/specificity may be called herein "co-factor engineering".

The eukaryotic cells according to the invention, with heterologous gene(s) encoding:
a) D-glucose-6-phosphate dehydrogenase;
b) 6-phosphogluconate dehydrogenase; and/or
c) glucose dehydrogenase, gluconolactonase and gluconate kinase.
wherein a) and b) and glucose dehydrogenase in c) are $NAD^+$ dependent, produces more glycerol than the native strain (having both $NADP^+$ dependent D-glucose-6-phosphate dehydrogenase and $NADP^+$ dependent 6-phosphogluconate dehydrogenase). The strains produced that way are advantageous for application in the wine industry, since more glycerol may improve the taste of wine and at the same time the amount of ethanol may be reduced which is also desirable in the wine industry. These treats are obtained according to the invention with minimal effect on the fermentation of the wine yeast and wine production process. Alternatively the strains according to the invention are advantageously used in the biofuel industry, e.g. the bioethanol fuel industry.

In an embodiment, the NADH generated may be used in the production of any fermentation product, wherein NADH in the cytosol acts as reducing co-factor. This allows the production of fermentation products that would otherwise not be produced by the eukaryotic cells because of lack of NADH in the cytosol. Or it improves the yield in case the production of such fermentation product is limited by NADH level in the cytosol. In this embodiment it is advantageous, that both (a) D-glucose-6-phosphate dehydrogenase and (b) 6-phosphogluconate dehydrogenase are $NAD^+$ dependent, or even (a), (b) and (c1) glucose dehydrogenase are $NAD^+$ dependent. These embodiments allow the NADH-levels in the cytosol to be higher. Thus (a), (b) and (c1) create flexibility: It is possible for the skilled person, for each fermentation product and substrate, to convert a flexible part of the substrate to $CO_2$ and NADH in the cytosol, that is adapted to the need to produce the fermentation product in a high yield. In an embodiment the fermentation product that is a product that is more reduced than the substrate from which it is derived, for example glucose. Examples of suitable fermentation products that are more reduced than glucose is glycerol. The skilled person can determine the fermentation products which can be fermented that way. Such fermentation may be aerobic or anaerobic.

In an embodiment, the eukaryotic cell is genetically modified, comprising one or more heterologous gene encoding:
a) D-glucose-6-phosphate dehydrogenase and/or
b) 6-phosphogluconate dehydrogenase;
wherein a) and b) are $NAD^+$ dependent.

In an embodiment of the invention, wherein the eukaryotic cell comprises:
d) one or more nucleotide sequence encoding a heterologous $NAD^+$-dependent acetylating acetaldehyde dehydrogenase (E.C. 1.2.1.10);
e) one or more nucleotide sequence encoding a homologous or heterologous acetyl-CoA synthetase (E.C. 6.2.1.1); and optionally
g) a modification that leads to reduction of glycerol 3-phosphate phosphohydrolase (E.C. 3.1.3.21) and/or glycerol 3-phosphate dehydrogenase (E.C. 1.1.1.8 or E.C. 1.1.5.3) activity, native in the eukaryotic cell, the advantages of such strains according to the invention are increased consumption of acetate and increased production of fermentation product, e.g. ethanol.

Therefore the invention further relates to a process for the fermentation of a substrate to produce a fermentation product with the above eukaryotic cell, wherein the fermentation time is reduced and/or the yield increased, with simultaneous increased fermentation product output, relative to the corresponding fermentation with wild-type (as defined herein) eukaryotic cell.

FIG. 3A and FIG. 3B Fermentation shows fermentation profiles of IMX585 (FIG. 3A), IMX888 (FIG. 3D) and IMX860 (FIG. 3B). Glucose=filled circles, biomass=filled squares, glycerol=open squares, ethanol=open circles, acetate=triangles. Fermentations were performed in synthetic medium supplemented with 20 g L$^{-1}$ glucose and 3 g L$^{-1}$ acetic acid. Batches performed at pH 5, sparging of 500 ml min$^{-1}$ N2, 30° C. Biomass was calculated by converting OD values throughout the fermentation to biomass based on an OD to biomass conversion formula derived from plotting actual biomass samples against OD during mid-exponential phase. Ratio of acetate consumed per glucose consumed in anaerobic batch fermentations performed with IMX585, IMX888 and IMX860 is shown in FIG. 3C. Ratio of acetate consumed per biomass formed from the same fermentations is shown in FIG. 3E. Data is presented as averages of independent duplicate experiments.

Figure 4:
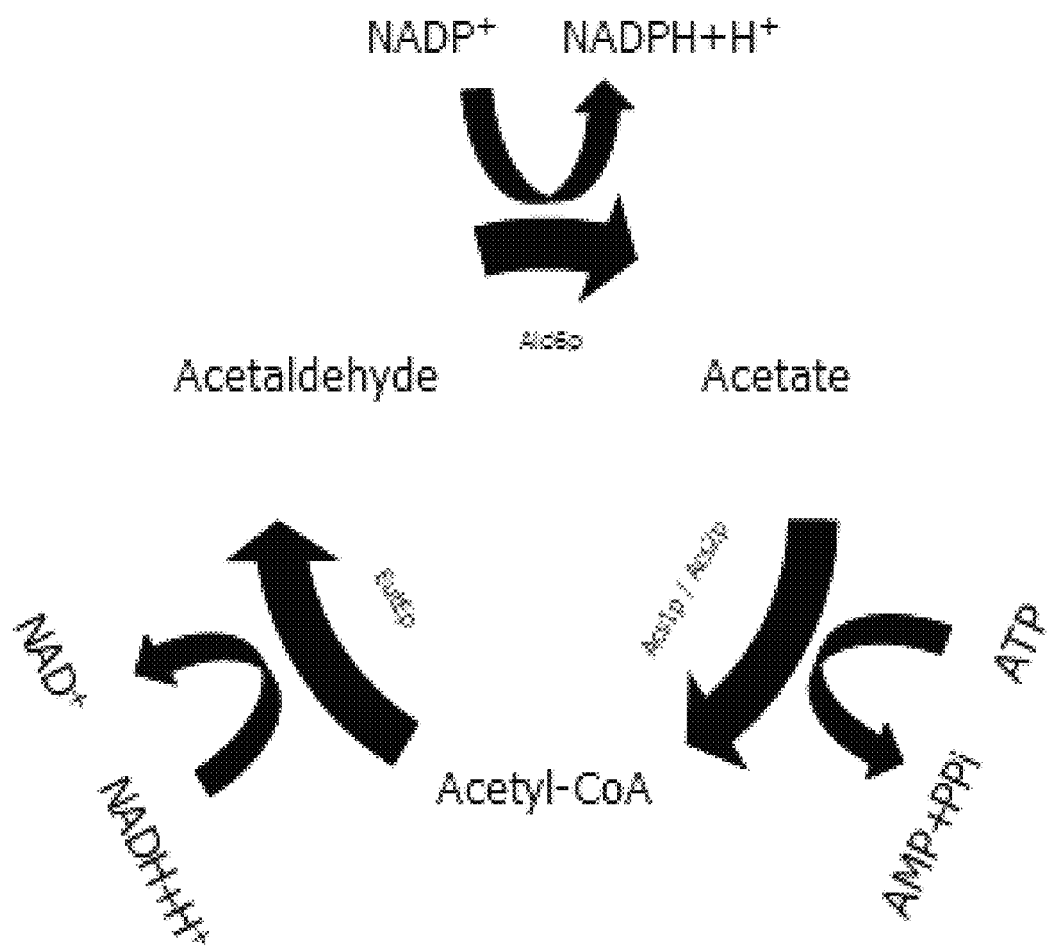

FIG. 4 shows ATP driven transhydrogenase-like cycle catalyzed by Acs1p/Acs2p, EutEp and Ald6p.

BRIEF DESCRIPTION OF THE SEQUENCE LISTING

SEQ ID NO: 1 Synthetic codon optimized gndA expression cassette;

SEQ ID NO: 2 GndA protein (*Methylobacillus flagellates*);

SEQ ID NO: 3 Synthetic codon optimized gox1705 expression cassette

SEQ ID NO: 4 Gox1705 protein (*Gluconobacter oxydans* 621H)

SEQ ID NO: 5 Synthetic codon optimized 6 pgdh expression cassette

SEQ ID NO: 6 6 pgdh protein WP_011089498.1 (Multi-species [*Bradyrhizobium*])

SEQ ID NO: 7 azf gene codon optimized

SEQ ID NO: 8 azf protein (ADEE03728.1, *Haloferax volcanii*)

SEQ ID NO: 9 eutE expression cassette

SEQ ID NO: 10 Primer confirmation of GPD2 deletion (Primer code: 2015)

SEQ ID NO: 11 Primer confirmation of GPD2 deletion (Primer code: 2112)

SEQ ID NO: 12 Primer confirmation of GND1 deletion (Primer code: 2123)

SEQ ID NO: 13 Primer confirmation of GND1 deletion (Primer code: 2124)

SEQ ID NO: 14 Primer confirmation of ALD6 deletion (Primer code: 2164)

SEQ ID NO: 15 Primer confirmation of ALD6 deletion (Primer code: 2171)

SEQ ID NO: 16 Primer confirmation of GPD1 deletion (Primer code: 4397)

SEQ ID NO: 17 Primer confirmation of GPD1 deletion (Primer code: 4401)

SEQ ID NO: 18 Primer for Amplication of pMEL11 backbone (Primer code: 5792)

SEQ ID NO: 19 Primer for Amplication of pROS11 backbone (Primer code: 5793)

SEQ ID NO: 20 Primer for Amplification of pMEL11 insert sequence (Primer code: 5979)

SEQ ID NO: 21 Primer for Amplication of pMEL11 backbone (Primer code: 5980)

SEQ ID NO: 22 Primer for Amplification of pROS11 insert sequence (GPD1 targeting) (Primer code: 6965)

SEQ ID NO: 23 Primer for Amplification of pROS11 insert sequence (GPD2 targeting) (Primer code: 6966)

SEQ ID NO: 24 Primer for Repair oligonucleotide (GPD1 knockout) (Primer code: 6967)

SEQ ID NO: 25 Primer for Repair oligonucleotide (GPD1 knockout) (Primer code: 6968)

SEQ ID NO: 26 Primer for Amplification of pMEL11 insert (GND2 targeting) (Primer code: 7231)

SEQ ID NO: 27 Primer for Confirmation of GND2 deletion (Primer code: 7258)

SEQ ID NO: 28 Primer for Confirmation of GND2 deletion (Primer code: 7259)

SEQ ID NO: 29 Primer for Repair oligonucleotide (GND2 knockout) (Primer code: 7299)

SEQ ID NO: 30 Primer for Repair oligonucleotide (GND2 knockout) (Primer code: 7300)

SEQ ID NO: 31 Primer for Amplification of pMEL11 insert (GND1 targeting) (Primer code: 7365)

SEQ ID NO: 32 Primer for Amplification of integration cassette (gndA, 6pgdh, gox1705) (Primer code: 7380)

SEQ ID NO: 33 Primer for Amplification of integration cassette (gndA, 6pgdh, gox1705) (Primer code: 7381)

SEQ ID NO: 34 Primer for Confirmation of gndA integration (Primer code: 7441)

SEQ ID NO: 35 Primer for Confirmation of gndA integration (Primer code: 7442)

SEQ ID NO: 36 Primer for Confirmation of 6pgdh integration (Primer code: 7443)

SEQ ID NO: 37 Primer for Confirmation of 6pgdh integration (Primer code: 7444)

SEQ ID NO: 38 Primer for Confirmation of gox1705 integration (Primer code: 7445)

SEQ ID NO: 39 Primer for Confirmation of gox1705 integration (Primer code: 7446)

SEQ ID NO: 40 Primer for Repair oligonucleotide (ALD6 knockout) (Primer code: 7608)

SEQ ID NO: 41 Repair oligonucleotide (ALD6 knockout) (Primer code: 7609)

SEQ ID NO: 42 Primer for Amplification of pMEL11 insert (ALD6 targeting) (Primer code: 7610)

SEQ ID NO: 43 Primer for Amplification of integration cassette (eutE) (Primer code: 7991)

SEQ ID NO: 44 Primer for Amplification of integration cassette (eutE) (Primer code: 7992)

SEQ ID NO: 45 Primer for Confirmation of eutE integration (Primer code: 8337)

SEQ ID NO: 46 Primer for Confirmation of eutE integration (Primer code: 8338)

SEQ ID NO: 47 Amino acid sequence of aldehyde oxidoreductase (*Escherichia coli* EutE); SEQ ID NO: 48 Amino acid sequence of glycerol dehydrogenase of *E. coli* (*Escherichia coli* gldA).

SEQ ID NO: 49 Nucleotide sequence of codon optimized gndA (6-phosphogluconate dehydrogenase) (*Methylobacillus flagellatus*)

SEQ ID NO: 50 Nucleotide sequence of codon optimized gox1705 (6-phosphogluconate dehydrogenase) (*Gluconobacter oxydans*)

SEQ ID NO: 51 Nucleotide sequence of codon optimized 6pgdh (6-phosphogluconate dehydrogenase) (*Bradyrhizobium* sp.)

SEQ ID NO: 52 Nucleotide sequence of codon optimized azf (glucose-6-phosphate dehydrogenase) (*Haloferax volcanii*)

SEQ ID NO: 53 Nucleotide sequence codon optimized eutE (*Acetylating acetaldehyde dehydrogenase*) (*E. coli*)

DETAILED DESCRIPTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element. By way of example, cell can herein be one cell, but refer also to a population of cells or a strain.

"Eukaryotic cell" is herein defined as any eukaryotic microorganism. Eukaryotes belong to the taxon Eukarya or Eukaryota. The defining feature that sets eukaryotic cells apart from prokaryotic cells (Bacteria and Archaea) is that they have membrane-bound organelles, especially the nucleus, which contains the genetic material, and is enclosed by the nuclear envelope. The presence of a nucleus gives eukaryotes their name, which comes from the Greek ευ (eu, "well") and κάpuov (karyon, "nut" or "kernel"). Eukaryotic cells also contain other membrane-bound organelles such as mitochondria and the Golgi apparatus. Many unicellular organisms are eukaryotes, such as protozoa and fungi. All multicellular organisms are eukaryotes. Unicellular eukaryotes consist of a single cell throughout their life cycle. Microbial eukaryotes can be either haploid or diploid. Preferably the eukaryotic cell is capable of anaerobic fermentation, more preferably anaerobic alcoholic fermentation.

"NAD⁺ dependent" is herein a protein specific characteristic described by the formula:

$$1 < K_m NADP^+/K_m NAD^+ < \infty \text{(infinity)}$$

NAD⁺ dependent is herein equivalent to NAD⁺ specific, NAD⁺ dependency is herein equivalent to NAD⁺ specificity. In an embodiment $K_m NADP^+/K_m NADP^+$ is between 1 and 1000, between 1 and 500, between 1 and 200, between 1 and 100, between 1 and 50, between 1 and 10, between 5 and 100, between 5 and 50, between 5 and 20 or between 5 and 10.

The $K_m$'s for the proteins (e.g. proteins a), b) and c1) in the claims) and is herein determined as protein specific, for NAD⁺ and NADP⁺ respectively, using know analysis techniques, calculations and protocols. These are described herein and for instance in Lodish et al., Molecular Cell Biology 6$^{th}$ Edition, Ed. Freeman, pages 80 and 81, e.g. FIG. 3-22.

"Sequence identity"

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences. An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P.

Longden,I. and Bleasby,A. Trends in Genetics 16, (6) pp276-277, For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to Met, leu or tyr; Ser to thr; Thr to ser; Trp to tyr; Tyr to trp or phe; and, Val to ile or leu.

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

A "nucleic acid construct" or "nucleic acid vector" is herein understood to mean a nucleic acid molecule designed by man resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or expression construct" refer to nucleotide sequences that are capable of affecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is continuously active under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

Yeasts are herein defined as eukaryotic microorganisms and include all species of the subdivision Eumycotina that predominantly grow in unicellular form. Yeasts may either grow by budding of a unicellular thallus or may grow by fission of the organism. Preferred yeasts cells for use in the present invention belong to the genera *Saccharomyces, Kluyveromyces, Candida, Pichia, Schizosaccharomyces, Hansenula, Kloeckera, Schwanniomyces*, and *Yarrowia*. Preferably the yeast is capable of anaerobic fermentation, more preferably anaerobic alcoholic fermentation.

"Fungi" (singular: fungus) are herein understood as heterotrophic eukaryotic microorganism that digest their food externally, absorbing nutrient molecules into their cells. Fungi are a separate kingdom of eukaryotic organisms and include yeasts, molds, and mushrooms. The terms fungi, fungus and fungal as used herein thus expressly includes yeasts as well as filamentous fungi.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'nontranslated sequence (3'end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. In this context, the use of only "homologous" sequence elements allows the construction of "self-cloned" genetically modified organisms (GMO's) (self-cloning is defined herein as in European Directive 98/81/EC Annex II). When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous and exogenous nucleic acids or proteins are not endogenous to the cell into which it is introduced, but have been obtained from another cell or synthetically or recombinantly produced. In an embodiment, a heterologous gene may replace a homologous gene, in particular a corresponding homologous gene (expression enzyme with same function, but herein with a different co-factor, i.e. $NAD^+$ dependent). Alternatively the homologous gene may be modified in the cell to become $NAD^+$ dependent, e.g. by one or more point mutations in the genome, e.g. with CRISPR CAS technology. Generally, though not necessarily, such nucleic acids encode proteins, i.e. exogenous proteins, that are not normally produced by the cell in which the DNA is transcribed or expressed. Similarly exogenous RNA encodes for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The "specific activity" of an enzyme is herein understood to mean the amount of activity of a particular enzyme per amount of total host cell protein, usually expressed in units of enzyme activity per mg total host cell protein. In the context of the present invention, the specific activity of a particular enzyme may be increased or decreased as compared to the specific activity of that enzyme in an (otherwise identical) wild type host cell.

"Anaerobic conditions" or an anaerobic fermentation process is herein defined as conditions or a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors.

"Disruption" is herein understood to mean any disruption of activity, and includes, but is not limited to deletion, mutation, reduction of the affinity of the disrupted gene and expression of antisense RNA complementary to corresponding mRNA. Native in eukaryotic cell herein is understood as that the gene is present in the eukaryotic cell before the disruption. It includes the situation that the gene native in eukaryotic cell is present in a wild-type eukaryotic cell, a laboratory eukaryotic cell or an industrial eukaryotic cell. Eukaryotic cell may herein also be designated as eukaryotic cell strain or as part of eukaryotic cell strain.

By "wild-type" eukaryotic cell, it is meant a pentose-fermenting eukaryotic cell strain with normal levels of functional NADP+ dependent genes from which the eukaryotic cell of the present invention is derived. In certain cases, the "wild-type eukaryotic cell" as defined in this patent application, may include mutagenized eukaryotic cell.

Reaction equations herein are non-stoichiometric.

Certain embodiments of the invention are now described:

In an embodiment, the eukaryotic cell has a disruption of one or more native gene encoding D-glucose-6-phosphate dehydrogenase and/or native gene encoding 6-phosphogluconate dehydrogenase, wherein native is native in the eukaryotic cell. In an embodiment, in the eukaryotic cell, the D-glucose-6-phosphate dehydrogenase native in the eukaryotic cell is replaced by the heterologous D-glucose-6-phosphate dehydrogenase and/or wherein the 6-phosphogluconate dehydrogenase native in the eukaryotic cell is replaced by the heterologous 6-phosphogluconate dehydrogenase. In an embodiment, in the eukaryotic cell the native genes that are part of the pentose-phosphate-pathway that are $NADP^+$ dependent are disrupted or deleted. Examples of genes to be disrupted or deleted are GND1, GND2 and ZWF1. The heterologous genes $NAD^+$ dependent D-glucose-6-phosphate dehydrogenase and 6-phosphogluconate dehydrogenase may be prokaryotic genes or synthetic genes encoding prokaryotic enzymes. In an embodiment, the eukaryotic cell has heterologous genes are prokaryotic genes originating from *Methylobacillus, Gluconobacter, Bradyrhizobium* and *Haloferax*, e.g.: *Methylobacillus flagellatus, Gluconobacter oxydans, Bradyrhizobium* or *Haloferax volcanii*.

In an embodiment the eukaryotic cell is a yeast cell, e.g. a *Saccharomyces* cell, e.g. *Saccharomyces cerevisiae* cell. In an embodiment, in the eukaryotic cell, an acetaldehyde dehydrogenase-6 (ALD6) is disrupted. In an embodiment, the eukaryotic cell comprises a disruption of one or more of the genes gpp1, gpp2, gpd1 and gpd2 native in the eukaryotic cell.

The eukaryotic cell may comprise: h) one or more nucleotide sequence encoding a heterologous xylose isomerase (E.C. 5.3.1.5) and/or i) arabinose pathway genes, j) one or more nucleotide sequence encoding a heterologous glycerol dehydrogenase (E.C. 1.1.1.6); and k) one or more nucleotide sequence encoding a homologous or heterologous dihydroxyacetone kinase (E.C. 2.7.1.28 or E.C 2.7.1.29). In an embodiment, the eukaryotic cell is a pentose and glucose fermenting eukaryotic cell that is capable of anaerobic simultaneous pentose and glucose consumption. In an embodiment, the substrate is a hydrolysate of lignocellulosic material, e.g. an enzymatic hydrolysate of lignocellulosic material wherein the hydrolysate comprises acetate. The acetate may be at acetate concentration of 0.3% (w/w) or more in the hydrolysate.

The various embodiments of the invention described herein may be cross-combined.

In an embodiment, the invention provides a eukaryotic cell that is genetically modified comprising:
a) D-Glucose-6-phosphate dehydrogenase and/or
b) 6-phosphogluconate dehydrogenase;
c) glucose dehydrogenase, gluconolactonase and gluconate kinase, wherein a) and b) and glucose dehydrogenase in c) are NAD+ dependent;
d) one or more nucleotide sequence encoding a heterologous NAD+-dependent acetylating acetaldehyde dehydrogenase (E.C. 1.2.1.10);
e) one or more nucleotide sequence encoding a homologous or heterologous acetyl-CoA synthetase (E.C. 6.2.1.1);
f) a disruption of one or more aldehyde dehydrogenase (E.C. 1.2.1.4) native in the eukaryotic cell
g) a modification that leads to reduction of glycerol 3-phosphate phosphohydrolase and/or glycerol 3-phosphate dehydrogenase activity, compared to the eukaryotic cell without such modification;
h) one or more nucleotide sequence encoding a heterologous xylose isomerase (E.C. 5.3.1.5);
i) Arabinose pathway genes
j) one or more nucleotide sequence encoding a heterologous glycerol dehydrogenase (E.C. 1.1.1.6); and/or
k) one or more nucleotide sequence encoding a homologous or heterologous dihydroxyacetone kinase (E.C. 2.7.1.28 or E.C. 2.7.1.29).

These features and other embodiments of the invention are hereafter described in more detail.

a) D-Glucose-6-Phosphate Dehydrogenase that is NAD+ Dependent

Native enzyme D-glucose-6-phosphate dehydrogenase (herein abbreviated as G6PDH or ZWF1) is an enzyme that is part of the oxidative part of the pentose-phosphate-pathway (PPP pathway). In eukaryotic cells, this enzyme is NADP+ dependent: The reaction catalyzed by the native enzyme is:

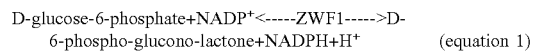  (equation 1)

The D-glucose-6-phosphate dehydrogenase that is NAD+ dependent that is used according to the invention uses NAD+ as cofactor. The reaction of the NAD+ dependent G6PDH enzyme is:

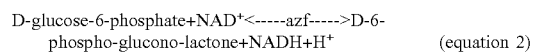  (equation 2)

In an embodiment, the NAD+ dependent G6PDH (enzyme or gene) originates from a prokaryotic organism. "originates" is herein understood to include a) isolated from an organism or b) synthesized gene or protein based on information derived from a gene sequence or protein.

In an embodiment the G6PDH is a heterologous gene encodes a D-glucose-6-phosphate dehydrogenase having at least 50, 55, 60, 65, 70, 75, 80, 85, 90, 95, 98, or 99% identity to SEQ ID NO: 7. In an embodiment the gene encodes an enzyme that is a D-glucose-6-phosphate dehydrogenase having at least 50, 55, 60, 65, 70, 75, 80, 85, 90, 95, 98, or 99% identity to SEQ ID NO: 8. Suitable examples of the above G6PDH enzymes are given in table 1.

TABLE 1

Suitable G6PDH enzymes and identity to G6PDH WP 004044412.1

| Protein | Identity (%) | Accession |
|---|---|---|
| NAD-dependent epimerase [*Haloferax volcanii*] | 100 | WP_004044412.1 |
| sugar epimerase/dehydratase-like protein [*Haloferax sulfurifontis*] | 98 | WP_007274874.1 |
| NAD-dependent epimerase [*Haloferax mucosum*] | 94 | WP_008319571.1 |
| sugar epimerase/dehydratase-like protein [*Haloferax larsenii*] | 91 | WP_007544789.1 |
| NAD-dependent epimerase [*Halogeometricum borinquense*] | 81 | WP_006056268.1 |
| NAD-dependent epimerase [*Halorubrum saccharovorum*] | 75 | WP_004048754.1 |
| nucleoside-diphosphate-sugar epimerase [*Halonotius* sp. J07HN6] | 70 | WP_021060497.1 |
| NAD-dependent epimerase [*Natronomonas pharaonis*] | 62 | WP_011321883.1 | b) 6-phosphogluconate Dehydrogenase

Native enzyme 6-phosphogluconate dehydrogenase (herein abbreviated as 6PGDH or GND1 or GND2) is an enzyme that is part of the oxidative part of the pentose-phosphate-pathway (PPP pathway In eukaryotic cells, this enzyme is NADP+ dependent: The reaction catalyzed by the native enzyme is:

6-phosphogluconate+NADP+<-----GND1 or GND2----->

  (equation 3)

The 6-phosphogluconate dehydrogenase that is NAD+ dependent that is used according to the invention uses NAD+ as cofactor. The reaction catalyzed by the NAD+ dependent 6PGDH enzyme is:

6-phosphogluconate+NAD+<-----GND1 or GND2
(GndA)----->

Ribulose-5-phosphate+NADH+H+ +CO$_2$     (equation 4)

In an embodiment, the NAD+ dependent 6PGDH (enzyme or gene) originates from a prokaryotic organism. "originates" is herein understood to include a) isolated from an organism or b) synthesized based on information derived from an enzyme or gene.

In an embodiment the 6PGDH is a heterologous gene encodes a D-glucose-6-phosphate dehydrogenase having 50, 55, 60, 65, 70, 75, 80, 85, 90, 95, 98, or 99% identity to SEQ ID NO: 1. In an embodiment the gene encodes an enzyme that is a D-glucose-6-phosphate dehydrogenase having 50, 55, 60, 65, 70, 75, 80, 85, 90, 95, 98, or 99% identity to SEQ ID NO: 2. Suitable examples of the above 6PGDH enzymes are given in table 2.

In an embodiment the 6PGDH is a heterologous gene encodes a D-glucose-6-phosphate dehydrogenase having 50, 55, 60, 65, 70, 75, 80, 85, 90, 95, 98, or 99% identity to SEQ ID NO: 3. In an embodiment the gene encodes an enzyme that is a D-glucose-6-phosphate dehydrogenase having 6050, 55, 60, 65, 70, 75, 80, 85, 90, 95, 98, or 99% identity to SEQ ID NO: 4. Suitable examples of the above 6PGDH enzymes are given in table 3.

In an embodiment the 6PGDH is a heterologous gene encodes a D-glucose-6-phosphate dehydrogenase having 50, 55, 60, 65, 70, 75, 80, 85, 90, 95, 98, or 99% identity to SEQ ID NO: 5. In an embodiment the gene encodes an enzyme that is a D-glucose-6-phosphate dehydrogenase having 50, 55, 60, 65, 70, 75, 80, 85, 90, 95, 98, or 99% identity to SEQ ID NO: 6. Suitable examples of the above 6PGDH enzymes are given in table 4.

In an embodiment, the heterologous 6PGDH enzymes or genes are prokaryotic genes originating from an organism chosen from the genus list: *Methylobacillus, Gluconobacter, Bradyrhizobium* and *Haloferax*. In an embodiment, the 6PGDH enzymes or genes are prokaryotic genes originating from an organism chosen from the species list: *Methylobacillus flagellatus, Gluconobacter oxydans, Bradyrhizobium* and *Haloferax volcanii*. Examples of suitable 6PGDH proteins are given in tables 2, 3 and 4.

TABLE 2

Suitable 6PGDH enzymes and identity to AAF34407.1 6-phosphogluconate dehydrogenase (*Methylobacillus flagellates* 6PGDH)

| Protein | Identity (%) | Accession |
| --- | --- | --- |
| NAD-linked 6-phosphogluconate dehydrogenase [*Methylobacillus flagellatus*] (gndA) | 100 | AAF34407.1 |
| 6-phosphogluconate dehydrogenase [*Methylobacillus glycogenes*] | 90 | WP_025869439.1 |
| 6-phosphogluconate dehydrogenase [*Methylovorus glucosotrophus*] | 82 | WP_015829859.1 |
| 6-phosphogluconate dehydrogenase [*Methylovorus* sp. MP688] | 82 | WP_013441936.1 |
| 6-phosphogluconate dehydrogenase [*Methylotenera versatilis*] | 81 | WP_047538584.1 |
| 6-phosphogluconate dehydrogenase [*Methylophilus* sp. 5] | 80 | WP_029148659.1 |
| 6-phosphogluconate dehydrogenase [*Sulfuricella denitrificans*] | 75 | WP_009206043.1 |
| 6-phosphogluconate dehydrogenase [*Candidatus Methylopumilus planktonicus*] | 70 | WP_046487838.1 |
| 6-phosphogluconate dehydrogenase [*Thioalkalivibrio sulfidiphilus*] | 66 | WP_012637452.1 |
| 6-phosphogluconate dehydrogenase [*Thermithiobacillus tepidarius*] | 60 | WP_028989561.1 |
| 6-phosphogluconate dehydrogenase [*Deinococcus ficus*] | 58 | WP_027462489.1 |

TABLE 3

Suitable 6PGDH proteins and identity to WP 011253227.1; 6-phosphogluconate dehydrogenase (*Gluconobacter oxydans* 6PGDH]

| Protein | Identity (%) | Accession |
| --- | --- | --- |
| 6-phosphogluconate dehydrogenase [*Gluconobacter oxydans*] | 100 | WP_011253227.1 |
| 6-phosphogluconate dehydrogenase [*Gluconobacter oxydans*] | 99 | WP_041112000.1 |
| 6-phosphogluconate dehydrogenase [*Gluconobacter morbifer*] | 86 | WP_008850548.1 |
| 6-phosphogluconate dehydrogenase [*Gluconobacter oxydans*] | 84 | WP_046899919.1 |
| 6-phosphogluconate dehydrogenase [*Asaia astilbis*] | 77 | WP_025823114.1 |
| 6-phosphogluconate dehydrogenase [*Acetobacter cibinongensis*] | 76 | WP_048838399.1 |

TABLE 3-continued

Suitable 6PGDH proteins and identity to WP 011253227.1; 6-phosphogluconate dehydrogenase (*Gluconobacter oxydans* 6PGDH]

| Protein | Identity (%) | Accession |
| --- | --- | --- |
| 6-phosphogluconate dehydrogenase [*Komagataeibacter xylinus*] | 75 | WP_048857212.1 |
| 6-phosphogluconate dehydrogenase [*Granulibacter bethesdensis*] | 67 | WP_011631561.1 |

TABLE 4

Suitable 6PGDH proteins and identity to WP 011089498.1; 6-phosphogluconate dehydrogenase (*Bradyrhizobium* 6PGDH]

| Protein | Identity (%) | Accession |
| --- | --- | --- |
| MULTISPECIES: 6-phosphogluconate dehydrogenase [*Bradyrhizobium*] | 100 | WP_011089498.1 |
| 6-phosphogluconate dehydrogenase [*Bradyrhizobium* sp. WSM2254] | 98 | WP_027546897.1 |
| 6-phosphogluconate dehydrogenase [*Bradyrhizobium japonicum*] | 95 | WP_024339411.1 |
| 6-phosphogluconate dehydrogenase [*Bradyrhizobium elkanii*] | 83 | WP_028347094.1 |
| 6-phosphogluconate dehydrogenase [*Rhodopseudomonas palustris*] | 77 | WP_011440787.1 |
| 6-phosphogluconate dehydrogenase [*Microvirga lupini*] | 75 | WP_036351036.1 |
| 6-phosphogluconate dehydrogenase (decarboxylating) [*Afipia felis*] | 72 | WP_002718635.1 |
| 6-phosphogluconate dehydrogenase [*Methylobacterium oryzae*] | 71 | WP_043757546.1 | c) Glucose Dehydrogenase, Gluconolactonase and Gluconate Kinase

In an embodiment the cell comprises glucose dehydrogenase, gluconolactonase and gluconate kinase. The introduction of these genes and the expression of the corresponding enzymes leads to the following reactions in the cell:

Glucose+NAD$^+$<-----glucose dehydrogenase----->gluconolactone+NADH (equation 5), followed by:

Gluconolactone+H$_2$O<-----gluconolactonase----->gluconate (equation 6), followed by gluconate+ATP<-----gluconate kinase----->6-P-gluconate+ADP$^+$+Pi (equation 7)

which completes the pathway from glucose to 6-P-gluconate.

These enzymes (designated as c1), c2) and c3) respectively are now described in more detail.

c1) NAD$^+$ dependent glucose dehydrogenase (EC 1.1.1.118) is an enzyme that catalyzes the chemical reaction D-glucose+NAD$^+$ ⇌ D-glucono-1,5-lactone+NADH (equation 8)

Thus, the two substrates of this enzyme are D-glucose and acceptor, whereas its two products are D-glucono-1,5-lactone and reduced acceptor. This enzyme belongs to the family of oxidoreductases, specifically those acting on the CH—OH group of donor with other acceptors. The systematic name of this enzyme class is D-glucose:acceptor 1-oxidoreductase. Other names in common use include glucose dehydrogenase (*Aspergillus*), glucose dehydrogenase (decarboxylating), and D-glucose:(acceptor) 1-oxidoreductase. This enzyme participates in pentose phosphate pathway. It employs one cofactor, FAD.

c2) Gluconolactonase (EC 3.1.1.17) is an enzyme that catalyzes the chemical reaction glucono-1,5-lactone+H$_2$O ⇌ D-gluconate (equation 9)

Thus, the two substrates of this enzyme are D-glucono-1,5-lactone and H$_2$O, whereas its product is D-gluconate. This enzyme belongs to the family of hydrolases, specifically those acting on carboxylic ester bonds. The systematic name of this enzyme class is D-glucono-1,5-lactone lactonohydrolase. Other names in common use include lactonase, aldonolactonase, glucono-delta-lactonase, and gulonolactonase. This enzyme participates in the pentose phosphate pathway.

c3) Gluconate kinase or gluconokinase (EC 2.7.1.12) is an enzyme that catalyzes the chemical reaction:

ATP+D-gluconate ⇌ ADP+6-phospho-D-gluconate (Equation 10)

Thus, the two substrates of this enzyme are ATP and D-gluconate, whereas its two products are ADP and 6-phospho-D-gluconate.

This enzyme belongs to the family of transferases, specifically those transferring phosphorus-containing groups (phosphotransferases) with an alcohol group as acceptor. The systematic name of this enzyme class is ATP:D-gluconate 6-phosphotransferase. Other names in common use include gluconokinase (phosphorylating), and gluconate kinase. This enzyme participates in pentose phosphate pathway.

d) Acetaldehyde Dehydrogenase (Acetylating) (EC 1.2.1.10).

The cell of the invention may further comprise an exogenous gene coding for an enzyme with the ability to reduce acetylCoA into acetaldehyde, which gene confers to the cell the ability to convert acetylCoA (and/or acetic acid) into ethanol. An enzyme with the ability to reduce acetylCoA into acetaldehyde is herein understood as an enzyme which catalyzes the reaction (ACDH; EC 1.2.1.10):

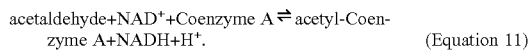

acetaldehyde+NAD⁺+Coenzyme A ⇌ acetyl-Coenzyme A+NADH+H⁺.   (Equation 11)

Thus, the enzyme catalyzes the conversion of acetylCoA into acetaldehyde (and vice versa) and is also referred to as an (acetylating NAD-dependent) acetaldehyde dehydrogenase or an acetyl-CoA reductase. The enzyme may be a bifunctional enzyme which further catalyzes the conversion of acetaldehyde into ethanol (and vice versa; see below). For convenience we shall refer herein to an enzyme having at least the ability to reduce acetylCoA into either acetaldehyde or ethanol as an "acetaldehyde dehydrogenase". It is further understood herein that the cell has endogenous alcohol dehydrogenase activities which allow the cell, being provided with acetaldehyde dehydrogenase activity, to complete the conversion of acetyl-CoA into ethanol. Further the cell has endogenous or exogenous acetyl-CoA synthetase, which allows the cell, being provided with acetaldehyde dehydrogenase activity, to complete the conversion of acetic acid (via acetyl-CoA) into ethanol.

The exogenous gene may encode for a monofunctional enzyme having only acetaldehyde dehydrogenase activity (i.e. an enzyme only having the ability to reduce acetylCoA into acetaldehyde) such as e.g. the acetaldehyde dehydrogenase encoded by the E. coli mhpF gene or E. coli EutE gene (the part coding for acetaldehyde dehydrogenase activity).

Suitable examples of prokaryotes comprising monofunctional enzymes with acetaldehyde dehydrogenase activity are provided in Table 5. The amino acid sequences of these monofunctional enzymes are available in public databases and can be used by the skilled person to design codon-optimized nucleotide sequences coding for the corresponding monofunctional enzyme.

TABLE 5

Suitable enzymes with acetaldehyde dehydrogenase activity and identity to E. coli mhpF

| Organism | Amino acid identity (%) |
|---|---|
| Escherichia coli str. K12 substr. MG1655 | 100% |
| Shigella sonnei | 100% |
| Escherichia coli IAI39 | 99% |
| Citrobacter youngae ATCC 29220 | 93% |
| Citrobacter sp. 30_2 | 92% |
| Klebsiella pneumoniae 342) | 87% |
| Klebsiella variicola | 87% |
| Pseudomonas putida | 81% |
| Ralstonia eutropha JMP134 | 82% |
| Burkholderia sp. H160 | 81% |
| Azotobacter vinelandii DJ | 79% |
| Ralstonia metallidurans CH34 | 70% |
| Xanthobacter autotrophicus Py2 | 67% |
| Burkholderia cenocepacia J2315 | 68% |
| Frankia sp. EAN1pec | 67% |
| Polaromonas sp. JS666 | 68% |
| Burkholderia phytofirmans PsJN | 70% |
| Rhodococcus opacus B4 | 64% |

In an embodiment, the cell comprises an exogenous gene coding for a bifunctional enzyme with acetaldehyde dehydrogenase and alcohol dehydrogenase activity, which gene confers to the cell the ability to convert acetylCoA into ethanol. The advantage of using a bifunctional enzyme with acetaldehyde dehydrogenase and alcohol dehydrogenase activities as opposed to separate enzymes for each of the acetaldehyde dehydrogenase and alcohol dehydrogenase activities, is that it allows for direct channeling of the intermediate between enzymes that catalyze consecutive reactions in a pathway offers the possibility of an efficient, exclusive, and protected means of metabolite delivery. Substrate channeling thus decreases transit time of intermediates, prevents loss of intermediates by diffusion, protects labile intermediates from solvent, and forestalls entrance of intermediates into competing metabolic pathways. The bifunctional enzyme therefore allows for a more efficient conversion of acetylCoA into ethanol as compared to the separate acetaldehyde dehydrogenase and alcohol dehydrogenase enzymes. A further advantage of using the bifunctional enzyme is that it may also be used in cells having little or no alcohol dehydrogenase activity under the condition used, such as e.g. anaerobic conditions and/or conditions of catabolite repression.

Bifunctional enzymes with acetaldehyde dehydrogenase and alcohol dehydrogenase activity are known in the art. The may be present in prokaryotes and protozoans, including e.g. the bifunctional enzymes encoded by the Escherichia coli adhE and Entamoeba histolytica ADH2 genes (see e.g. Bruchaus and Tannich, 1994, J. Biochem., 303: 743-748; Burdette and Zeikus, 1994, J. Biochem. 302: 163-170; Koo et al., 2005, Biotechnol. Lett. 27: 505-510; Yong et al., 1996, Proc Natl Acad Sci USA, 93: 6464-6469). Bifunctional enzymes with acetaldehyde dehydrogenase and alcohol dehydrogenase activity are larger proteins consisting of around 900 amino acids and they are bifunctional in that they exhibit both acetaldehyde dehydrogenase (ACDH; EC 1.2.1.10) and alcohol dehydrogenase activity (ADH; EC 1.1.1.1). The E. coli adhE and Entamoeba histolytica ADH2 show 45% amino acid identity. Suitable examples of bifunctional enzymes with acetaldehyde dehydrogenase and alcohol dehydrogenase activity and identity to E. coli adhE are given in table 6. Suitable examples of bifunctional enzymes with acetaldehyde dehydrogenase and alcohol dehydrogenase activity and identity to Entamoeba histolytica ADH2 are given in table 7.

TABLE 6

Suitable bifunctional enzymes with acetaldehyde dehydrogenase and alcohol dehydrogenase activity and identity to E. coli adhE

| Organism | Amino acid identity (%) |
|---|---|
| Escherichia coli O157:H7 str. Sakai | 100% |
| Shigella sonnei | 100% |
| Shigella dysenteriae 1012 | 99% |
| Klebsiella pneumoniae 342 | 97% |
| Enterobacter sp. 638 | 94% |
| Yersinia pestis biovar Microtus str. 91001 | 90% |
| Serratia proteamaculans 568 | 90% |
| Pectobacterium carotovorum WPP14 | 90% |
| Sodalis glossinidius str. 'morsitans' | 87% |
| Erwinia tasmaniensis Et1/99 | 86% |
| Aeromonas hydrophila ATCC 7966 | 81% |
| Vibrio vulnificus YJ016] | 76% |

TABLE 7

Suitable bifunctional enzymes with acetaldehyde dehydrogenase and alcohol dehydrogenase activity and identity to *Entamoeba histolytica* ADH2

| Organism | Amino acid identity (%) |
| --- | --- |
| *Entamoeba histolytica* HM-1:IMSS | 99% |
| *Entamoeba dispar* SAW760 | 98% |
| *Mollicutes bacterium* D7 | 65% |
| *Fusobacterium mortiferum* ATCC 9817 | 64% |
| *Actinobacillus succinogenes* 130Z | 63% |
| *Pasteurella multocida* Pm70 | 62% |
| *Mannheimia succiniciproducens* MBEL55E | 61% |
| *Streptococcus* sp. 2_1_36FAA] | 61% |

TABLE 8

Suitable enzymes with acetaldehyde dehydrogenase and alcoholdehydrogenase activity and identity to *E. coli* EutE

| Organism | Amino acid identity (%) |
| --- | --- |
| *Escherichia coli* (EutE) | 100% |
| *Escherichia coli* O157:H7 | 99% |
| *Shigella boydi* | 98% |
| *Salmonella typhimurium* | 94% |
| *Salmonella enterica* subsp. *enterica* serovar Weltevreden | 94% |
| *Salmonella choleraesuis* | 93% |
| *Citrobacter youngae* | 93% |
| *Klebsiella pneumoniae* subsp. *pneumoniae* | 92% |
| *Yersinia intermedia* | 80% |
| *Photobacterium profundum* | 59% |
| *Bilophila wadsworthia* | 60% |
| *Shewanella benthica* | 58% |
| *Thermincola potens* | 51% |
| *Acetonema longum* | 50% | drogenase and alcohol dehydrogenase activities, or the enzyme having acetaldehyde dehydrogenase activity include promoters that are preferably insensitive to catabolite (glucose) repression, that are active under anaerobic conditions and/or that preferably do not require xylose or arabinose for induction. Examples of such promoters are given above.

Preferably, the nucleotide sequence encoding the bifunctional enzyme having acetaldehyde dehydrogenase and alcohol dehydrogenase activities, or the enzyme having acetaldehyde dehydrogenase activity is adapted to optimize its codon usage to that of the cell in question (as described above).

e) Acetyl-CoA Synthetase (EC 6.2.1.1);

The cell of the invention may comprise a gene coding for an enzyme that has the specific activity of Acetyl-CoA synthetase. Acetyl-CoA synthetase or Acetate-CoA ligase is an enzyme (EC 6.2.1.1) involved in metabolism of carbon sugars. It is in the ligase class of enzymes, meaning that it catalyzes the formation of a new chemical bond between two large molecules.

The two molecules joined by acetyl-CoA synthetase are acetate and coenzyme A (CoA). The reaction with the substrates and products included is:

Acetate+CoA ⇌ Pyrophosphate+Acetyl-CoA    (Equation 12)

The Acs1 form and the Acs2 form of acetyl-CoA synthetase are encoded by the genes ACS1 and ACS2 respectively.

Suitable examples of enzymes with acetyl-CoA synthetase activity are provided in Table 9.

TABLE 9

Suitable ACS's with identity to ACS2 protein of *Saccharomyces cerevisiae*.

| Description | Identity (%) | Accession no |
| --- | --- | --- |
| acetate--CoA ligase ACS2 [*Saccharomyces cerevisiae* S288c] | 100 | NP_013254.1 |
| acetyl CoA synthetase [*Saccharomyces cerevisiae* YJM789] | 99 | EDN59693.1 |
| acetate--CoA ligase [*Kluyveromyces lactis* NRRL Y-1140] | 85 | XP_453827.1 |
| acetate--CoA ligase [*Candida glabrata* CBS 138] | 83 | XP_445089.1 |
| acetate--CoA ligase [*Scheffersomyces stipitis* CBS 6054] | 68 | XP_001385819.1 |
| acetyl-coenzyme A synthetase FacA [*Aspergillus fumigatus* A1163] | 63 | EDP50475.1 |
| acetate--CoA ligase facA-*Penicillium chrysogenum* [*Penicillium chrysogenum* Wisconsin 54-1255] | 62 | XP_002564696.1 |

For expression of the nucleotide sequence encoding the bifunctional enzyme having acetaldehyde dehydrogenase and alcohol dehydrogenase activities, or the enzyme having acetaldehyde dehydrogenase activity, the nucleotide sequence (to be expressed) is placed in an expression construct wherein it is operably linked to suitable expression regulatory regions/sequences to ensure expression of the enzyme upon transformation of the expression construct into the cell of the invention (see above). Suitable promoters for expression of the nucleotide sequence coding for the enzyme having the bifunctional enzyme having acetaldehyde dehyf) Disruption of One or More Aldehyde Dehydrogenase (E.C. 1.2.1.4) Native in the Eukaryotic Cell.

The enzyme that may be disrupted according to the invention is an aldehyde dehydrogenase aldehyde dehydrogenase (E.C:1.2.1.4) native in the eukaryotic cell.

In an embodiment the aldehyde dehydrogenase native in the eukaryotic cell is acetaldehyde dehydrogenase-6 (ALD6).

ALD6 is herein any Mg2+ activated enzyme that catalyses the dehydrogenation of acetaldehyde into acetate, and vice-versa.

The reaction that is catalyzed by ALD6 is:

Acetaldehyde+NAD$^+$/NADP$^+$+H$_2$O<-----ALD6----->
acetate+NAD/NADPH (Equation 13)

The enzyme ALD6 in equation 13, generates NADPH and acetate. For that reason, in context of this invention, the disruption or deletion of ALD6 is a preferred embodiment.

A further advantage of deletion of ALD6 is apparent if the strain according to the invention comprises an acetylating acetaldehyde dehydrogenase (e.g., adhE or acdH) (see d) and WO2015028583 and WO2015028582)). Combination of acetylating acetaldehyde dehydrogenase and ALD6 in a eukaryotic cell according to the invention may lead to a futile cycle that consumes ATP. Deletion of ALD6 breaks the futile cycle, so that the ATP consumption by the futile cycle is avoided. In an embodiment of the invention the eukaryotic cell an ALD6 of *Saccharomyces cerevisiae* is deleted. This is illustrated in FIG. 4.

Suitable ALD6 nucleotide sequences for disruption with identity to the ALD6 nucleotide sequence of *Saccharomyces cerevisiae* in other eukaryotic cells are given in table 10.

TABLE 10

Suitable ALD6 nucleotide sequences for disruption occurring in different types of eukaryotic cell

| Species and strain | Accession number | % ID |
|---|---|---|
| aldehyde dehydrogenase (NADP(+)) ALD6 [*Saccharomyces cerevisiae* S288c] | NP_015264.1 | 100 |
| Ald6p [*Saccharomyces cerevisiae* AWRI796] | EGA72659.1 | 99 |
| Aldehyde dehydrogenase 6 [*Saccharomyces cerevisiae* × *Saccharomyces kudriavzevii*] | CCD31406.1 | 97 |
| hypothetical protein NDAI_0E02900 [*Naumovozyma dairenensis* CBS 421] | XP_003670350.1 | 80 |
| magnesium-activated aldehyde dehydrogenase [*Kluyveromyces marxianus* DMKU3-1042] | BAP69922.1 | 74 |
| aldehyde dehydrogenase (NAD+) [*Wickerhamomyces ciferrii*] | XP_011273253.1 | 63 |
| aldehyde dehydrogenase [*Brettanomyces bruxellensis* AWRI1499] [*Dekkera bruxellensis* AWRI1499] | EIF46557.1 | 56 | g) A Modification that Leads to Reduction of Glycerol 3-Phosphate Phosphohydrolase and/or Glycerol 3-Phosphate Dehydrogenase Activity The eukaryotic cell further may further comprise a modification that leads to reduction of glycerol 3-phosphate phosphohydrolase and/or glycerol 3-phosphate dehydrogenase activity, compared to the eukaryotic cell without such modification.

In that embodiment, the cell may comprises a disruption of one or more endogenous nucleotide sequence encoding a glycerol 3-phosphate phosphohydrolase and/or encoding a glycerol 3-phosphate dehydrogenase gene.

In such embodiment the enzymatic activity needed for the NADH-dependent glycerol synthesis is reduced or deleted. The reduction or deleted of this enzymatic activity can be achieved by modifying one or more genes encoding a NAD-dependent glycerol 3-phosphate dehydrogenase activity (GPD) or one or more genes encoding a glycerol phosphate phosphatase activity (GPP), such that the enzyme is expressed considerably less than in the wild-type or such that the gene encoded a polypeptide with reduced activity.

Such modifications can be carried out using commonly known biotechnological techniques, and may in particular include one or more knock-out mutations or site-directed mutagenesis of promoter regions or coding regions of the structural genes encoding GPD and/or GPP. Alternatively, eukaryotic cell strains that are defective in glycerol production may be obtained by random mutagenesis followed by selection of strains with reduced or absent activity of GPD and/or GPP. *S. cerevisiae* GPD1, GPD2, GPP1 and GPP2 genes are shown in WO2011010923, and are disclosed in SEQ ID NO: 24-27 of that application.

Thus, in the cells of the invention, the specific glycerol 3-phosphate phosphohydrolase and/or encoding a glycerol 3-phosphate dehydrogenase gene may be reduced. In the cells of the invention, the specific glycerolphosphate dehydrogenase activity is preferably reduced by at least a factor 0.8, 0.5, 0.3, 0.1, 0.05 or 0.01 as compared to a strain which is genetically identical except for the genetic modification causing the reduction in specific activity, preferably under anaerobic conditions. Glycerolphosphate dehydrogenase activity may be determined as described by Overkamp et al. (2002, Eukaryotic cell 19:509-520).

A preferred gene encoding a glycerolphosphate dehydrogenase whose activity is to be reduced or inactivated in the cell of the invention is the *S. cerevisiae* GPD1 as described by van den Berg and Steensma (1997, Eukaryotic cell 13:551-559), encoding the amino acid sequence GPD1 and orthologues thereof in other species.

Suitable examples of an enzyme with glycerolphosphate dehydrogenase activity belonging to the genus *Saccharomyces*, *Naumovozyna*, *Candida Vanderwaltozyma* and *Zygosaccharomyces* are provided in Table 11.

TABLE 11

Suitable enzymes with glycerolphosphate dehydrogenase (GPD1) activity characterized by organism source and amino-acid identity to *S. cervisiae* glycerolphosphate dehydrogenase (GPD1)

| Organism | Amino acid identity (%) |
|---|---|
| S. cerevisiae | 100% |
| Naumovozyma dairenensis | 79% |
| Naumovozyma castellii | 80% |
| Candida glabrata | 77% |
| Vanderwaltozyma polyspora | 77% |
| Zygosaccharomyces rouxii | 74% |
| Saccharomycopsis fibuligera | 61% |

However, in some strains e.g. of *Saccharomyces*, *Candida* and *Zygosaccharomyces* a second gene encoding a glycerolphosphate dehydrogenase is active, i.e. the GPD2, Another preferred gene encoding a glycerolphosphate dehydrogenase whose activity is to be reduced or inactivated in the cell of the invention therefore is an *S. cerevisiae* GPD2, encoding the amino acid sequence GPD2 and orthologues thereof in other species.

Suitable examples of organisms (hosts) comprising an enzyme with glycerolphosphate dehydrogenase activity belonging to the genus (Zygo)*Saccharomyces* and *Candida* are provided in Table 12.

TABLE 12

Suitable enzymes with glycerol phosphate dehydrogenase (GPD2) activity characterized by organism source and amino-acid identity to *S. cervisiae* glycerolphosphate dehydrogenase (GPD2)

| Organism | Amino acid identity (%) |
|---|---|
| S. cerevisiae | 100% |
| Candida glabrata | 75% |
| Zygosaccharomyces rouxii | 73% |

TABLE 12-continued

Suitable enzymes with glycerol phosphate dehydrogenase (GPD2) activity characterized by organism source and amino-acid identity to *S. cervisiae* glycerolphosphate dehydrogenase (GPD2)

| Organism | Amino acid identity (%) |
|---|---|
| *Spathaspora passalidarum* | 62% |
| *Scheffersomyces stipites* | 61% |

In an embodiment, the cell is a eukaryotic cell wherein the genome of the eukaryotic cell comprises a mutation in at least one gene selected from the group of GPD1, GPD2, GPP1 and GPP2, which mutation may be a knock-out mutation, which knock-out mutation may be a complete deletion of at least one of said genes in comparison to the eukaryotic cell's corresponding wild-type eukaryotic cell gene.

h) Xylose Isomerase (E.C. 5.3.1.5).

In an embodiment, the eukaryotic cell may comprise a xylose isomerase ((E.C. 5.3.1.5); xylA).

A "xylose isomerase" (E.C. 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). Generally a xylose isomerase requires a bivalent cation, such as magnesium, manganese or cobalt as a cofactor.

i) Arabinose Pathway Enzymes (L-Arabinose Isomerase (araA), L-Ribulokinase (araB), and L-Ribulose-5-Phosphate 4-Epimerase (araD))

In an embodiment, the cell comprised genes that express enzymes of an L-arabinose fermentation pathway. EP 1 499 708 discloses the construction of a L-arabinose-fermenting strain by overexpression of the L-arabinose pathway. In the pathway,
the enzymes L-arabinose isomerase (araA), L-ribulokinase (araB), and L-ribulose-5-phosphate 4-epimerase (araD) are involved converting L-arabinose to L-ribulose, Lribulose-5-P, and D-xylulose-5-P, respectively.

j) Glycerol Dehydrogenase (EC 1.1.1.6)

A glycerol dehydrogenase is herein understood as an enzyme that catalyzes the chemical reaction (EC 1.1.1.6):

$$glycerol+NAD^+ \rightleftharpoons glycerone+NADH+H^+ \quad \text{(Equation 14)}$$

Other names in common use include glycerin dehydrogenase, NAD$^+$-linked glycerol dehydrogenase and glycerol: NAD+ 2-oxidoreductase. Preferably the genetic modification causes overexpression of a glycerol dehydrogenase, e.g. by overexpression of a nucleotide sequence encoding a glycerol dehydrogenase. The nucleotide sequence encoding the glycerol dehydrogenase may be endogenous to the cell or may be a glycerol dehydrogenase that is heterologous to the cell. Nucleotide sequences that may be used for overexpression of glycerol dehydrogenase in the cells of the invention are e.g. the glycerol dehydrogenase gene from *S. cerevisiae* (GCY1) as e.g. described by Oechsner et al. (1988, FEBS Lett. 238: 123-128) or Voss et al. (1997, Eukaryotic cell 13: 655-672).

k) One or More Nucleotide Sequence Encoding a Homologous or Heterologous Dihydroxyacetone Kinase (E.C. 2.7.1.28 or E.C. 2.7.1.29)

A dihydroxyacetone kinase is herein understood as an enzyme that catalyzes one of the chemical reactions:

EC 2.7.1.28 ATP+D-glyceraldehyde<=>ADP+D-glyceraldehyde 3-phosphate

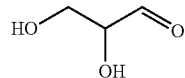

EC 2.7.1.29 ATP+glycerone<=>ADP+glycerone phosphate

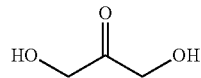

Glycerone=dihydroxyacetone. (Equation 15)

Other names in common use include glycerone kinase, ATP:glycerone phosphotransferase and (phosphorylating) acetol kinase. It is understood that glycerone and dihydroxyacetone are the same molecule. Preferably the genetic modification causes overexpression of a dihydroxyacetone kinase, e.g. by overexpression of a nucleotide sequence encoding a dihydroxyacetone kinase. The nucleotide sequence encoding the dihydroxyacetone kinase may be endogenous to the cell or may be a dihydroxyacetone kinase that is heterologous to the cell. Nucleotide sequences that may be used for overexpression of dihydroxyacetone kinase in the cells of the invention are e.g. the dihydroxyacetone kinase genes from *S. cerevisiae* (DAK1) and (DAK2) as e.g. described by Molin et al. (2003, J. Biol. Chem. 278:1415-1423).

Suitable examples of enzymes with glycerol dehydrogenase activity are provided in Table 13.

TABLE 13

Suitable GCY's with identity to GCY1 protein of *Saccharomyces cerevisiae* GCY1.

| Description | Identity (%) | Accession number |
|---|---|---|
| Gcy1p [*Saccharomyces cerevisiae* S288c] | 100% | NP_014763.1 |
| GCY1-like protein [*Saccharomyces kudriavzevii* IFO 1802] | 89% | EJT43197.1 |
| hypothetical protein KNAG_0C04910 [*Kazachstania naganishii* CBS 8797] | 69% | CCK69592.1 |
| Ypr1p [*Saccharomyces cerevisiae* S288c] | 65% | NP_010656.1 |
| Aldo/keto reductase [*Scheffersomyces stipitis* CBS 6054] >gb|ABN65453.1 | 55% | XP_001383482.1 |

Suitable examples of enzymes with dihydroxy acetone kinase activity are provided in Table 14.

TABLE 14

Suitable DAK's with identity to DAK1 protein of *Saccharomyces cerevisiae*.

| Description | Identity (%) | Accession number |
|---|---|---|
| Dak1p [*Saccharomyces cerevisiae* S288c] | 100 | NP_013641.1 |
| dihydroxyacetone kinase [*Saccharomyces cerevisiae* YJM789] | 99 | EDN64325.1 |
| DAK1-like protein [*Saccharomyces kudriavzevii* IFO 1802] | 95 | EJT44075.1 |

TABLE 14-continued

Suitable DAK's with identity to DAK1 protein of *Saccharomyces cerevisiae*.

| Description | Identity (%) | Accession number |
|---|---|---|
| ZYBA0S11-03576g1_1 [*Zygosaccharomyces bailii* CLIB213] | 77 | CDF91470.1 |
| hypothetical protein [*Kluyveromyces lactis* NRRL Y-1140] | 70 | XP_451751.1 |
| hypothetical protein [*Candida glabrata* CBS 138] | 63 | XP_449263.1 |
| Dak2p [*Saccharomyces cerevisiae* S288c] | 44 | NP_116602.1 |

Other embodiments of the invention are now described in more detail.

The invention further relates to a eukaryotic cell as described herein in fermentation in the wine industry.

In another embodiment the invention relates to the use of the eukaryotic cell as described herein in fermentation in the biofuel industry.

Further the invention relates to a process for the fermentation of a substrate to produce a fermentation product with an eukaryotic cell as described herein, in the wine biofuel industry, wherein the acetate consumption is at least 10%, at least 20%, or at least 25% increased relative to the corresponding fermentation with wild-type eukaryotic cell. In an embodiment thereof, the ethanol yield is at least about 0.5%, or at least 1% higher than that of a process with the corresponding wild-type eukaryotic cell. In such process, preferably pentose and glucose are co-fermented. In such process a hydrolysate of lignocellulosic material may be fermented. The hydrolysate may be an enzymatic hydrolysate of lignocellulosic material. Such hydrolysate may comprise acetate. The acetate comprising hydrolysate may have an acetate concentration of 0.3% (w/w) or more.

The eukaryotic cell may contain genes of a pentose metabolic pathway non-native to the eukaryotic cell and/or that allow the eukaryotic cell to convert pentose(s). In one embodiment, the eukaryotic cell may comprise one or two or more copies of one or more xylose isomerases and/or one or two or more copies of one or more xylose reductase and xylitol dehydrogenase genes, allowing the eukaryotic cell to convert xylose. In an embodiment thereof, these genes may be integrated into the eukaryotic cell genome. In another embodiment, the eukaryotic cell comprises the genes araA, araB and araD. It is then able to ferment arabinose. In one embodiment of the invention the eukaryotic cell comprises xylA-gene, XYL1 gene and XYL2 gene and/or XKS1-gene, to allow the eukaryotic cell to ferment xylose; deletion of the aldose reductase (GRE3) gene; overexpression of PPP-genes, TAL1, TKL1, RPE1 and RKI1 to allow the increase of the flux through the pentose phosphate path-way in the cell, and/or overexpression of GAL2 and/or deletion of GAL80. Thus though inclusion of the above genes, suitable pentose or other metabolic pathway(s) may be introduced in the eukaryotic cell that were non-native in the (wild type) eukaryotic cell. According to an embodiment, the following genes may be introduced in the eukaryotic cell by introduction into a host cell:

1) a set consisting of PPP-genes TAL1, TKL1, RPE1 and RKI1, optionally under control of strong constitutive promoter;
2) a set consisting of a xylA-gene under under control of strong constitutive promoter;
3) a set comprising a XKS1-gene under control of strong constitutive promoter,
4) a set consisting of the genes araA, araB and araD under control of a strong constitutive promoter
5) deletion of an aldose reductase gene The above cells may be constructed using known recombinant expression techniques. The co-factor modification may be effected before, simultaneous or after any of the modifications 1)-5).

The eukaryotic cell according to the invention may be subjected to evolutionary engineering to improve its properties. Evolutionary engineering processes are known processes. Evolutionary engineering is a process wherein industrially relevant phenotypes of a microorganism, herein the eukaryotic cell, can be coupled to the specific growth rate and/or the affinity for a nutrient, by a process of rationally set-up natural selection. Evolutionary Engineering is for instance described in detail in Kuijper, M, et al, FEMS Eukaryotic cell Research 5(2005) 925-934, WO2008041840 and WO2009112472. After the evolutionary engineering the resulting pentose fermenting eukaryotic cell is isolated. The isolation may be executed in any known manner, e.g. by separation of cells from a eukaryotic cell broth used in the evolutionary engineering, for instance by taking a cell sample or by filtration or centrifugation.

In an embodiment, the eukaryotic cell is marker-free. As used herein, the term "marker" refers to a gene encoding a trait or a phenotype which permits the selection of, or the screening for, a host cell containing the marker. Marker-free means that markers are essentially absent in the eukaryotic cell. Being marker-free is particularly advantageous when antibiotic markers have been used in construction of the eukaryotic cell and are removed thereafter. Removal of markers may be done using any suitable prior art technique, e.g. intramolecular recombination.

In one embodiment, the industrial eukaryotic cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

The eukaryotic cell further may comprise those enzymatic activities required for conversion of pyruvate to a desired fermentation product, such as ethanol, butanol (e.g. n-butanol, 2-butanol and isobutanol), lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

In an embodiment, the eukaryotic cell is derived from an industrial eukaryotic cell. An industrial cell and industrial eukaryotic cell may be defined as follows. The living environments of (eukaryotic cell) cells in industrial processes are significantly different from that in the laboratory. Industrial eukaryotic cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial eukaryotic cell strains are generally more robust towards these changes in environmental conditions which may occur in the applications they are used, such as in the baking industry, brewing industry, wine making and the biofuel ethanol industry. In one embodiment, the industrial eukaryotic cell is constructed on the basis of an industrial host cell, wherein the construction is conducted as described hereinafter. Examples of industrial eukaryotic cell (*S. cerevisiae*) are Ethanol Red® (Fermentis) Fermiol® (DSM) and Thermosacc® (Lallemand).

The eukaryotic cells according to the invention are preferably inhibitor tolerant, i.e. they can withstand common inhibitors at the level that they typically have with common pretreatment and hydrolysis conditions, so that the eukaryotic cells can find broad application, i.e. it has high applicability for different feedstock, different pretreatment methods and different hydrolysis conditions. In an embodiment the eukaryotic cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy-methylfurfural. Examples or phenolic compounds are vannilin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions. For phenolics: several tens of milligrams per liter, up to a gram per liter, depending on the feedstock, the pretreatment and the hydrolysis conditions.

In an embodiment, the eukaryotic cell is a cell that is naturally capable of alcoholic fermentation, preferably, anaerobic alcoholic fermentation. A eukaryotic cell preferably has a high tolerance to ethanol, a high tolerance to low pH (i.e. capable of growth at a pH lower than about 5, about 4, about 3, or about 2.5) and towards organic and/or a high tolerance to elevated temperatures.

Further the invention relates to a process for the fermentation of a substrate to produce a fermentation product with an eukaryotic cell as described herein, in the wine industry, wherein the glycerol yield is at least 5%, at least 10% or at least 10%, at least 20% or at least 30% higher than that of a process with the corresponding wild-type eukaryotic cell. In an embodiment of such process, the ethanol yield is not increased or decreased, compared to that of a process with the corresponding wild-type eukaryotic cell.

Any of the above characteristics or activities of a eukaryotic cell may be naturally present in the cell or may be introduced or modified by genetic modification.

Recombinant Expression

The eukaryotic cell is a recombinant cell. That is to say, a eukaryotic cell comprises, or is transformed with or is genetically modified with a nucleotide sequence that does not naturally occur in the cell in question.

Techniques for the recombinant expression of enzymes in a cell, as well as for the additional genetic modifications of a eukaryotic cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635 574, WO 98/46772, WO 99/60102, WO 00/37671, WO90/14423, EP-A-0481008, EP-A-0635574 and U.S. Pat. No. 6,265,186.

Bioproducts Production

Over the years suggestions have been made for the introduction of various organisms for the production of bio-ethanol from crop sugars. In practice, however, all major bio-ethanol production processes have continued to use the eukaryotic cells of the genus *Saccharomyces* as ethanol producer. This is due to the many attractive features of *Saccharomyces* species for industrial processes, i. e., a high acid-, ethanol- and osmo-tolerance, capability of anaerobic growth, and of course its high alcoholic fermentative capacity. Preferred eukaryotic cell species as host cells include *S. cerevisiae, S. bulderi, S. barnetti, S. exiguus, S. uvarum, S. diastaticus, K. lactis, K. marxianus* or *K. fragilis*.

A eukaryotic cell may be a cell suitable for the production of ethanol. A eukaryotic cell may, however, be suitable for the production of fermentation products other than ethanol Such non-ethanolic fermentation products include in principle any bulk or fine chemical that is producible by a eukaryotic microorganism such as a eukaryotic cell or a filamentous fungus.

A preferred eukaryotic cell for production of non-ethanolic fermentation products is a host cell that contains a genetic modification that results in decreased alcohol dehydrogenase activity Lignocellulose Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes, The conversion with the cellulases may be executed at ambient temperatures or at higher tempatures, at a reaction time to release sufficient amounts of sugar(s). The result of the enzymatic hydrolysis is hydrolyisis product comprising C5/C6 sugars, herein designated as the sugar composition.

The Sugar Composition

The sugar composition used according to the invention comprises glucose and one or more pentose, e.g. arabinose and/or xylose. Any sugar composition may be used in the invention that suffices those criteria. Optional sugars in the sugar composition are galactose and mannose. In a preferred embodiment, the sugar composition is a hydrolysate of one or more lignocellulosic material. Lignocelllulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, *miscanthus*, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

An overview of some suitable sugar compositions derived from lignocellulose and the sugar composition of their hydrolysates is given in table 15. The listed lignocelluloses include: corn cobs, corn fiber, rice hulls, melon shells, sugar beet pulp, wheat straw, sugar cane bagasse, wood, grass and olive pressings.

TABLE 15

Overview of sugar compositions from lignocellulosic materials.

| Lignocellulosic material | Gal | Xyl | Ara | Man | Glu | Rham | Sum | %. Gal. |
|---|---|---|---|---|---|---|---|---|
| Corn cob a | 10 | 286 | 36 | | 227 | 11 | 570 | 1.7 |
| Corn cob b | 131 | 228 | 160 | | 144 | | 663 | 19.8 |
| Rice hulls a | 9 | 122 | 24 | 18 | 234 | 10 | 417 | 2.2 |
| Rice hulls b | 8 | 120 | 28 | | 209 | 12 | 378 | 2.2 |
| Melon Shells | 6 | 120 | 11 | | 208 | 16 | 361 | 1.7 |
| Sugar beet pulp | 51 | 17 | 209 | 11 | 211 | 24 | 523 | 9.8 |
| Wheat straw Idaho | 15 | 249 | 36 | | 396 | | 696 | 2.2 |
| Corn fiber | 36 | 176 | 113 | | 372 | | 697 | 5.2 |
| Cane Bagasse | 14 | 180 | 24 | 5 | 391 | | 614 | 2.3 |
| Corn stover | 19 | 209 | 29 | | 370 | | 626 | |
| Athel (wood) | 5 | 118 | 7 | 3 | 493 | | 625 | 0.7 |
| *Eucalyptus* (wood) | 22 | 105 | 8 | 3 | 445 | | 583 | 3.8 |
| CWR (grass) | 8 | 165 | 33 | | 340 | | 546 | 1.4 |
| JTW (grass) | 7 | 169 | 28 | | 311 | | 515 | 1.3 |
| MSW | 4 | 24 | 5 | 20 | 440 | | 493 | 0.9 |
| Reed Canary Grass Veg | 16 | 117 | 30 | 6 | 209 | 1 | 379 | 4.2 |
| Reed Canary Grass Seed | 13 | 163 | 28 | 6 | 265 | 1 | 476 | 2.7 |
| Olive pressing residu | 15 | 111 | 24 | 8 | 329 | | 487 | 3.1 |

Gal = galactose, Xyl = xylose, Ara = arabinose, Man = mannose, Glu = glucose, Rham = rhamnose.
The percentage galactose (% Gal) and literature source is given.

It is clear from table 15 that in these lignocelluloses a high amount of sugar is present in the form of glucose, xylose, arabinose and galactose. The conversion of glucose, xylose, arabinose and galactose to fermentation product is thus of great economic importance. Also mannose is present in some lignocellulose materials be it usually in lower amounts than the previously mentioned sugars. Advantageously therefore also mannose is converted by the eukaryotic cell.

It is expected that eukaryotic cells of the present invention can be further manipulated to achieve other desirable characteristics, or even higher overall ethanol yields.

Selection of improved eukaryotic cells by passaging the eukaryotic cells on medium containing hydrolysate has resulted in improved eukaryotic cell with enhanced fermentation rates. Using the teachings of the present invention, one could readily such improved strains.

By pentose-containing material, it is meant any medium comprising pentose, whether liquid or solid. Suitable pentose-containing materials include hydrolysates of polysaccharide or lignocellulosic biomass such as corn hulls, wood, paper, agricultural byproducts, and the like.

By a "hydrolysate" as used herein, it is meant a polysaccharide that has been depolymerized through the addition of water to form mono and oligosaccharide sugars. Hydrolysates may be produced by enzymatic or acid hydrolysis of the polysaccharide-containing material.

Preferably, the eukaryotic cell is able to grow under conditions similar to those found in industrial sources of pentose. The method of the present invention would be most economical when the pentose-containing material can be inoculated with the eukaryotic cell variant without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. The examples below describe the fermentation of pentose in acid hydrolysates (or sulfite waste liquor) of hard woods and soft woods by the eukaryotic cells of the present invention. It is reasonably expected that eukaryotic cell strains capable of growing in sulfite waste liquor could grow be expected grow in virtually any other biomass hydrolysate.

Propagation

The invention further relates to a process for aerobic propagation of the acetate consuming eukaryotic cell, in particular aerobic propagation of the eukaryotic cell strain.

Propagation is herein any process of eukaryotic cell growth that leads to increase of an initial eukaryotic cell population. Main purpose of propagation is to increase a eukaryotic cell population using the eukaryotic cell's natural reproduction capabilities as living organisms. There may be other reasons for propagation, for instance, in case dry eukaryotic cell is used, propagation is used to rehydrate and condition the eukaryotic cell, before it is grown. Fresh eukaryotic cell, whether active dried eukaryotic cell or wet cake may be added to start the propagation directly.

The conditions of propagation are critical for optimal eukaryotic cell production and subsequent fermentation, such as for example fermentation of lignocellulosic hydrolysate into ethanol. They include adequate carbon source, aeration, temperature and nutrient additions. Tank size for propagation and is normally between 2 percent and 5 percent of the (lignocellulosic hydrolysate to ethanol) fermentor size.

In the propagation the eukaryotic cell needs a source of carbon. The source of carbon may herein comprise glycerol, ethanol, acetate and/or sugars (C6 and C5 sugars). Other carbon sources may also be used. The carbon source is needed for cell wall biosynthesis and protein and energy production.

Propagation is an aerobic process, thus the propagation tank must be properly aerated to maintain a certain level of dissolved oxygen. Adequate aeration is commonly achieved by air inductors installed on the piping going into the propagation tank that pull air into the propagation mix as the tank fills and during recirculation. The capacity for the propagation mix to retain dissolved oxygen is a function of the amount of air added and the consistency of the mix, which is why water is often added at a ratio of between 50:50 to 90:10 mash to water. "Thick" propagation mixes (80:20 mash-to-water ratio and higher) often require the addition of compressed air to make up for the lowered capacity for retaining dissolved oxygen. The amount of dissolved oxygen in the propagation mix is also a function of bubble size, so some ethanol plants add air through spargers that produce smaller bubbles compared to air inductors. Along with lower glucose, adequate aeration is important to promote aerobic respiration, which differs from the comparably anaerobic environment of fermentation. One sign of inadequate aeration or high glucose concentrations is increased ethanol production in the propagation tank.

Generally during propagation, eukaryotic cell requires a comfortable temperature for growth and metabolism, for instance the temperature in the propagation reactor is between 25-40 degrees Celcius. Generally lower temperatures result in slower metabolism and reduced reproduction, while higher temperatures can cause production of stress compounds and reduced reproduction. In an embodiment the propagation tanks are indoors and protected from the insult of high summer or low winter temperatures, so that maintaining optimum temperatures of between within the range of 30-35 degrees C. is usually not a problem.

Further propagation may be conducted as propagation of eukaryotic cell is normally conducted.

Fermentation

The invention relates to a process for the fermentation of a eukaryotic cell according to the invention, wherein there is an improved yield of glycerol, which is advantageous in the wine industry. It also may result in increased reduction of acetate level and/or increased yield of fermentation product, e.g. ethanol, which is advantageous in the biofuel industry.

In an embodiment, the eukaryotic cell according to the invention may be a pentose and glucose fermenting eukaryotic cell, including but not limited to such cells that are capable of anaerobic simultaneous pentose and glucose consumption. In an embodiment of the process the pentose-containing material comprises a hydrolysate of ligno-cellulosic material. The hydrolysate may be an enzymatic hydrolysate of ligno-cellulosic material.

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, malic acid, fumaric acid, an amino acid and ethylene.

The fermentation process is preferably run at a temperature that is optimal for the cell. Thus, for most eukaryotic cells or fungal host cells, the fermentation process is performed at a temperature which is less than about 50° C., less than about 42° C., or less than about 38° C. For eukaryotic cell or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

The fermentation process according to the present invention may be run under aerobic and anaerobic conditions. In an embodiment, the process is carried out under micro-aerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention may comprise recovery of the fermentation product.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as eukaryotic cells are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 gl/L-200 g/L, 40 g/L-200 g/L, 50 g/L-200 g/L, 60 g/L-200 g/L, 70 g/L-200 g/L, 80 g/L-200 g/L, 90 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical mamimum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in eukaryotic cell 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

Similar calculation may be made for C5/C6 fermentations, in which in addition to glucose also pentoses are included e.g. xylose and/or arabinose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps g/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:

a. degrading lignocellulose using a method as described herein; and b. fermenting the resulting material, thereby to prepare a fermentation product.

Fermentation Product

The fermentation product of the invention may be any useful product. In one embodiment, it is a product selected from the group consisting of ethanol, n-butanol, 2-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol. In an embodiment in addition to the recovery of fermentation product, the yeast may be recycled.

The following non-limiting examples are intended to be purely illustrative.

EXAMPLES

Example 1

1. Materials and Methods 1.1. Strains and Maintenance

All S. cerevisiae strains used in this appl. (Table 16) are based on the CEN.PK lineage (van Dijken et al. 2000). Stock cultures of S. cerevisiae were propagated in synthetic medium (Verduyn et al. 1992), or YP medium (10 g $L^{-1}$ Bacto yeast extract, 20 g $L^{-1}$ Bacto peptone). 20 g $L^{-1}$ glucose was supplemented as carbon source in the above media. Stock cultures of E. coli DH5a were propagated in LB medium (10 g $L^{-1}$ Bacto tryptone, 5 g $L^{-1}$ Bacto yeast extract, 5 g $L^{-1}$ NaCl), supplemented with 100 µg $ml^{-1}$ ampicillin or 50 µg $ml^{-1}$ kanamycin. Frozen stocks of strains were stored at −80° C., after addition of 30% v/v glycerol to stationary phase cultures.

TABLE 16

S. cerevisiae strains used in this study.

| Strain name | Relevant Genotype | Origin |
|---|---|---|
| CEN.PK113-7D | MATa MAL2-8ᶜ SUC2 | P. Kötter |
| IMX585 | MATa MAL2-8c SUC2 can1::cas9-natNT2 | Maris et al. 2015 |
| IMK643 | MATa MAL2-8c SUC2 can1::cas9-natNT2 gnd2Δ | This appl. |
| IMX705 | MATa MAL2-8c SUC2 can1::cas9-natNT2 gnd2Δ gnd1::gndA | This appl. |
| IMX706 | MATa MAL2-8c SUC2 can1::cas9-natNT2 gnd2Δ gnd1::6pgdh | This appl. |
| IMX707 | MATa MAL2-8c SUC2 can1::cas9-natNT2 gnd2Δ gnd1:gox1705 | This appl. |
| IMX756 | MATa MAL2-8c SUC2 can1::cas9-natNT2 gnd2Δ gnd1::gndA ald6Δ | This appl. |
| IMX817 | MATa MAL2-8c SUC2 can1::cas9-natNT2 gnd2Δ gnd1::gndA ald6Δ gpd2::eutE | This appl. |
| IMX860 | MATa MAL2-8c SUC2 can1::cas9-natNT2 gnd2Δ gnd1::gndA ald6Δ gpd2::eutE gpd1Δ | This appl. |
| IMX883 | MATa MAL2-8c SUC2 can1:cas9-natNT2 gpd2::eutE | This appl. |
| IMX888 | MATa MAL2-8c SUC2 can1:cas9-natNT2 gpd2::eutE gpd1Δ | This appl. |
| IMX899 | MATα MAL2-8c SUC2 can1::cas9-natNT2 ald6Δ | This appl. |

1.2. Plasmid and Cassette Construction

Yeast genetic modifications were performed using the chimeric CRISPR/Cas9 genome editing system (DiCarlo et al. 2013). Plasmid pMEL11 (Mans et al. 2015) was used for single deletions of GND1, GND2 and ALD6. Plasmid pROS11 (Mans et al. 2015) was used for single deletions of GPD1 and GPD2. Unique CRISPR/Cas9 target sequences in each gene were identified based on the sequence list provided by (DiCarlo et al. 2013). Primers that are used herein are SEQ ID NO's 10-46, with their primer no. 's given. The plasmid backbone of pMEL11 and pROS11 were PCR amplified using primer combinations 5792-5980 and 5793-5793 respectively (Sigma-Aldrich). Plasmid insert sequences, expressing the 20 bp gRNA targeting sequence, were obtained by PCR with primer combinations 5979-7365 for GND1, 5979-7231 for GND2 and 5979-7610 for ALD6 using pMEL11 as a template. Insert sequences expressing the gRNA sequences targeting GPD1 and GPD2 were obtained by PCR using primer combinations 6965-6965 and 6966-6966 respectively, with pROS11 as template. PCR amplifications for the construction of all plasmids and cassettes were performed using Phusion® Hot Start II High Fidelity DNA Polymerase (Thermo Scientific, Waltham, Mass.), according to the manufacturer's guidelines. In cases where plasmids were pre-assembled the Gibson Assembly® Cloning kit (New England Biolabs, MA) was used; reactions were performed according to the supplier's protocol (downscaled to 10 µl). The assembly was enabled by homologous sequences at the 5' and 3' ends of the generated PCR fragments. The assembly of the pMEL11 backbone and the insert sequences coding for the gRNAs targeting GND1 and GND2 yielded plasmids pUDR122 and pUDR123 respectively. In each case 1 µl of the Gibson Assembly Mix was used for electroporation of E. coli DH5a cells in a Gene PulserXcell Electroporation System (Biorad). Plasmids were re-isolated from E. coli cultures using a Sigma Gen-Elute Plasmid kit (Sigma-Aldrich). Validation of the plasmids was performed by diagnostic PCR (Dreamtaq®, Thermo Scientific) or restriction analysis. A complete list of all plasmids used can be found in Table 17. The ALD6, GPD1 and GPD2 gRNA expressing plasmids were not pre-assembled; the backbone and insert fragments were transformed directly to yeast and the plasmids were assembled in vivo in each case.

Sequences of *Methylobacillus flagellatus* KT gndA (AF167580_1), *Gluconobacter oxydans* 621H gox1705 (AAW61445.1) and *Bradyrhizobium japonicum* USDA 110 6pgdh were codon optimized based on the codon composition of highly expressed glycolytic genes. In the case of *B. japonicum* the sequence of 6pgdh was obtained by aligning its translated genomic sequence (NC_004463.1) with the other two proteins (45% and 57% similarity respectively). Yeast integration cassettes of the above genes were flanked by the promoter of TP/1 and the terminator of CYC1. The complete cassettes, including promoter, gene and terminator sequences, were synthesized by GeneArt GmbH (Regensburg, Germany) and delivered in pMK-RQ vectors (GeneArt). After cloning in *E. coli* the plasmids were re-isolated and used as templates for PCR amplification of the integration cassettes. The integration cassettes TPI1p-gndA-CYC1t, TPI1p-6pgdH-CYC1t and TPI1p-gox1705-CYC1t were obtained by PCR using primer combination 7380-7381 and plasmids pMK-RQ-gndA, pMK-RQ-6pgdH and pMK-RQ-gox1705 respectively as templates. For the gox1705 protein the $K_m$ NADP+ is 440 µM and $K_m$ NAD+ is 64 µM, so that the ratio $K_m$ NADP+/$K_m$ NAD+=6.88. The gox1705 protein is NAD+ dependent.

A *S. cerevisiae* codon pair optimized eutE was obtained from pBOL199 by XhoI1SpeI restriction cut and ligated in pAG426GPD-ccdB (Addgene, Cambridge, Mass.), yielding the multi-copy plasmid pUDE197. For integration cassette preparation a SacIIEagI cut pRS406 (Addgene, Cambridge, Mass.) was used as plasmid backbone and ligated with the cassette of TDH3p-eutE-CYC1t obtained by same restriction pattern from pUDE197, yielding plasmid pUDI076.

The integration cassette TDH3p-eutE-CYC1t was obtained using primer combination 7991-7992 and plasmid pUDI076 as template. The above primers were designed to add 60 bp of DNA sequence on the 5' and 3' ends of the PCR products, corresponding to the sequences directly upstream and downstream of the open reading frame of the targeted loci in the genome of *S. cerevisiae*. The TPI1p-gndA-CYC1t, TPI1p-6pgdH-CYC1t and TPI1p-gox1705-CYC1t expressing cassettes were targeted to the locus of GND1 and the TDH3p-eutE-CYC1t cassette was targeted to the locus of GPD2.

TABLE 17

Plasmids used in this study.

| Name | Characteristics | Origin |
|---|---|---|
| pBOL199 | Delivery vector, p426-TDH3p-eutE | (Müller et al. 2010) |
| pMEL11 | 2 µm ori, amdS, SNR52p-gRNA.CAN1.Y-SUP4t | (Mans et al. 2015) |
| pROS11 | AmdSYM-gRNA.CAN1-2mu-gRNA.ADE2 | (Mans et al. 2015) |
| pUDE197 | 2 µm ori, p426-TDH3p-eutE-CYC1t | This appl. |
| pUDI076 | pRS406-TDH3p-eutE-CYC1t | This appl. |
| pUDR122 | 2 µm ori, amdS, SNR52p-gRNA.GND2.Y-SUP4t | This appl. |
| pUDR123 | 2 µm ori, amdS, SNR52p-gRNA.GND1.Y-SUP4t | This appl. |
| pMK-RQ-gndA | Delivery vector, TPI1p-gndA-CYC1t | GeneArt, Germany |
| pMK-RQ-6pgdH | Delivery vector, TPI1p-6pgdh-CYC1t | GeneArt, Germany |
| pMK-RQ-gox1705 | Delivery vector, TPI1p-gox1705-CYC1t | GeneArt, Germany |

1.3. Strain Construction

Yeast transformations were performed using the lithium acetate method (Gietz and Woods, 2002). Selection of mutants was performed on synthetic medium agar plates (2% Bacto Agar, Difco) (Verduyn et al. 1992) supplemented with 20 g $L^{-1}$ glucose and with acetamide as the sole nitrogen source, as described in (Solis-Escalante et al. 2013). In each case, confirmation of successful integrations was performed by diagnostic PCR using primer combinations binding outside the targeted loci as well as inside the ORFs of the integrated cassettes. Plasmid recycling after each transformation was executed as described in (Solis-Escalante et al. 2013).

Strain IMK643 was obtained by markerless CRISPR/Cas9 based knockout of GND2 by co-transformation of the gRNA expressing plasmid pUDR123 and the repair oligo nucleotides 7299-7300. The TPI1p-gndA-CYC1t, TPI1p-6pgdH-CYC1t and TPI1p-gox1705-CYC1t integration cassettes were transformed to IMK643, along with the gRNA expressing plasmid pUDR122, yielding strains IMX705, IMX706 and IMX707 respectively. Co-transformation of the pMEL11 backbone, the ALD6 targeting gRNA expressing plasmid insert and the repair oligo nucleotides 7608-7609 to strains IMX705 and IMX585 yielded strains IMX756 and IMX899 respectively, in which ALD6 was deleted without integration of a marker. Co-transformation of the pROS11 backbone, the GPD2 targeting gRNA expressing plasmid insert and the TDH3p-eutE-CYC1t integration cassette to strains IMX756 and IMX585 yielded strains IMX817 and IMX883 respectively. Markerless deletion of GPD1 in strains IMX817 and IMX883 was performed by co-transformation of the pROS11 backbone, the GPD1 targeting gRNA expressing plasmid insert and the repair oligo-nucleotides 6967-6968, yielding strains IMX860 and IMX888 respectively.

1.4. Cultivation and Media

Aerobic shake flask cultivations were performed in 500 ml flasks containing 100 ml of synthetic minimal medium (Verduyn et al. 1992), supplemented with 20 g $L^{-1}$ glucose. The pH value was adjusted to 6 by addition of 2 M KOH before sterilisation by autoclaving at 120° C. for 20 min. Glucose solutions were autoclaved separately at 110° C. for 20 min and added to the sterile flasks. Vitamin solutions were filter sterilized and added to the sterile flasks separately. Cultures were grown at 30° C. and 200 rpm. Initial pre-culture shake flasks were inoculated from frozen stocks in each case. After 8-12 h, fresh pre-culture flasks were inoculated from the initial flasks. Cultures prepared this way were used in aerobic shake flask experiments or as inoculum for anaerobic fermentations. Bioreactors were inoculated to an OD value of 0.2-0.3 from exponentially growing pre-culture flasks. Anaerobic batch fermentations were performed in 2 L Applikon bioreactors (Applikon, Schiedam, NL), with a 1 L working volume. All anaerobic batch fermentations were performed in synthetic minimal medium (20 g $L^{-1}$ glucose), prepared in the same way as the flask media. Anaerobic growth media were additionally supplemented with 0.2 g $L^{-1}$ sterile antifoam C (Sigma-Aldrich), ergosterol (10 mg $L^{-1}$) and Tween 80 (420 mg $L^{-1}$), added separately. Fermentations were performed at 30° C. and stirred at 800 rpm. Nitrogen gas (<10 ppm oxygen) was used for sparging (0.5 L $min^{-1}$). Fermentation pH was maintained at 5 by automated addition of 2M KOH. Bioreactors were equipped with Nonprene tubing and Viton O-rings to minimize oxygen diffusion in the medium. All fermentations were performed in duplicate.

1.5. Analytical Methods

Determination of optical density at 660 nm was done using a Libra S11 spectrophotometer (Biochrom, Cambridge, UK). Off-gas analysis, dry weight measurements and HPLC analysis of culture supernatant, including corrections for ethanol evaporation, were performed as described in (Medina et al. 2010).

1.6. Enzymatic Activity Determination

Preparation of cell free extracts for in vitro determination of enzymatic activities was executed as described previously (Kozak et al. 2014). Assays were performed at 30° C.; enzymatic activity was measured by monitoring the reduction of $NAD^+/NADP^+$ (for 6PGDH) or oxidation of NADH at 340 nm (for EutE). The $NADP^+$ linked glucose-6-phosphate dehydrogenase activity assay mix contained 50 mM Tris-HCl (pH 8.0), 5 mM of $MgCl_2$, 0.4 mM of $NADP^+$ and 50 or 100 µl of cell extract in a total volume of 1 ml. The reaction was started by addition of 5 mM of glucose-6-phosphate. The $NAD^+/NADP^+$ linked 6-phosphogluconate dehydrogenase activity assay mixes contained 50 mM Tris-HCl (pH 8.0), 5 mM of $MgCl_2$, 0.4 mM of $NAD^+/NADP^+$ respectively and 50 or 100 µl of cell extract in a total volume of 1 ml. Reactions were started by addition of 5 mM of 6-phosphogluconate. All assays were performed in duplicate and reaction rates were proportional to the amount of cell extract added.

1.7 Expression of a Heterologous $NAD^+$ Dependent 6-Phosphogluconate Dehydrogenase To change the co-factor specificity of 6-phosphogluconate dehydrogenase from $NADP^+$ to $NAD^+$ GND1 and GND2, encoding for the major and the minor isoform of the enzyme in S. cerevisiae respectively, were deleted. Heterologous genes encoding for $NAD^+$ dependent (M. flagellatus and B. japonicum) or $NAD^+$ preferring (G. oxydans) enzymes were codon optimized for expression in S. cerevisiae and integrated in the locus of GND1, under the control of the strong constitutive promoter of TPI1. Growth experiments performed in aerobic synthetic medium shake flasks (20 g $L^{-1}$ glucose) with the engineered strains did not indicate a significant effect of the overexpression of the heterologous genes on the maximum specific growth rate compared to the parental strain IMX585 (growth rate was app. 95% of the parental strain), with the exception of IMX706, expressing the enzyme from B. japonicum (Table 18).

TABLE 18

Average specific growth rates (μ) obtained in aerobic synthetic medium shake flasks (pH 6) containing 20 g L$^{-1}$ glucose (experiments performed in duplicate, mean deviations from duplicates are indicated), 30° C., 200 rpm.

| Strain | Relevant genotype | Average μ (h$^{-1}$) |
|---|---|---|
| IMX585 | GND1 GND2 | 0.38 ± 0.01 |
| IMX705 | gnd2Δ gnd1: gndA | 0.36 ± 0.00 |
| IMX706 | gnd2Δ gnd1::6pgdh | 0.28 ± 0.01 |
| IMX707 | gnd2Δ gnd1:gox1705 | 0.36 ± 0.00 |

Figure 1:
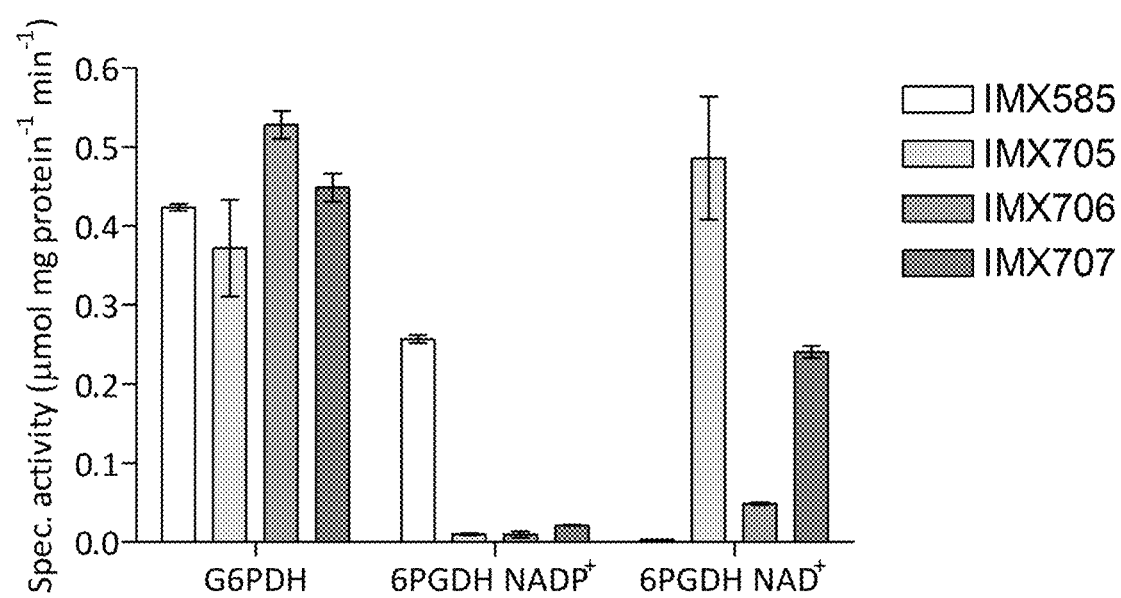
FIG. 1 shows in vitro specific enzymatic activities of cell free extracts from exponentially growing shake flask cultures, harvested at OD (Optical density is herein measured at 660 nm, and abbreviated as "OD")=4 to 5. Cultures were grown in synthetic medium supplemented with 20 g $L^{-1}$ glucose, pH 6, 30° C., 200 rpm. Indicated are: Glucose-6-phosphate dehydrogenase activity, $NADP^+$ dependent 6-phosphogluconate dehydrogenase activity, $NAD^+$ dependent 6-phosphogluconate dehydrogenase activity are given for four strains:IMX585 (white bars, left), IMX705 (light grey bars), IMX706 (middle grey bars) and IMX707 (dark grey bars, right). Data from independent duplicate experiments, error bars indicate mean deviations of the duplicates.

To investigate functional expression of the heterologous 6-phosphogluconate dehydrogenase enzymes in *S. cerevisiae* enzymatic assays were performed in cell free extracts, prepared from exponentially growing aerobic shake flask cultures of the engineered strains (harvested at OD 4-5). Assays were performed for quantification of glucose-6-phosphate dehydrogenase activity, as well as NAD$^+$ and NADP$^+$ dependent 6-phosphogluconate dehydrogenase activities. Determination of glucose-6-phosphate dehydrogenase activity was performed as a quality check of the cell free extracts, the enzymatic activity determinations demonstrated functional glucose-6-phosphate dehydrogenase and 6-phosphogluconate dehydrogenase in all generated strains (FIG. 1). All engineered strains showed high NAD$^+$ and low residual NADP$^+$ dependent 6PGDH activities, in line with the expected functional expression of the heterologous enzymes and deletion of GND1 and GND2. Strain IMX705, expressing gndA from *Methylobacillus flagellatus*, showed the highest in vitro NAD$^+$-dependent 6-phosphogluconate dehydrogenase activity (0.49±0.1 μmol mg biomass$^{-1}$ min$^{-1}$).

Furthermore, all engineered strains showed a significant increase in the ratio of NAD$^+$/NADP$^+$ linked 6-phosphogluconate dehydrogenase activities when compared to the control strain IMX585 (Table 18). In addition to the highest in vitro NAD$^+$-dependent 6-phosphogluconate dehydrogenase activity, strain IMX705 also showed the highest ratio of all engineered strains (46±10).

TABLE 18A

NAD$^+$/NADP$^+$ linked specific 6-phosphogluconate dehydrogenase activity ratios of cell free extracts from exponentially growing shake flask cultures, harvested at OD = 4 to 5. Cultures were grown in synthetic medium supplemented with 20 g L$^{-1}$ glucose, pH 6, 30° C., 200 rpm. Data from independent duplicate experiments, error bars indicate mean deviations of the duplicates.

| Strain | Relevant genotype | NAD$^+$/NADP$^+$ linked activity ratio |
|---|---|---|
| IMX585 | GND1 GND2 | <0.01 |
| IMX705 | gnd2Δ gnd1:: gndA | 46 ± 10 |
| IMX706 | gnd2Δ gnd1::6pgdh | 5 ± 0.2 |
| IMX707 | gnd2Δ gnd1:gox1705 | 11 ± 0.5 |

The enzymatic assay results pointed towards the strain expressing gndA being the best performing strain; for this reason strain IMX705 was characterized further.

1.8 Anaerobic Batch Experiments

Results from the enzymatic assays pointed towards a successful co-factor specificity change of 6-phosphogluconate dehydrogenase from NADP$^+$ to NAD$^+$.

Figure 2:
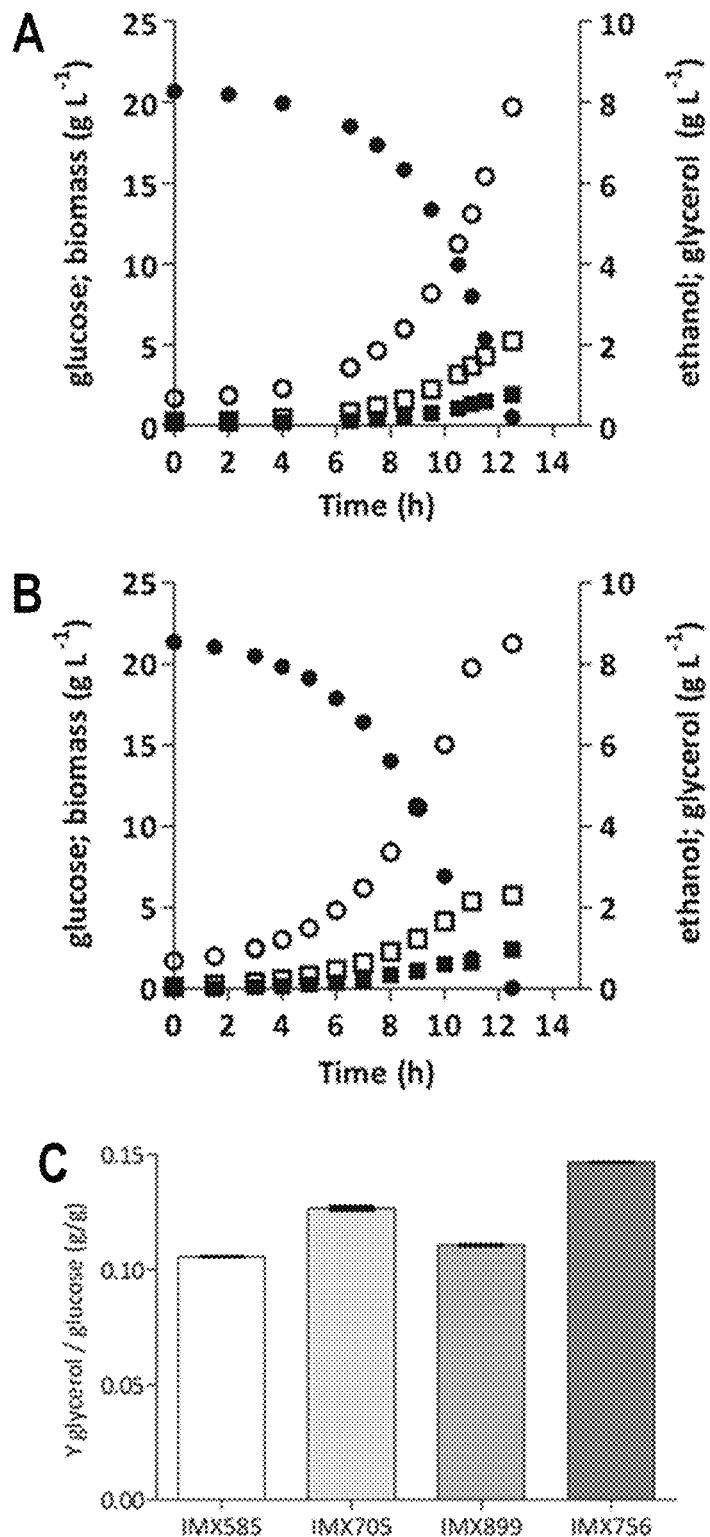
FIG. 2 shows fermentation profiles of IMX585 (FIG. 2A), IMX705 (FIG. 2D), IMX899 (FIG. 2B), and IMX756 (FIG. 2E). Glucose=filled circles, biomass=filled squares, glycerol=open squares, ethanol=open circles. Fermentations were performed in synthetic medium supplemented with 20 g L$^{-1}$ glucose. Batches performed at pH 5, sparging of 500 ml min$^{-1}$ N2, 30° C. Biomass was calculated by converting OD values throughout the fermentation to biomass based on an OD to biomass conversion formula derived from plotting actual biomass samples against OD during mid-exponential phase. Glycerol yield on glucose from anaerobic batch fermentations performed with IMX585, IMX705, IMX899, IMX756 are shown in FIG. 2C. Ethanol yields on glucose from the same fermentations are shown in FIG. 2F. Calculation of ethanol yields was based on data corrected for evaporation. Data is presented as averages of independent duplicate experiments.
Figure 2:
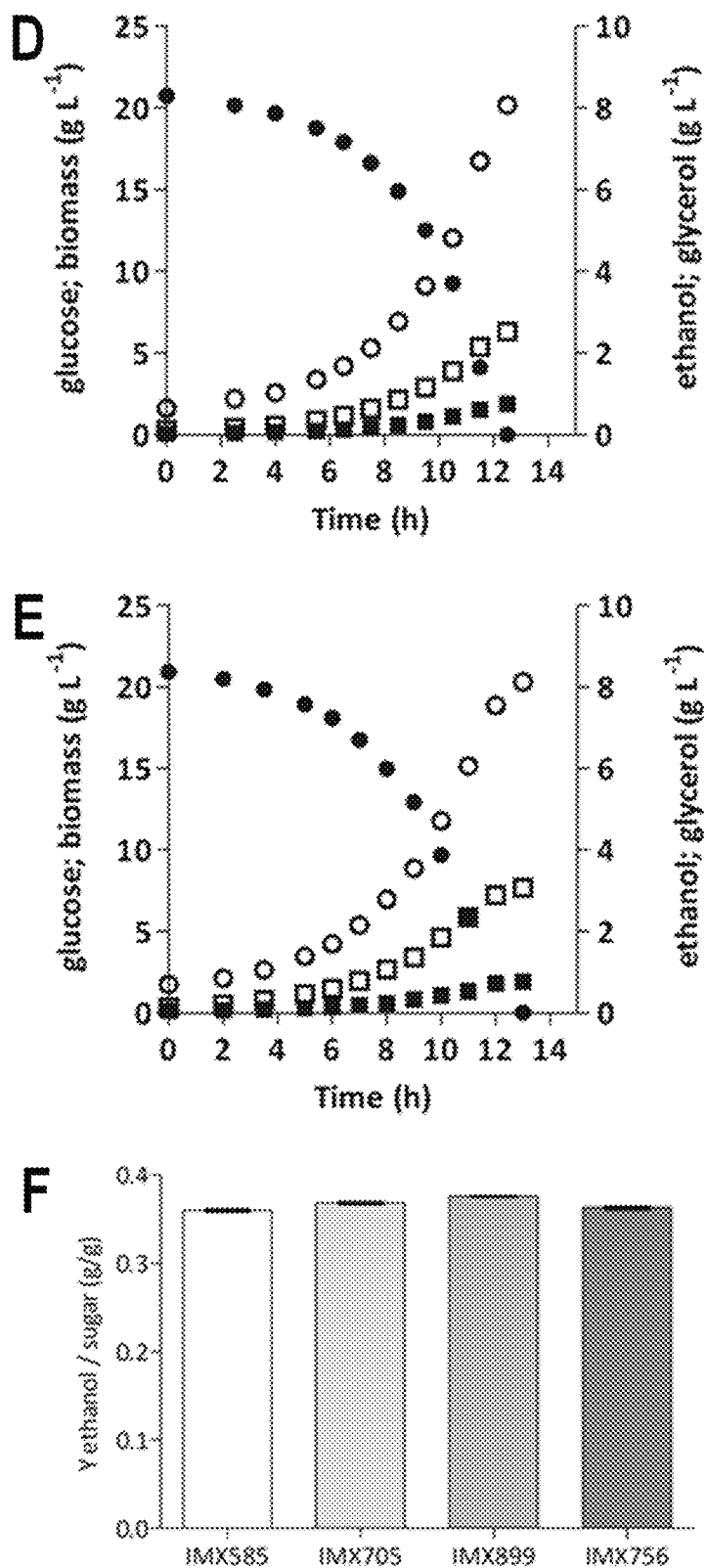

To investigate the effect of the co-factor specificity change of 6-phosphogluconate dehydrogenase on the anaerobic physiology of *S. cerevisiae*, anaerobic batch experiments were performed in bioreactors. Strains IMX585 (GND1 GND2) and IMX705 (gnd2Δ gnd1::gndA) were grown in synthetic medium supplemented with 20 g L$^{-1}$ glucose. The growth rate of the engineered strain IMX705 was similar to the reference strain (ca. 95% of IMX585 (Table 19)). In addition, sugar consumption profiles were comparable, with glucose being exhausted after ca. 12 hours (FIG. 2). The anaerobic batch with strain IMX705 resulted in a 19.8% increased glycerol yield on glucose compared to IMX585 (Table 19). Additionally, the amount of glycerol formed per biomass in the fermentation with strain IMX705 was 24.1% higher than the one with strain IMX585.

Figure 3:
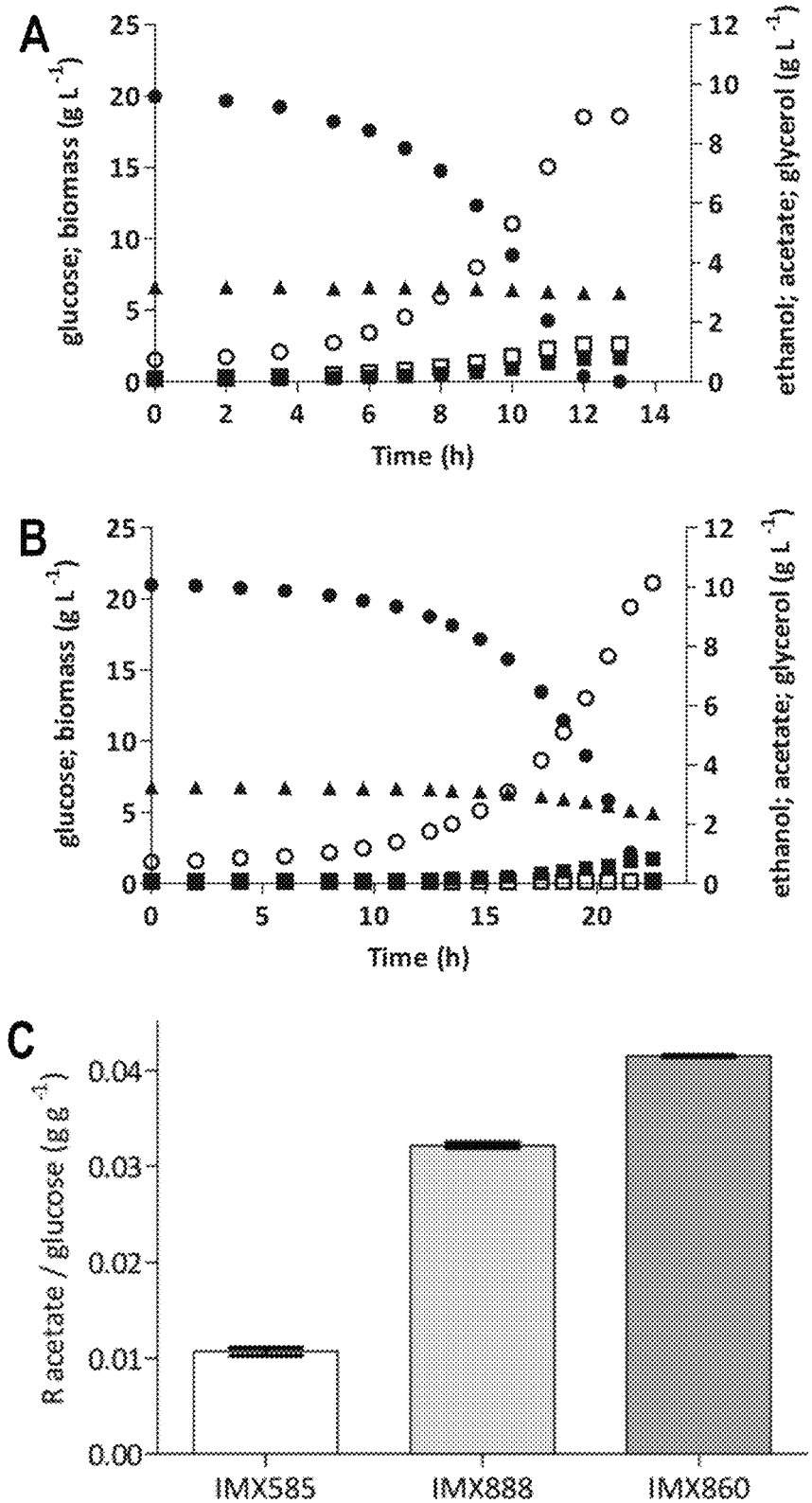
Figure 3:
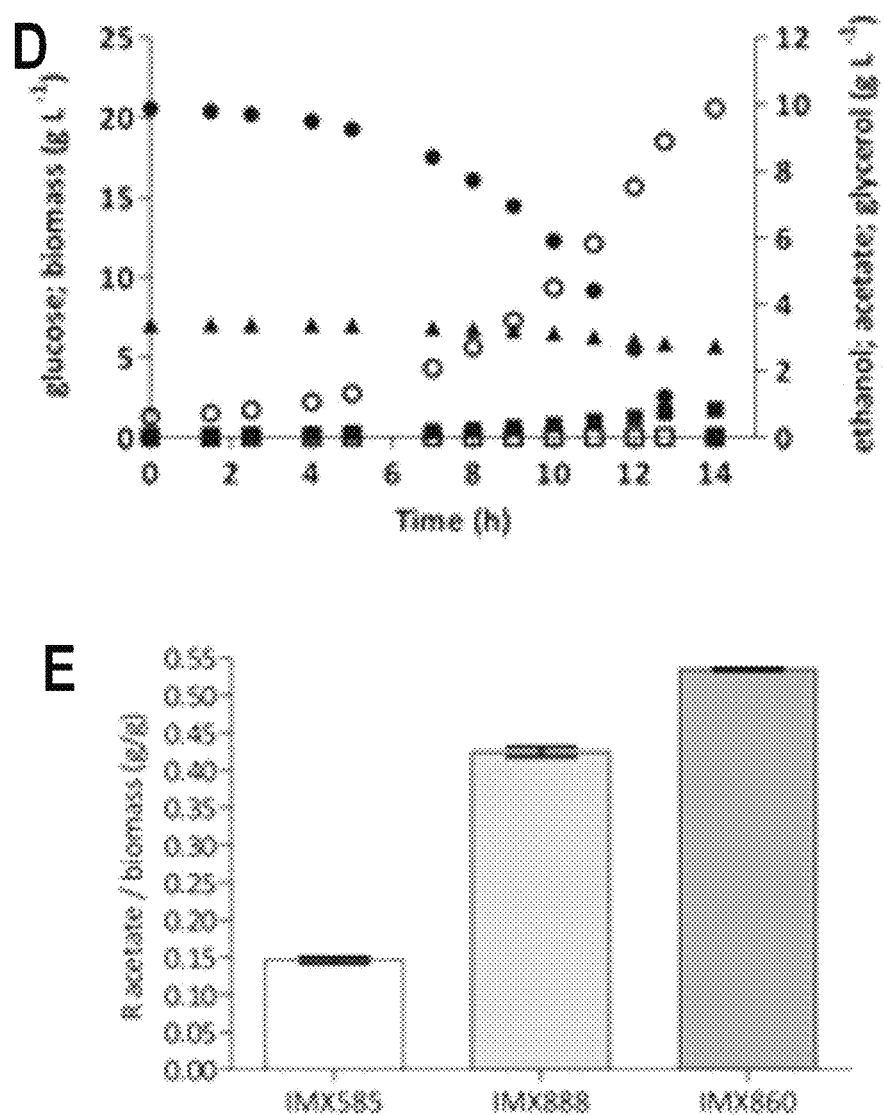

In the anaerobic fermentations of strain IMX705, an increase of ca. 9% in the production of extracellular acetate per biomass formed was observed, compared to the reference strain IMX585 (Table 19). The increase in extracellular acetate could have been a result of up-regulation of the cytosolic NADP$^+$-dependent aldehyde dehydrogenase which catalyses the reaction acetaldehyde+NADP$^+$→acetate+NADPH+H$^+$, encoded by ALD6. Along with the oxidative branch of the pentose phosphate pathway, Ald6p provides another major route for NADPH regeneration in the cytosol of the cells. It has been demonstrated that overexpression of ALD6 in a zwr1Δ strain results in increased growth rates on glucose; furthermore, zwr1Δ ald6Δ double mutants are not viable. Furthermore, in a scenario where the glycerol formation pathway in strain IMX705 has been replaced by the acetate reduction one, Ald6p can interfere with the generation of additional NADH in the cytosol by participating in a ATP driven transhydrogenase-like cycle in the cytosol (FIG. 3). In this cycle, 1 mol acetate is converted to 1 mol acetyl-CoA via the reaction catalysed by Acs1p and Acs2p, at the net expense of 2 mol ATP. The 1 mol acetyl-CoA is then reduced to 1 mol acetaldehyde via the reaction catalysed by acetylating acetaldehyde dehydrogenase, with a concomitant oxidation of 1 mol NADH to NAD$^+$. The 1 mol acetaldehyde can then be oxidized back to 1 mol acetate via Ald6p, with a concomitant reduction of 1 mol of NADP$^+$ to NADPH. In this way both co-factors can be regenerated at the expense of ATP. Removal of the reaction catalysed by Ald6p prevents this potential cycle from taking place.

In wild type strains, the reaction catalysed by Ald6p is important for NADPH generation as well as the formation of acetate, which is a precursor of acetyl-CoA. In the ald6Δ strain IMX756, acetate can potentially be formed by the reactions catalysed by the cytosolic Ald2p and Ald3p or by the mitochondrial Ald4p and Ald5p isoforms. Ald2p and Ald3p are NAD$^+$ dependent and the formation of acetate required for growth through the reactions catalysed by these enzymes will likely result in additional formation of cytosolic NADH. Ald4p can utilize both NAD$^+$ and NADP$^+$ as cofactors. Nicotinamide cofactors cannot generally cross the inner mitochondrial membrane. In anaerobically grown cultures of *S. cerevisiae*, re-oxidation of NADH produced by acetate formation catalysed by Ald4p would require the transfer of reducing equivalents across the mitochondrial membrane. This could for example be accomplished via mitochondrial shuttle systems, such as the acetaldehyde-ethanol shuttle, which transfer reducing equivalents to cytosolic NAD$^+$. The excess cytosolic NADH can then be re-oxidized via increased glycerol formation.

In order to remove the alternative NADPH regeneration route catalysed by Ald6p, ALD6 was deleted in strain IMX705 yielding strain IMX756. We have found a deletion of ALD6 is potentially beneficial to the generation of an acetate consuming strain, as it can remove a potential ATP-driven transhydrogenase like reaction in the cytoplasm of the cells, created by Acs1p/Acs2p, EutEp and Ald6p (FIG. 4). To investigate the effect of Ald6p on the anaerobic physiology of wild type *S. cerevisiae*, ALD6 was also deleted in strain IMX585 yielding strain IMX899.

Strains IMX899 and IMX756 were characterized in anaerobic batch experiments, under the same conditions as the batches performed with strains IMX585 and IMX705. The growth rates of IMX899 and IMX756 were ca. 90% and 81% of the growth rate of reference strain IMX585. Extracellular acetate formation was severely impacted in the early stages of the fermentations, and its concentration dropped to below detection levels in the later stages (data not shown) in fermentations with both strains. The anaerobic batch with strain IMX899 resulted in an increase of 1% in the glycerol yield on glucose and of 5.3% in glycerol formed per biomass compared to the reference strain IMX585 (Table 19A), indicating a minor effect of the deletion in the generation of additional cytosolic NADH. However, the fermentation with strain IMX756, in which the deletion of ALD6 was combined with the overexpression of gndA and the deletions of GND1 and GND2, resulted in an increase of 39% in the glycerol yield on glucose and of 55% in glycerol formed per biomass formed compared to the reference strain IMX585 (Table 19A).

This study provides proof of principle that different heterologous, $NAD^+$ dependent 6-phosphogluconate dehydrogenases can be functionally expressed in *S. cerevisiae*. Furthermore, overexpression of gndA in a gnd1Δ gnd2Δ strain resulted in an increase in glycerol formation per biomass formed, which points to an increase in cytosolic NADH formation per biomass formed. Further deletion of ALD6 in strain IMX705 showed a marked increase of the glycerol yield on glucose, as well as glycerol formation per biomass formed in anaerobic cultures of the mutant strain compared to the control. The engineering strategies caused only a minor decrease in the maximum specific growth rates of the mutant strains. This indicates that this strategy could be directly applied to industrial strains and potentially be used to increase acetic acid consumption in hydrolysates.

TABLE 19

Maximum specific growth rates (μ), major product yields and ratios of glycerol and acetate formation per biomass formed. Data obtained from anaerobic batch fermentations performed in bioreactors, with strains IMX585, IMX705, IMX899 and IMX756. Fermentations were performed in synthetic medium supplemented with 20 g $L^{-1}$ glucose. Batches performed at pH 5, sparging of 500 ml $min^{-1}$ $N_2$, 30° C. Yields and ratios were calculated from data collected in the exponential growth phase, as the slopes of plots of the measured values. Calculation of ethanol yields was based on data corrected for evaporation. Data is presented as averages of independent duplicate experiments.

| | Strain | | |
|---|---|---|---|
| | IMX585 | IMX705 | IMX756 |
| μ ($h^{-1}$) | 0.32 ± 0.00 | 0.30 ± 0.01 | 0.26 ± 0.01 |
| Y glycerol/glucose (g/g) | 0.106 ± 0.001 | 0.130 ± 0.002 | 0.144 ± 0.001 |
| Y biomass/glucose (g/g) | 0.094 ± 0.004 | 0.087 ± 0.002 | 0.083 ± 0.002 |
| Y EtOH/glucose (g/g) | 0.360 ± 0.01 | 0.368 ± 0.01 | 0.363 ± 0.02 |
| Ratio glycerol formed/biomass (g/g) | 1.123 ± 0.04 | 1.394 ± 0.02 | 1.752 ± 0.05 |
| Ratio acetate formed/biomass (g/g) | 0.090 ± 0.002 | 0.098 ± 0.001 | Below detection limit |

With taking ethanol evaporation into the calculation, with mmol instead of g for ratio calculations, and addition of data for IMX899, the data are given in table 19A:

TABLE 19A

| | Strain | | | |
|---|---|---|---|---|
| | IMX585 | IMX705 | IMX899 | IMX756 |
| μ ($h^{-1}$) | 0.32 ± 0.00 | 0.30 ± 0.01 | 0.29 ± 0.01 | 0.26 ± 0.01 |
| Y glycerol/glucose (g $g^{-1}$) | 0.105 ± 0.000 | 0.121 ± 0.001 | 0.106 ± 0.000 | 0.146 ± 0.000 |
| Y biomass/glucose ($g_x$ $g^{-1}$) | 0.094 ± 0.004 | 0.087 ± 0.002 | 0.088 ± 0.001 | 0.083 ± 0.002 |
| Y EtOH/glucose (g $g^{-1}$) | 0.372 ± 0.001 | 0.379 ± 0.001 | 0.386 ± 0.000 | 0.374 ± 0.002 |
| Ratio glycerol formed/biomass (mmol $g_x^{-1}$) | 12.19 ± 0.44 | 15.14 ± 0.22 | 12.83 ± 0.39 | 18.90 ± 0.56 |
| Ratio acetate formed/biomass (mmol $g_x^{-1}$) | 1.50 ± 0.03 | 1.63 ± 0.02 | <0.05 | <0.05 |

Example 2

2.1 Co-Factor Specificity Change of 6PGDH in Combination with the Acetate Reducing Pathway The combined change of the co-factor specificity of 6-phosphogluconate dehydrogenase from $NADP^+$ to $NAD^+$ and deletion of ALD6 in strain IMX756 resulted in a 37.7% increase in the glycerol yield on glucose compared to the control strain IMX585 in anaerobic batch fermentations. This result was in line with the estimated 40.5% increase in glycerol yield on glucose, in the scenario where excess NADH is generated in the cytosol based on the proposed strategy and the glycerol formation pathway is still intact. As the next step, the effect of the replacement of the glycerol formation pathway by the acetate reducing one on the amount of acetate that can be consumed by a strain with IMX756 as parental is investigated.

To replace the glycerol formation pathway by the acetate reduction one, GPD1 and GPD2 (encoding for glycerol-3-phosphate dehydrogenases) were deleted and eutE (encoded for *E. coli* acetylating acetaldehyde dehydrogenase) was overexpressed in strain IMX756, yielding strain IMX860. Furthermore, deletion of GPD1 and GPD2 and overexpression of eutE in IMX585 yielded the acetate reducing control strain IMX888.

In the acetate reducing strain IMX888 the 6-phosphogluconate dehydrogenase is $NADP^+$ dependent. Based on the theoretical analysis conducted herein, a consumption of 5.51 mmol acetate per gram biomass formed is expected for this strain, in anaerobic fermentations with glucose as the carbon source. In strain IMX860, in which the co-factor specificity is changed, a consumption of 8.75 mmol acetate per gram biomass formed is expected.

In this experiment, the effect of the engineering strategy proposed in this scenario in anaerobic acetate consumption is investigated. Strains IMX860 and IMX888 were grown in anaerobic fermentations in bioreactors, supplemented with 20 g $L^{-1}$ glucose and 3 g $L^{-1}$ acetic acid. Sparging, pH control as well as temperature were identical to the batches performed with strains IMX585, IMX705 and IMX756. Based on the theoretical analysis, an increase of 59% in acetate consumed per biomass formed is expected in strain IMX860 compared to IMX888. Furthermore, the engineering strategy in strain IMX860 should result in a theoretical increase of 3% in the ethanol yield on glucose compared to strain IMX888 and 22.4% compared to the wild type scenario. The results are given in Tables 20, 20A and 21. For Table 20A, calculation of acetate consumption increase on glucose and per biomass formed between strains IMX888 (using the Medina et al. 2010 strategy) and strain IMX860 (using the strategy in this example), the apparent consumption of the control strain IMX585 (which does not contain eutE) was subtracted from the calculated values.

TABLE 20

Maximum specific growth rates, major product yields and ratios of acetate consumed on glucose consumed and biomass formed. Data obtained from anaerobic batch fermentations performed in bioreactors with strains IMX585, IMX888 and IMX860. Fermentations were performed in synthetic medium supplemented with 20 g $L^{-1}$ glucose and 3 g $L^{-1}$ acetic acid. Batches performed at pH 5, sparging of 500 ml $min^{-1}$ $N_2$, 30° C. Yields and ratios were calculated from data collected in the exponential growth phase. Calculation of ethanol yields was based on data corrected for evaporation. Data is presented as averages of independent duplicate experiments.

| | Strain | | |
|---|---|---|---|
| | IMX585 | IMX888 | IMX860 |
| $\mu$ ($h^{-1}$) | 0.28 ± 0.01 | 0.26 ± 0.01 | 0.20 ± 0.01 |
| Y glycerol/glucose (g/g) | 0.062 ± 0.000 | N/D | N/D |
| Y biomass/glucose (g/g) | 0.076 ± 0.003 | 0.075 ± 0.000 | 0.077 ± 0.000 |
| Y EtOH/glucose (g/g) | 0.421 ± 0.001 | 0.460 ± 0.001 | 0.466 ± 0.002 |
| Ratio acetate consumed/biomass (g/g) | 0.146 ± 0.006 | 0.424 ± 0.009 | 0.534 ± 0.002 |
| Ratio acetate consumed/glucose (g/g) | 0.009 ± 0.000 | 0.032 ± 0.000 | 0.41 ± 0.000 |

With taking ethanol evaporation into the calculation, and with mmol instead of g for ratio calculations and addition of glycerol/glucose (g $g^{-1}$) data for IMX888 and IMX860, the data are given in table 20A.

TABLE 20A

| | Strain | | |
|---|---|---|---|
| | IMX585 | IMX888 | IMX860 |
| $\mu$ ($h^{-1}$) | 0.28 ± 0.01 | 0.26 ± 0.01 | 0.20 ± 0.01 |
| Y glycerol/glucose (g $g^{-1}$) | 0.060 ± 0.000 | <0.001 | <0.001 |
| Y biomass/glucose ($g_x$ $g^{-1}$) | 0.076 ± 0.003 | 0.075 ± 0.000 | 0.077 ± 0.000 |
| Y EtOH/glucose (g $g^{-1}$) | 0.433 ± 0.001 | 0.474 ± 0.001 | 0.489 ± 0.000 |
| Ratio glycerol produced/biomass (mmol $g_x^{-1}$) | 8.50 ± 0.04 | <0.01 | <0.01 |
| Ratio acetate consumed/biomass (mmol $g_x^{-1}$) | 2.44 ± 0.10 | 6.92 ± 0.12 | 8.90 ± 0.04 |
| Ratio acetate consumed/glucose (g $g^{-1}$) | 0.011 ± 0.00 | 0.032 ± 0.00 | 0.042 ± 0.00 |

2.2. Co-Factor Specificity Change of G6PDH on Generation of Additional Cytosolic NADH and the Acetate Reducing Pathway Recently a $NAD^+$ dependent glucose-6-phosphate dehydrogenase, designated azf, has been characterized in the archaeon *Haloferax volcanii* (Pickl and Schönheit, 2015). In this example the effect of a co-factor change of glucose-6-phosphate dehydrogenase from $NADP^+$ to $NAD^+$ on the generation of additional cytosolic NADH per biomass formed, azf is overexpressed in a *S. cerevisiae* zwf1Δ background. Based on the theoretical analysis and the experiments conducted in this application, an identical theoretical impact as the co-factor change of 6-phosphogluconate dehydrogenase is expected.

The protein sequence of Azfp (ADE03728.1) from *Haloferax volcanii* DS2 is used to generate a yeast codon optimized version of azf, based on the composition of highly expressed glycolytic genes (Wiedemann and Boles, 2008). An overexpression cassette is synthesized, under the control of a strong constitutive glycolytic promoter and cloned in a plasmid. The plasmid is used as template to generate a PCR product in which the overexpression cassette is flanked by 60 bp homologous sequences to the direct upstream and downstream regions of ZWF1. The locus of ZWF1 is then deleted using the CRISPR/Cas9 system with the PCR product as the repair fragment, resulting in a zwf1::azf strain.

Determination of Azfp enzymatic activity in the zwf1::azf strain is performed as described previously (Pickl and Schönheit, 2015). Furthermore, the effect of the replacement of ZWF1 by azf on the aerobic maximum specific growth rate of the engineered strain is be investigated in an identical fashion to the way it was determined for strains IMX705, IMX706 and IMX707 in this application.

The generated zwf1::azf strain is characterized in anaerobic fermentations in bioreactors with 20 g $L^{-1}$ glucose as the carbon source and compared to its parental strain, as well as strain IMX705. The strain is expected to perform similarly to strain IMX705 in terms of glycerol yield on glucose and glycerol formation on biomass formed and have an increase of at least 22.6% on the glycerol yield on glucose compared to its parental, wild type strain.

The zwf1::azf strain is engineered further by deletion of GPD1 and GPD2 and introduction of eutE in the GPD2 locus, using the same steps as the case of the construction of strain IMX888. The relevant genotype of the resulting strain is gpd1Δ gpd2::eutE zwf1::azf.

In follow-up experiments, the effect of the engineering strategy proposed in this scenario on anaerobic acetate consumption is investigated. The gpd1Δ gpd2::eutE zwf1::azf strain is grown in anaerobic fermentations in bioreactors, supplemented with 20 g $L^{-1}$ glucose and 3 g $L^{-1}$ acetic acid. Sparging, pH control as well as temperature is identical to the batches performed with strains IMX585, IMX705 and IMX756. Based on the theoretical analysis and similarly to strain IMX888, an increase of 59% in acetate consumed per biomass formed is expected in this strain compared to the acetate reducing strain IMX860, in which no co-factor change of glucose-6-phosphate dehydrogenase or 6-phosphogluconate dehydrogenase has been made.

2.2 Simultaneous Co-Factor Specificity Change of G6PDH and 6PGDH on Generation of Additional Cytosolic NADH and the Acetate Reducing Pathway To investigate the effect of a simultaneous co-factor change of glucose-6-phosphate dehydrogenase and 6-phosphogluconate dehydrogenase from $NADP^+$ to $NAD^+$ on the generation of additional cytosolic NADH per biomass formed azf and gndA is overexpressed in a zwf1Δ gnd1Δ gnd2Δ strain.

Generation of an azf overexpression cassette is performed as described previously in this application. Strain construction is performed identically to the one described for the zwf1::azf strain. In this case, strain IMX705 is used as parental. The resulting relevant genotype of the generated strain is gnd2Δ gnd1::gndA zwf1::azf.

Determination of Azfp enzymatic activity in the zwf1::azf strain is performed as described previously (Pickl and Schönheit, 2015). Determination of GndAp enzymatic activity is performed as described in this application.

The generated gnd2Δ gnd1::gndA zwf1::azf strain is characterized in anaerobic fermentations in bioreactors with 20 g $L^{-1}$ glucose as the carbon source and compared to its parental strain IMX705, as well as strain IMX585 (no co-factor specificity change). In this scenario NADPH is mainly generated via the Ald6p catalysed reaction. The amount of additional NADH that is generated per biomass formed is determined by the flux of glucose through the oxidative part of the pentose phosphate pathway. In this scenario, assuming 100% specificity for $NAD^+$, the flux through the oxidative part of the pentose phosphate is no longer coupled to NADPH generation. In a scenario where the enzymes preferably use $NAD^+$, but also show activity towards $NADP^+$, the flux through this pathway can still be correlated to NADPH provision. It is expected that the change of the co-factors of both glucose-6-phosphate dehydrogenase and 6-phosphogluconate dehydrogenase will result in an additional increase of formation of cytosolic NADH per biomass formed, when compared to the change of either co-factor alone.

The gnd2Δ gnd1::gndA zwf1::azf strain is engineered further by deletion of GPD1 and GPD2 and introduction of eutE in the GPD2 locus, using the same steps as the case of the construction of strain IMX888. The relevant genotype of the resulting strain is gpd1Δ gpd2::eutE gnd2Δ gnd1::gndA zwf1::azf.

In follow-up experiments, the effect of the engineering strategy proposed in this scenario in anaerobic acetate consumption is investigated. The gpd1Δ gpd2::eutE gnd2Δ gnd1::gndA zwf1::azf strain is grown in anaerobic fermentations in bioreactors, supplemented with 20 g $L^{-1}$ glucose and 3 g $L^{-1}$ acetic acid. Sparging, pH control as well as temperature is identical to the batches performed with strains IMX585, IMX705 and IMX756. An increased acetate consumption per biomass formed compared to strain IMX860 and the gpd1Δ gpd2::eutE zwf1::azf is expected in this case.

The advantages of strains according to the invention, as shown in the examples are summarized in table 21,

TABLE 21

Yield increase for ethanol and glycerol and acetate consumed with theoretically calculated values (between brackets), compared to wild-type strain and for acetate scenario (biofuel) and glycerol scenario (wine).

| | Acetate scenario (bioethanol fuel) compared to strain from Medina et al. 2010 | Glycerol scenario (wine) compared to wild type strain |
|---|---|---|
| Yield Ethanol on glucose Increase in % | 1.3% (3%) | ~0% (−4.5%) |
| Yield glycerol Increase in % | | 38% (40.5%) |
| Acetate consumption (% increase (g acetate/g biomass)) | 28% (59%) | |
| Biomass yield | | −13.2% (−11.5%) |

From table 21 it is clear that substantial advantages may be obtained:

For application in biofuel industry 28% acetate consumption increase and 1.3% increase in ethanol yield is advantageous.

For the application in the wine industry up to 38% increase of glycerol yield and same or lower ethanol production advantageous.

Based on the data and calculations of Tables 19A and 20A, like summary table 21, is below summary table 21A:

TABLE 21A

|  | Acetate scenario (bioethanol fuel) compared to strain from Medina et al. 2010 | Glycerol scenario (wine) compared to wild type strain |
|---|---|---|
| Yield Ethanol on glucose Increase in % | 3% (3%) | ~0.5 (in the error margin) % (−4.5%) |
| Yield glycerol Increase in % | — | 39% (40.5%) |
| Acetate consumption (% increase (mmol acetate/ g biomass)) | 44% (59%) or 31% (59%) (without correction for wild type apparent consumption) | |
| Biomass yield | +2.6% | −11.7 ± 3%%(−11.5%) |

From table 21A it is clear that substantial advantages may be obtained:

For application in biofuel industry 44% acetate consumption increase per gram biomass formed and 3% increase in ethanol yield on glucose is advantageous.

For the application in the wine industry up to 39% increase of glycerol yield and same or lower ethanol production advantageous.

REFERENCES

Medina V G, Almering M J H, Van Maris A J A, Pronk J T. 2010. Elimination of glycerol production in anaerobic cultures of a *Saccharomyces cerevisiae* strain engineered to use acetic acid as an electron acceptor. Applied and Environmental Microbiology 76:190-195. (Medina et al. 2010);

van Dijken J P, Bauer J, Brambilla L, Duboc P, Francois J M, Gancedo C, Giuseppin M L F, Heijnen J J, Hoare M, Lange H C, Madden E A, Niederberger P, Nielsen J, Parrou J L, Petit T, Porro D, Reuss M, van Riel N, Rizzi M, Steensma H Y, Verrips C T, Vindeløv J, Pronk J T. 2000. An interlaboratory comparison of physiological and genetic properties of four *Saccharomyces cerevisiae* strains. Enzyme and Microbial Technology 26:706-714. (van Dijken et al. 2000);

Verduyn C, Postma E, Scheffers W A, Van Dijken J P. 1992. Effect of benzoic acid on metabolic fluxes in yeasts: A continuous-culture study on the regulation of respiration and alcoholic fermentation. Yeast 8:501-517. (Verduyn et al. 1992);

Müller U M, Wu L, Raamsdonk L M, Winkler A A. Acetyl-coa producing enzymes in yeast. (Wiedemann and Boles, 2008);

US 20100248233 A1. Priority 30 Sep. 2010. (Müller et al. 2010);

Gietz R D, Woods R A. 2002. Transformation of yeast by lithium acetate/single-stranded carrier DNA/polyethylene glycol method. Methods in Enzymology 350:87-96. (Gietz and Woods, 2002);

Solis-Escalante D, Kuijpers N G A, Bongaerts N, Bolat I, Bosman L, Pronk J T, Daran J M, Daran-Lapujade P. 2013. amdSYM, a new dominant recyclable marker cassette for *Saccharomyces cerevisiae*. FEMS Yeast Res 13:126-139. (Solis-Escalante et al. 2013);

DiCarlo J E, Norville J E, Mali P, Rios X, Aach J, Church G M. 2013. Genome engineering in *Saccharomyces cerevisiae* using CRISPR-Cas systems. Nucleic Acids Research1-8. (DiCarlo et al. 2013);

Maris R, van Rossum H M, Wijsman M, Backx A, Kuijpers N G, van den Broek M, Daran-Lapujade P, Pronk J T, van Maris A J, Daran J M. 2015. CRISPR/Cas9: a molecular Swiss army knife for simultaneous introduction of multiple genetic modifications in *Saccharomyces cerevisiae*. FEMS Yeast Research; 15: fov004 (Maris et al. 2015);

Pickl et al. FEMS Biotechnology Letters, Volume 361, Issue 1, p. 76-83, December 2014: Identification and characterization of 2-keto-3-deoxygluconate kinase and 2-keto-3-deoxygalactonate kinase in the haloarchaeon *Haloferax volcanii* (Pickl and Schönheid 2015).

The invention claimed is:

1. A yeast cell that is genetically modified, to comprise one or more heterologous genes encoding
   a) an enzyme having NAD dependent D-glucose-6-phosphate dehydrogenase activity and/or
   b) an enzyme having NAD dependent 6-phosphogluconate dehydrogenase activity; and/or
   c) enzymes having, gluconolactonase (E.C. 3.1.1.17), gluconate kinase (E.C. 2.7.1.12), and NAD$^+$dependent glucose dehydrogenase activities (E.C. 1.1.1.118) wherein the yeast cell was capable of alcoholic fermentation before or after being genetically modified to comprise the one or more heterologous genes.

2. The yeast cell according to claim 1 comprising two heterologous genes encoding:
   a) the enzyme having the NAD+ dependent D-glucose-6-phosphate dehydrogenase activity and
   b) the enzyme having the NAD+ dependent 6-phosphogluconate dehydrogenase activity.

3. The yeast cell according to claim 1, further comprising:
   d) one or more heterologous nucleotide sequences encoding an enzyme having $NAD_+$-dependent acetylating acetaldehyde dehydrogenase activity (E.C. 1.2.1.10) and
   e) one or more homologous or heterologous nucleotide sequences encoding an enzyme having acetyl-CoA synthetase activity (E.C. 6.2.1.1); and optionally, comprises a modification that leads to reduction of endogenous glycerol 3-phosphate phosphohydrolase activity (E.C. 3.1.3.21) and/or endogenous glycerol 3-phosphate dehydrogenase activity (E.C 1.1.1.8 or E.C. 1.1.5.3) activity in the yeast cell.

4. The yeast cell according to claim 1, wherein an endogenous gene encoding acetaldehyde dehydrogenase-6 (ALD6) is disrupted.

5. The yeast cell according to claim 1, the heterologous gene encoding the enzyme having NAD dependent D-glucose-6-phosphate dehydrogenase activity replaces the endogenous gene encoding the enzyme having D-glucose-6-phosphate dehydrogenase activity in the eukaryotic cell and/or wherein the heterologous gene encoding the enzyme having NAD dependent 6-phosphogluconate dehydrogenase activity replaces the endogenous gene encoding the enzyme having 6-phosphogluconate dehydrogenase activity in the yeast cell.

6. The yeast cell according to claim 5, wherein the endogenous genes are part of the pentose-phosphate-pathway, are NADP$^+$dependent, and are selected from the group consisting of 6-phosphogluconate dehydrogenase 1 (GND1), 6-phosphogluconate dehydrogenase 2 (GND2), and D-glucose-6-phosphate dehydrogenase (ZWF1).

7. The yeast cell according to claim 1, wherein the heterologous genes are prokaryotic genes or synthetic genes encoding prokaryotic enzymes.

8. The yeast cell according to claim 1, wherein the enzyme having $NAD_+$ D-glucose-6-phosphate dehydrogenase activity has at least 60% sequence identity to the amino acid sequence of SEQ ID, NO:8.

9. The yeast cell according to claim 1, wherein the enzyme having $NAD_+$6-phosphogluconate dehydrogenase activity has at least 60% sequence identity to the amino acid sequence of SEQ ID, at NO:2, SEQ ID NO:4 or SEQ ID NO:6.

10. The yeast cell according to claim 1, wherein the heterologous genes are genes a) and/or b), and originate from an organism selected from the genus consisting of *Methylobacillus, Gluconobacter, Bradyrhizobium* and *Haloferax*.

11. The yeast cell according to claim 10, wherein the heterologous genes originate from an organism selected from the species consisting of *Methylobacillus* flagellatus, *Gluconobacter oxydans, Bradyrhizobium* and *Haloferax volcanii*.

12. The yeast cell according to claim 1 herein the yeast cell is a *Saccharomyces* cell or *Saccharomyces cerevisiae* cell.

13. The yeast cell according to claim 1 wherein the yeast cell is a pentose and glucose fermenting yeast cell that is capable of anaerobic simultaneous pentose and glucose consumption.

14. A product comprising the yeast cell according to claim 1 for use in fermentation in the wine industry.

15. A product comprising the yeast cell according to claim 1 for use in fermentation in the biofuel industry.

16. A process for fermentation of a substrate to produce a fermentation product with the yeast cell according to claim 1, in the wine or biofuel industry, wherein the acetate consumption is at least 10%, at least 20%, or at least 25% increased relative to the corresponding fermentation with wild-type yeast cell.

17. The process according to claim 16, wherein the fermentation product is ethanol and the ethanol yield is at least about 0.5%, or at least 1% higher than that of a process with the corresponding wild-type yeast cell.

18. The process according to claim 16, wherein pentose and glucose are co-fermented.

19. The process according to claim 16, wherein a hydrolysate of lignocellulosic material is fermented.

20. The process according to claim 19, wherein the hydrolysate is an enzymatic hydrolysate of lignocellulosic material.

21. The process according to claim 19, wherein the hydrolysate comprises acetate.

22. The process according to claim 21 wherein the acetate comprising hydrolysate has an acetate concentration of 0.3% (w/w) or more.

23. A process for the fermentation of a substrate to produce a fermentation product with the yeast cell according to claim 1, in the wine industry, wherein the glycerol yield is at least 5%, at least 10% or at least 10% at least 20% or at least 30% higher than that of a process with the corresponding wild-type yeast cell.

24. The process according to claim 23, wherein the ethanol yield is not increased or decreased, compared to that of a process with the corresponding wild-type yeast cell.

\* \* \* \* \*